(12) United States Patent
Du et al.

(10) Patent No.: US 11,944,497 B2
(45) Date of Patent: Apr. 2, 2024

(54) ULTRASONIC BLOOD FLOW IMAGING DISPLAY METHOD AND ULTRASONIC IMAGING SYSTEM

(71) Applicant: SHENZHEN MINDRAY BIO-MEDICAL ELECTRONICS CO., LTD., Shenzhen (CN)

(72) Inventors: Yigang Du, Shenzhen (CN); Rui Fan, Shenzhen (CN); Yong Li, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 934 days.

(21) Appl. No.: 15/793,850

(22) Filed: Oct. 25, 2017

(65) Prior Publication Data
US 2018/0146952 A1 May 31, 2018

Related U.S. Application Data

(63) Continuation of application No. PCT/CN2015/077861, filed on Apr. 29, 2015.

(51) Int. Cl.
*A61B 8/00* (2006.01)
*A61B 8/06* (2006.01)
(Continued)

(52) U.S. Cl.
CPC ............... *A61B 8/463* (2013.01); *A61B 8/06* (2013.01); *A61B 8/145* (2013.01); *A61B 8/488* (2013.01);
(Continued)

(58) Field of Classification Search
CPC ........... A61B 8/06; A61B 8/145; A61B 8/463; A61B 8/469; A61B 8/488; A61B 8/5223; A61B 8/5246; G01S 7/52074
See application file for complete search history.

(56) References Cited

U.S. PATENT DOCUMENTS

| 5,441,052 A | * | 8/1995 | Miyajima ........... G01S 7/52071 600/455 |
| 5,443,071 A | | 8/1995 | Banjanin et al. |

(Continued)

FOREIGN PATENT DOCUMENTS

| CN | 101933817 A | 5/2001 |
| CN | 1650190 A | 8/2005 |

(Continued)

OTHER PUBLICATIONS

Lai et al. "Pixel distribution analysis of B-mode ultrasound scan images predicts histologic features of atherosclerotic carotid plaques". Journal of Vascular Surgery, vol. 35, No. 6, pp. 1210-1216 (Year: 2002).*

(Continued)

*Primary Examiner* — Keith M Raymond
*Assistant Examiner* — Milton Truong
(74) *Attorney, Agent, or Firm* — Kory D. Christensen

(57) ABSTRACT

An ultrasonic blood flow imaging display method and an ultrasonic imaging system. The system comprises: a probe (1); a transmitting circuit (2), configured to excite the probe (1) to transmit an ultrasonic beam to a scanning target; a receiving circuit (4) and a beam forming module (5), configured to receive an echo of the ultrasonic beam to obtain an ultrasonic echo signal; a data processing module (9), configured to obtain, according to the ultrasonic echo signal, blood flow velocity vector information and Doppler blood flow velocity information about a target point in the scanning target and at least part of ultrasonic images of the scanning target, and superposing the ultrasonic images and the Doppler blood flow velocity information to form a Doppler color blood flow graph; and a display (8), configured to contrastively display the blood flow velocity vector information and the Doppler color blood flow graph. By (Continued)

means of a mode of contrastively displaying a common blood flow display image and a vector blood flow, a better viewing angle is provided for a user.

34 Claims, 26 Drawing Sheets

(51) Int. Cl.
 *A61B 8/08* (2006.01)
 *A61B 8/14* (2006.01)
(52) U.S. Cl.
 CPC .......... *A61B 8/5246* (2013.01); *A61B 8/469* (2013.01); *A61B 8/5223* (2013.01)

(56) References Cited

U.S. PATENT DOCUMENTS

| | | | |
|---|---|---|---|
| 5,522,393 A | 6/1996 | Phillips et al. | |
| 6,245,017 B1* | 6/2001 | Hashimoto | A61B 8/06 128/916 |
| 6,749,569 B1* | 6/2004 | Pellegretti | A61B 8/08 600/441 |
| 2004/0267127 A1* | 12/2004 | Abend | G01S 15/8993 600/450 |
| 2005/0090743 A1* | 4/2005 | Kawashima | A61B 8/4254 600/443 |
| 2008/0221446 A1* | 9/2008 | Washburn | A61B 8/4254 600/437 |
| 2009/0292206 A1 | 11/2009 | Sato | |
| 2009/0326379 A1* | 12/2009 | Daigle | A61B 8/06 600/453 |
| 2011/0196237 A1* | 8/2011 | Pelissier | A61B 8/467 600/454 |
| 2013/0144166 A1* | 6/2013 | Specht | A61B 8/4444 600/441 |
| 2013/0150717 A1* | 6/2013 | Sato | A61B 8/5223 600/441 |
| 2013/0165783 A1* | 6/2013 | Kim | A61B 8/5246 600/441 |
| 2013/0172747 A1 | 7/2013 | Kim | |
| 2013/0321262 A1* | 12/2013 | Schecter | G06F 19/00 345/156 |
| 2014/0323868 A1 | 10/2014 | Ono | |
| 2014/0371594 A1* | 12/2014 | Flynn | G01S 15/8995 600/454 |
| 2015/0141832 A1* | 5/2015 | Yu | G01S 15/8984 600/455 |
| 2015/0265247 A1* | 9/2015 | Roh | A61B 8/08 600/440 |
| 2016/0106391 A1* | 4/2016 | Jensen | A61B 8/5207 600/447 |

FOREIGN PATENT DOCUMENTS

| | | |
|---|---|---|
| CN | 101081171 A | 12/2007 |
| CN | 101313856 A | 12/2008 |
| CN | 101584589 | 11/2009 |
| CN | 101919712 A | 12/2010 |
| CN | 102123668 A | 7/2011 |
| CN | 102370499 A | 3/2012 |
| CN | 103156647 | 6/2013 |
| CN | 103181788 | 7/2013 |
| CN | 103957812 | 7/2014 |
| CN | 104011559 A | 8/2014 |
| CN | 104105449 A | 10/2014 |
| CN | 104411249 A | 3/2015 |
| CN | 106102587 B | 6/2019 |

OTHER PUBLICATIONS

Ekroll, I.K. et al. "Combined Vector Velocity and Spectral Doppler Imaging for Improved Imaging of Complex Blood Flow in the Carotid Arteries", Ultrasound in Med. & Biol., vol. 40, No. 7, pp. 1629-1640, 2014 (Year: 2014).*

Lal et al., "Pixel distribution analysis of B-mode ultrasound scan images predicts histologic features of atherosclerotic carotid plaques", Journal of Vascular surgery, 2002, pp. 1210-1217.

Yiu et al., "Vector Projectile Imaging: Time-Resolved Dynamic Visualization of Complex Flow Patterns," Ultrasound in Medicine & Biology, vol. 40, Issue 9, Sep. 2014, pp. 2295-2309.

Ekroll et al., "Simultaneous Quantification of Flow and Tissue Velocities Based on Multi-Angle Plane Wave Imaging," IEEE Transactions on Ultrasonics, Ferroelectrics, and Frequency Control, vol. 60, No. 4, pp. 727-738, Apr. 2013.

Pastorelli et al. "A Real-Time 2-D Vector Doppler System for Clinical Experimentation," IEEE Transactions on Medical Imaging, vol. 27, No. 10, pp. 1515-1524, Oct. 2008.

Udesen et al., "High Frame-Rate Blood Vector Velocity Imaging Using Plane Waves: Simulations and Preliminary Experiments," EEE Transactions on Ultrasonics, Ferroelectrics, and Frequency Control, vol. 55, No. 8, pp. 1729-1743, Aug. 2008.

* cited by examiner

ULTRASONIC BLOOD FLOW IMAGING DISPLAY METHOD AND ULTRASONIC IMAGING SYSTEM

TECHNICAL FIELD

The present disclosure relates to blood flow imaging display techniques in an ultrasound imaging system, and more particularly to an ultrasonic blood flow imaging display system and an ultrasonic imaging system.

BACKGROUND

In a medical ultrasonic imaging device, ultrasonic waves are transmitted into the object to be inspected. In color Doppler blood imaging, as in pulse-wave Doppler imaging and continuous-wave Doppler imaging, images may be obtained utilizing the Doppler effect between red blood cells and ultrasonic waves. A color Doppler blood imaging device may include a two-dimensional ultrasonic imaging system, a pulse-wave Doppler (one-dimensional Doppler) blood flow analysis system, a continuous-wave Doppler blood flow measurement system, and a color Doppler (two-dimensional Doppler) blood flow imaging system. An oscillator generates two orthogonal signals with a phase difference of nic The two signals are multiplied by the Doppler blood flow signals, and thereafter, the product is converted into digital signal by an analog-to-digital (A/D) converter. After being filtered by a comb filter in order to remove the low frequency components generated by vascular wall or valve, etc., the converted digital signal is sent to an auto-correlator where autocorrelation is performed thereon. Since each sample includes the Doppler blood flow information generated by multiple red blood cells, the signal obtained by the autocorrelation is a mixed signal of multiple blood flow velocities. The results of the autocorrelation are sent to a velocity calculator and a variance calculator to obtain mean velocities. The mean velocities may be stored in a digital scan converter (DSC) together with the blood flow spectrum information processed by fast Fourier transform (FFT) and two-dimensional image information. Thereafter, the blood flow information is pseudo-color coded by a color processor based on the directions and velocity magnitudes of the blood flow and displayed on a color display, thereby achieving the color Doppler blood flow imaging.

The color Doppler blood flow imaging cannot display the actual direction and velocity or velocity dispersion of the blood flow. However, the color Doppler blood flow imaging has a unique function, i.e., it can display the presence of the blood flow and the strength thereof with high sensitivity and high signal to noise ratio. In view of the defects of the color Doppler blood flow imaging in displaying the blood flow mentioned above, there is a need for providing a more intuitive solution for displaying the blood flow information.

SUMMARY

The present disclosure provides ultrasound blood flow imaging display methods and an ultrasound imaging system which can provide more intuitive blood flow display and better visibility for the user.

In one embodiment, an ultrasound flow imaging display method may be provided. The method may include transmitting ultrasound beams to a scanning target; receiving echoes of the ultrasound beams to obtain ultrasound echo signals; obtaining ultrasound images of at least a portion of the scanning target according to the ultrasound echo signals; obtaining flow velocity vector information of target points in the scanning target and Doppler flow velocity information according to the ultrasound echo signals; superimposing the ultrasound images and the Doppler flow velocity information to form Doppler color flow images; and comparatively displaying the flow velocity vector information and the Doppler color flow images.

In one embodiment, an ultrasound imaging system may be provided. The system may include a probe; a transmitting circuit which may excite the probe to transmit ultrasound beams to a scanning target; a receiving circuit and a beamforming unit which may receive echoes of the ultrasound beams to obtain ultrasound echo signals; a data processing unit which may obtain ultrasound images of at least a portion of the scanning target, flow velocity vector information of target points in the scanning target and Doppler flow velocity information according to the ultrasound echo signals and superimpose the ultrasound images and the Doppler flow velocity information to form Doppler color flow images; and a display which may comparatively display the flow velocity vector information and the Doppler color flow images.

In various embodiments, the ordinary flow images and the vector flow images may be comparatively displayed, such that better observation may be provided for the user. Not only may the positions being scanned be observed in real time, but also more intuitive flow display may be provided. Furthermore, the flow may be represented more realistically, and the comfort of the human eye may be ensured.

DETAILED DESCRIPTION

Figure 1:
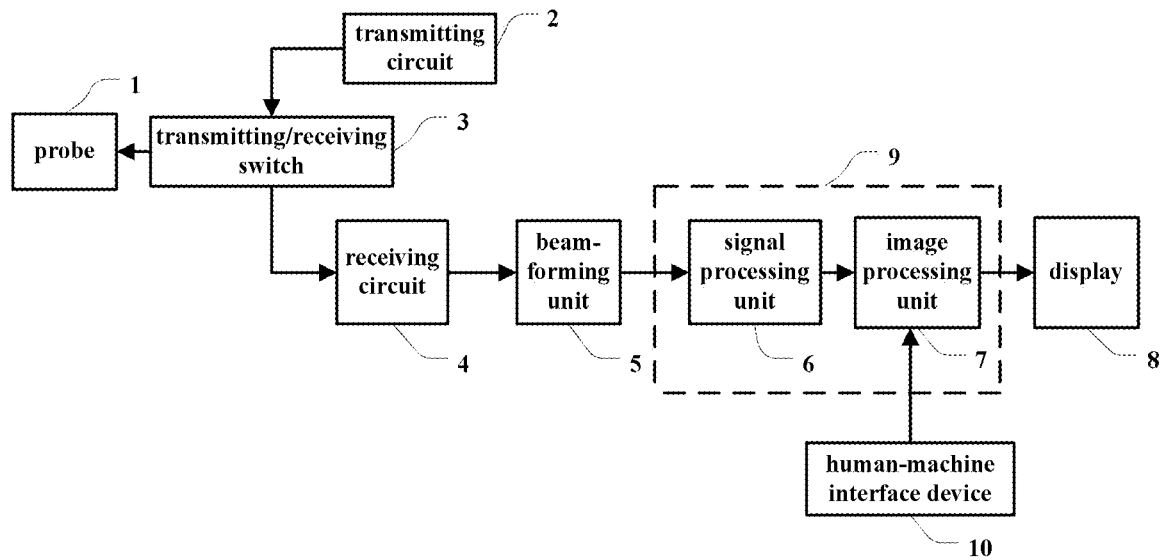
FIG. 1 is a schematic block diagram of an ultrasound imaging system in an embodiment.

FIG. 1 schematically shows a block diagram of an ultrasound imaging system according to an embodiment of the present disclosure. As shown in FIG. 1, the ultrasound imaging system may generally include a probe 1, a transmitting circuit 2, a transmitting/receiving switch 3, a receiving circuit 4, a beam-forming unit 5, a signal processing unit 6, an image processing unit 7 and a display 8.

In an ultrasound imaging process, the transmitting circuit 2 may transmit transmitting pulses, which have been delay focused and have certain amplitude and polarity, to the probe 1 through the transmitting/receiving switch 3. The probe 1 may be excited by the transmitting pulses and thereby transmit ultrasound waves to a scanning target (e.g., organs, tissues, blood vessels or the like within a human or animal body, not shown), receive ultrasound echoes which are reflected by a target region and carry information related to the scanning target after a certain time interval, and convert the ultrasound echoes into electric signals. The receiving circuit may receive the electric signals converted by the probe 1 to obtain ultrasound echo signals and send the ultrasound echo signals to the beam-forming unit 5. The beam-forming unit 5 may perform processing, such as focus delaying, weighting, and channel summing, etc. on the ultrasound echo signals and then send the ultrasound echo signals to the signal processing unit 6, where related signal processing procedures will be performed on the ultrasound echo signals.

The ultrasound echo signals processed by the signal processing unit 6 may be sent to the image processing unit 7. The processing unit 7 may process the signals in different ways according to the imaging mode desired by the user in order to obtain image data in different mode. Thereafter, the image data may undergo the processing such as logarithmic compression, dynamic range adjustment and digital scan conversion, etc. to form ultrasound images of different modes, for example, two-dimensional images such as B images, C images or D images, etc. In addition, the ultrasound images may also include three-dimensional ultrasound images.

The ultrasound images formed in the image processing unit 7 may be sent to the display 8 where they are displayed.

The probe 1 may generally include an array of multiple transducers. Each time the ultrasound waves are transmitted, all, or a part, of the transducers of the probe 1 may be used. In this case, each, or each part, of the used transducers may be respectively excited by the transmitting pulse and respectively transmit ultrasound waves. The ultrasound waves transmitted by the transducers may superpose with each other during the propagation thereof to form a resultant ultrasound beam transmitted to the scanning target. The direction of the resultant ultrasound beam may be the "ultrasound propagation direction" mentioned in the present disclosure.

The used transducers may be simultaneously excited by the transmitting pulses. Alternatively, a certain time delay may exist between the excitation times of the used transducers by the transmitting pulses. By controlling the time delay between the excitation times of the used transducers by the transmitting pulses, the propagation direction of the resultant ultrasound beam can be changed, as described in details below.

By controlling the time delay between the excitation times of the used transducers by the transmitting pulses, it may also be possible that the ultrasound waves transmitted by the used transducers neither focus nor completely diffuse during the propagation thereof, but form a plane wave which is substantially planar as a whole. In the present disclosure, such plane wave without a focus may be referred to as a "plane ultrasound beam".

Figure 4:
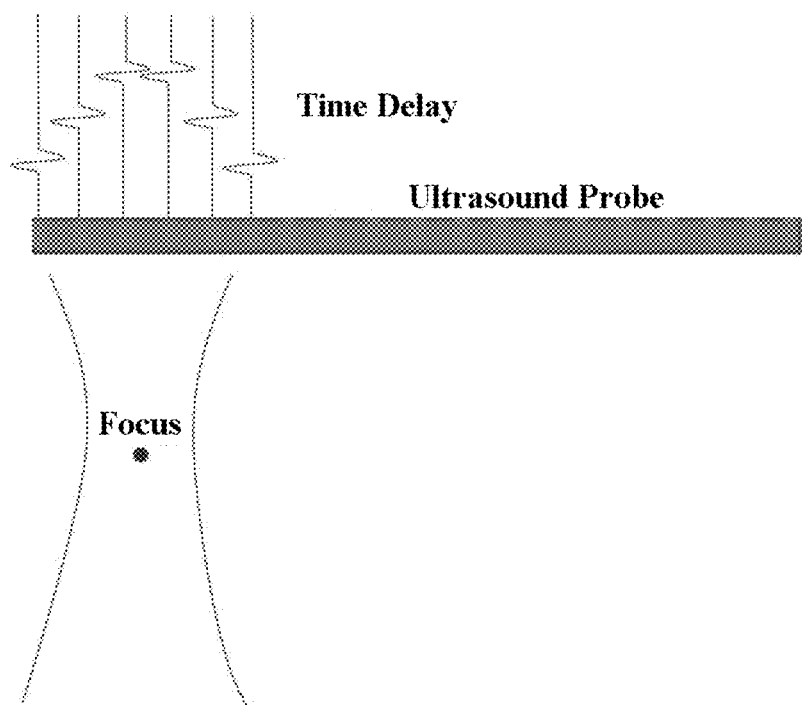
FIG. 4 schematically shows the focused ultrasound beam in an embodiment.

Alternatively, by controlling the time delay between the excitation times of the used transducers by the transmitting pulses, it may also be possible that the ultrasound waves transmitted by the transducers are superposed at a predetermined position such that the strength of the ultrasound waves at the predetermined position is maximum, in other words, such that the ultrasound waves transmitted by the transducers may be "focused" at the predetermined position. Such predetermined position may be referred to as a "focus". In this case, the obtained resultant ultrasound beam may be a beam focused at the focus, which may be referred to as a "focused ultrasound beam" in the present disclosure. For example, FIG. 4 schematically shows the transmitting of a focused ultrasound beam. Here, the used transducers (in FIG. 4, only a part of the transducers of the probe 1 are used) may work with a predetermined transmission time delay (i.e., a predetermined time delay may exist between the excitation times of the used transducers by the transmitting pulses) and the ultrasound waves transmitted by the transducers may be focused at the focus to form the focused ultrasound beam.

Figure 5:
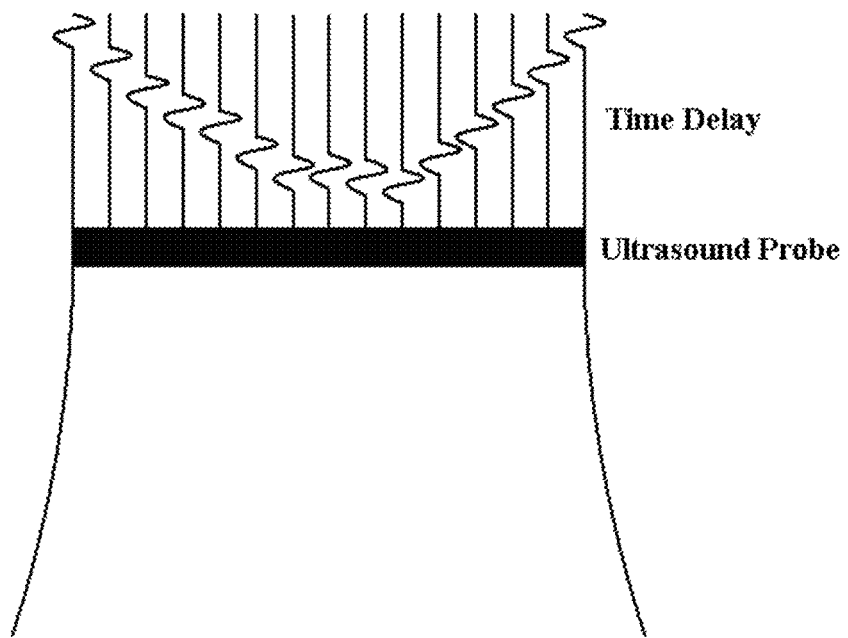
FIG. 5 schematically show the diffused ultrasound beam in an embodiment.

Alternatively, by controlling the time delay between the excitation times of the used transducers by the transmitting pulses, it may also be possible that the ultrasound waves transmitted by the used transducers are diffused during the propagation to form a diffused wave which is substantially diffused as a whole. In the present disclosure, such diffused ultrasound wave may be referred to as a "diffused ultrasound beam". An example of the diffused ultrasound beam is shown in FIG. 5.

Figure 2:
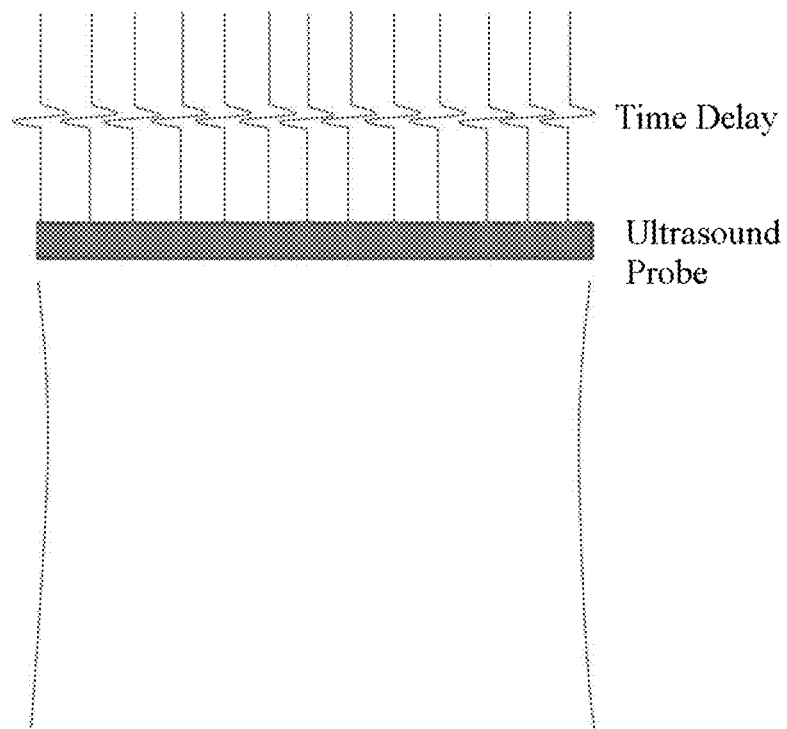
FIG. 2 schematically shows the plane ultrasound beam transmitted vertically in an embodiment.
Figure 3:
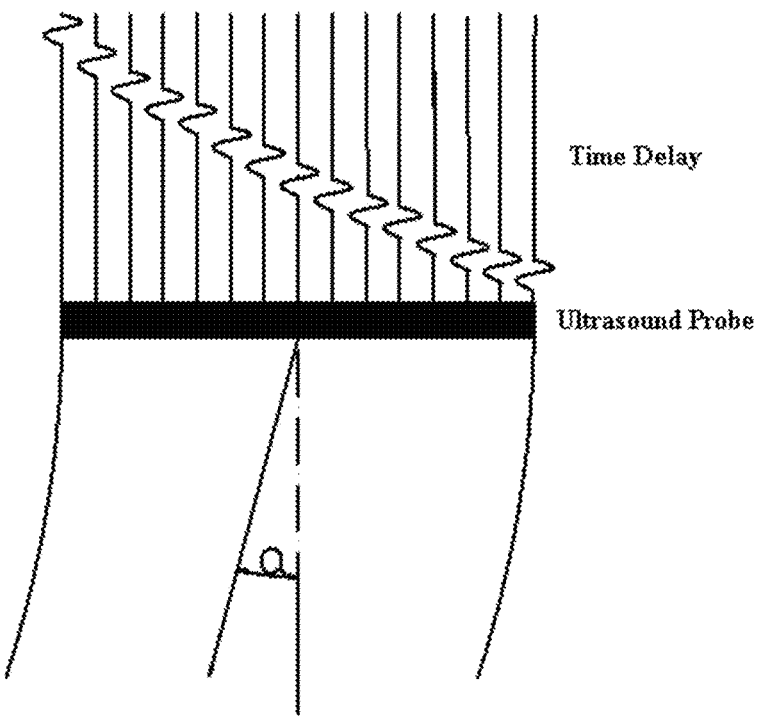
FIG. 3 schematically shows the plane ultrasound beam transmitted with a steered angle.

In the case that multiple transducers linearly arranged are excited simultaneously by electronic pulses, the transducers will simultaneously transmit ultrasound waves and the propagation direction of the resultant ultrasound beam will be the same as the normal direction of the plane on which the transducers are arranged. For example, for the plane beam vertically transmitted shown in FIG. 2, there is no time delay between the used transducers (i.e., there is no time delay between the excitation times of the transducers by the transmitting pulses) and the transducers are excited simultaneously. The ultrasound beam formed thereby is a plane beam, i.e., a plane ultrasound beam. The propagation direction of this plane ultrasound beam is substantially perpendicular to the surface of the probe 1 from which the ultrasound waves are transmitted, i.e., the angle between the propagation direction of the resultant ultrasound beam and the normal direction of the plane on which the transducers are arranged is zero degree. However, in the case that there is time delay between the excitation pulses applied to the transducers, the transducers will successively transmit ultrasound waves according to the time delay, and there will be an certain angle between the propagation direction of the resultant ultrasound beam and the normal direction of the plane on which the transducers are arranged. This angle is the steered angle of the resultant beam. By changing the time delay, the magnitude of the steered angle, and the direction of the steering in the scanning plane of the resultant beam with respect to the normal direction of the plane on which the transducers are arranged, of the resultant beam may be adjusted. For example, FIG. 3 schematically shows a plane beam with a steered angle. In this case, there is a predetermined time delay between the used transducers (i.e., between the excitation times of the used transducers by the transmitting pulses), and the transducers are excited in a predetermined order by the transmitting pulses. The ultrasound beam generated thereby is a plane beam, i.e., a plane ultrasound beam, and there is an angle (e.g., the angle a in FIG. 3) between the propagation direction of this plane ultrasound beam and the normal direction of the plane on which the transducers of the probe 1 are arranged. This angle is the steered angle of the plane ultrasound beam. By changing the time delay, the magnitude of the angle a may be adjusted.

Similarly, regardless of the plane ultrasound beam, the focused ultrasound beam or the diffused ultrasound beam, the "steered angle" of the resultant beam formed between the direction of the resultant beam and the normal direction of the plane on which the transducers are arranged can be adjusted by adjusting the time delay between the excitation times of the used transducers by the transmitting pulses. The "resultant beam" herein may be the plane ultrasound beam, the focused ultrasound beam or the diffused ultrasound beam mentioned above.

Figure 6A:
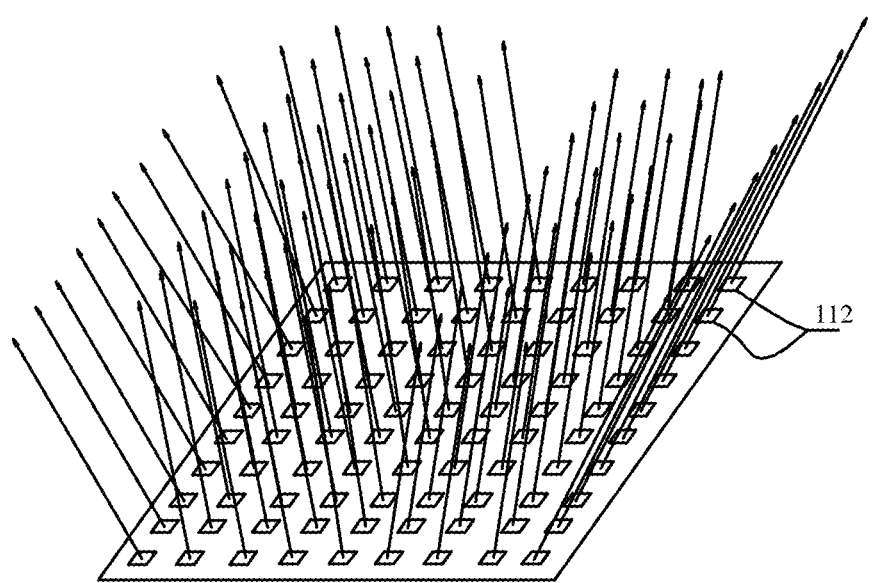
FIG. 6A schematically shows the transducers of two dimensional array probe, FIG. 6B schematically shows the 3D scanning along an ultrasound propagation direction using the two dimensional array probe, and FIG. 6C schematically shows the measurement of the steering of the scanning body in FIG. 6B.
Figure 6B:
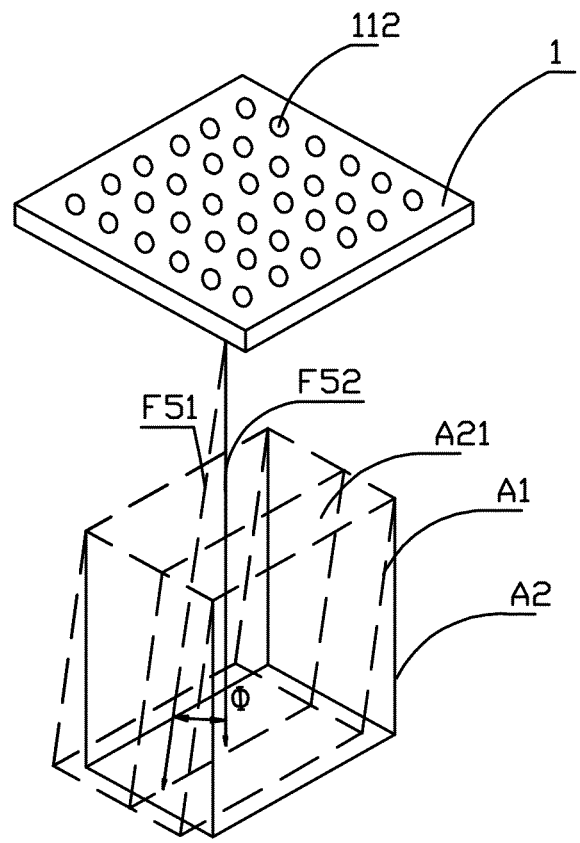
Figure 6C:
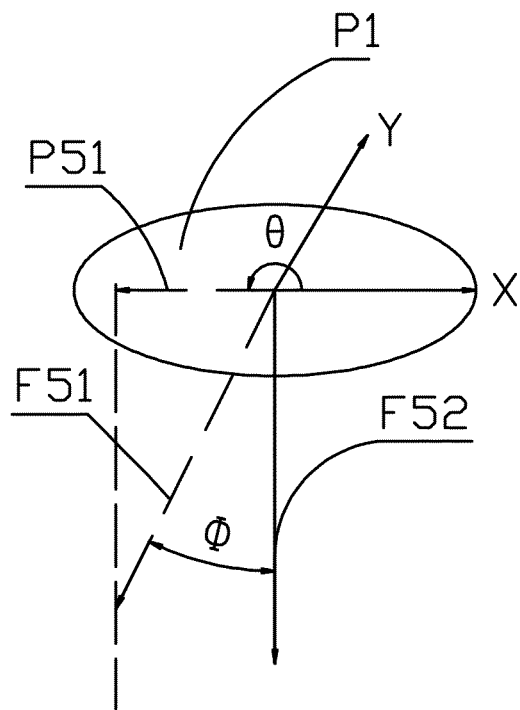

When performing a three-dimensional ultrasound imaging, a two-dimensional array probe may be used, as shown in FIG. 6A. The two-dimensional array probe may include multiple transducers 112 which are arranged in transverse and longitudinal directions. Each transducer of the two-dimensional array probe may be provided with a delay control line which may be used to control the time delay of the corresponding transducer. During the transmitting and the receiving of the ultrasound beam, the beam control and the dynamic focus of the ultrasound beam may be implemented by adjusting the time delay of each transducer, thereby changing the direction of the beam in order to implement the scanning of the beam in a three-dimensional space to obtain three-dimensional image data. As shown in FIG. 6B, the two-dimensional array probe 1 may include multiple transducers 112. By changing the time delay of the transducers used in the transmitting of the ultrasound waves, the transmitted ultrasound beam may propagate in the direction indicated by the dot-chain arrow F51 and form, in the three-dimensional space, a scanning body A1 (the three-dimensional structure drawn by the dot-chain lines in FIG. 6B) for obtaining three-dimensional image data. The scanning body A1 may have a predetermined steering with respect to a reference body A2 (the three-dimensional structure drawn by the solid lines in FIG. 6B). The reference body A2 herein may be formed in the three-dimensional space by making the ultrasound beam transmitted by the used transducers to propagate in the normal direction of the plane on which the transducers are arranged (indicated by the solid-line arrow F52). Therefore, the steering amount of the scanning body A1 with respect to the reference body A2 may be used to measure the steered angle in a three-dimensional space of a scanning body formed by the propagation of an ultrasound beam in a certain direction with respect to the reference body A2. In the present disclosure, the steering amount may be measured by following two angles: first, the predetermined steered angle $\phi$ between the propagation direction of the ultrasound beam and the normal direction of the plane on which the transducers are arranged in the scanning plane A21 (the quadrilateral drawn by the dot-chain lines in FIG. 6 B) of the ultrasound beam in the scanning body, which is in the range of [0, 90°), and second, the rotation angle $\theta$ formed by, in the plane rectangular coordinate system in the plane P1 on which the transducers are arranged, counterclockwise rotating from X axis to the projection P51 (the dot-chain arrow in plane P1 in FIG. 6 C) of the propagation direction of the ultrasound beam on the plane P1 on which the transducers are arranged, which is in the range of [0, 360°). In the case that the steered angle $\phi$ is zero, the steering amount of the scanning body A1 with respect to the reference body A2 is zero. During a three-dimensional ultrasound imaging, by changing the time delay of each transducer, the magnitude of the steered angle $\phi$ and the rotation angle $\theta$ may be changed, thereby adjusting the steering amount of the scanning body A1 with respect to the reference body A2 and forming different scanning bodies in different ultrasound propagation directions in the three-dimensional space.

The plane ultrasound beam generally may cover almost entire imaging area of the probe 1. Therefore, when performing the imaging with the plane ultrasound beams, one transmission may obtain one frame of ultrasound image ("one frame of ultrasound image" herein should be understood as including one frame of two-dimensional image data or one frame of three-dimensional image data, and the same as below), and thereby the imaging frame rate may be very high. When performing the imaging with the focused ultrasound beams, since the beam is focused at the focus, one transmission can only obtain one or several scanning lines and multiple transmissions are needed to obtain all scanning lines in the imaging area thereby combining all of the scanning lines to obtain one frame of ultrasound image of the image area. Therefore, when performing the imaging with the focused ultrasound beams, the frame rate is relatively low. However, the energy of the focused ultrasound beam is concentrated and the imaging is performed at the energy concentration location. Accordingly, the echo signals obtained will have high signal-to-noise ratio and can be used to obtain ultrasound images with better quality.

In the present disclosure, based on the color Doppler imaging techniques, the ordinary Doppler color flow image and the vector flow images may be displayed simultaneously, thereby providing users with a better viewing perspective. Not only the velocity and direction of the flow at the scanned location can be shown in real time, but also the displayed images can more truthfully represent the flow information and ensure the comfort of the human eye during the observation. Several embodiments of the present disclosure will be described in detail below with referent to the drawings.

Figure 7:
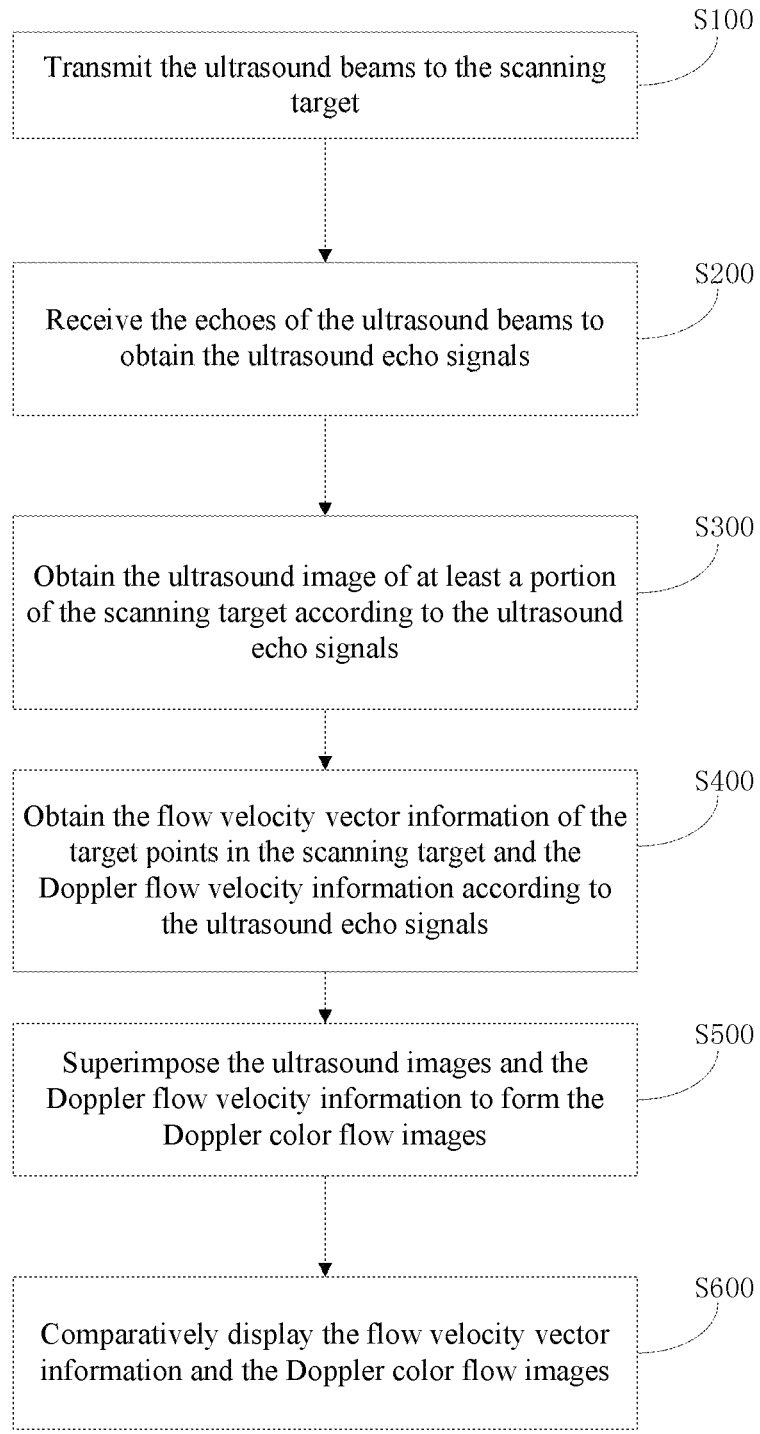
FIG. 7 is a schematic flow chart of a method in an embodiment.

As shown in FIG. 7, in one embodiment, an ultrasound flow imaging method may be provided. The method may, based on Doppler flow imaging techniques, simultaneously display the ordinary Doppler flow images and the vector flow images, thereby providing the users with better viewing perspective and achieving not only representing the scanned location in real-time, but also more truthfully representing the flow information. Furthermore, the method may comparatively show the variety of information of the flow velocity such that the users can more comprehensively understand the situation of the flow and more comprehensive, more accurate image data can be provided to medical staffs, thereby creating a new flow imaging method for achieving the imaging of the flow in an ultrasound imaging system. As shown in FIG. 7, in one embodiment, an ultrasound flow imaging method may include step S100 to step S600.

In step S100, the transmitting circuit 2 may excite the probe 1 to transmitting ultrasound beams to a scanning target.

In the present disclosure, the ultrasound beams transmitted to the scanning target may include at least one or more kinds of focused ultrasound beam, unfocused ultrasound beam, virtual source ultrasound beam, non-diffractive ultrasound beam, diffused ultrasound beam and plane ultrasound beam, etc. However, the present disclosure will not be limited to the ultrasound beams mentioned above.

Figure 8:
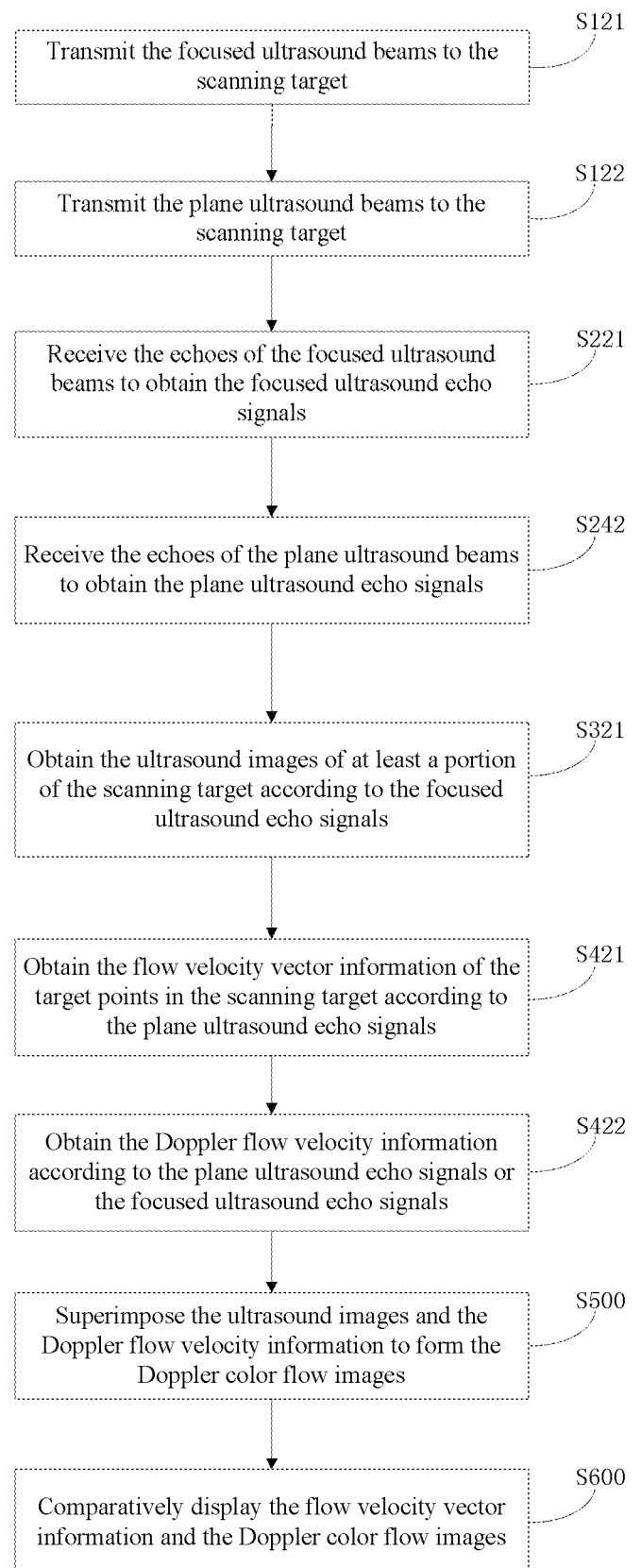
FIG. 8 is a schematic flow chart of a method in an embodiment.

In one embodiment of the present disclosure, as shown in FIG. 8, step S100 may include a step S121: transmitting the focused ultrasound beams to the scanning target to obtain the focused ultrasound echo signals. The focused ultrasound echo signals may be used as basic data for reconstructing ultrasound images, calculating the Doppler flow velocity information, calculating the flow velocity vector information, etc.

Alternatively, with reference to FIG. 8, step S100 may include step S122: transmitting the plane ultrasound beams to the scanning target to obtain the plane ultrasound echo signals. The plan ultrasound echo signals may also be used as basic data for reconstructing ultrasound images, calculating the Doppler flow velocity information, calculating the flow velocity vector information, etc.

Alternatively, as shown in FIG. 8, step S100 may include step S121 and step S122: transmitting the focused ultrasound beams to the scanning target to obtain the focused ultrasound echo signals and transmitting the plane ultrasound beams to the scanning target to obtain the plane ultrasound echo signals. The focused ultrasound echo signals may be used to reconstruct the ultrasound images of at least a part of the scanning target, thereby obtaining ultrasound images with better quality as background images. As shown in FIG. 8, in step S421, the plane ultrasound echo signals may be used as the basic data for calculating the flow velocity vector information. Herein, the Doppler flow velocity information may be obtained based on the focused ultrasound echo signals or the plane ultrasound echo signals, as shown by step S422.

In the case that two kinds of ultrasound beams are used in step S 100, the two kinds of ultrasound beams may be transmitted to the scanning target alternately. For example, the transmission of the focused ultrasound beam to the scanning target may be inserted between the transmissions of the plane ultrasound beams to the scanning target, i.e., step S121 and step S122 as shown in FIG. 8 may be performed alternately. This way, the synchronization of the acquisition of the image data using the two kinds of ultrasound beams can be ensured, and the accuracy of the superimposition of the vector flow images on the background images can be increased.

Figure 9:
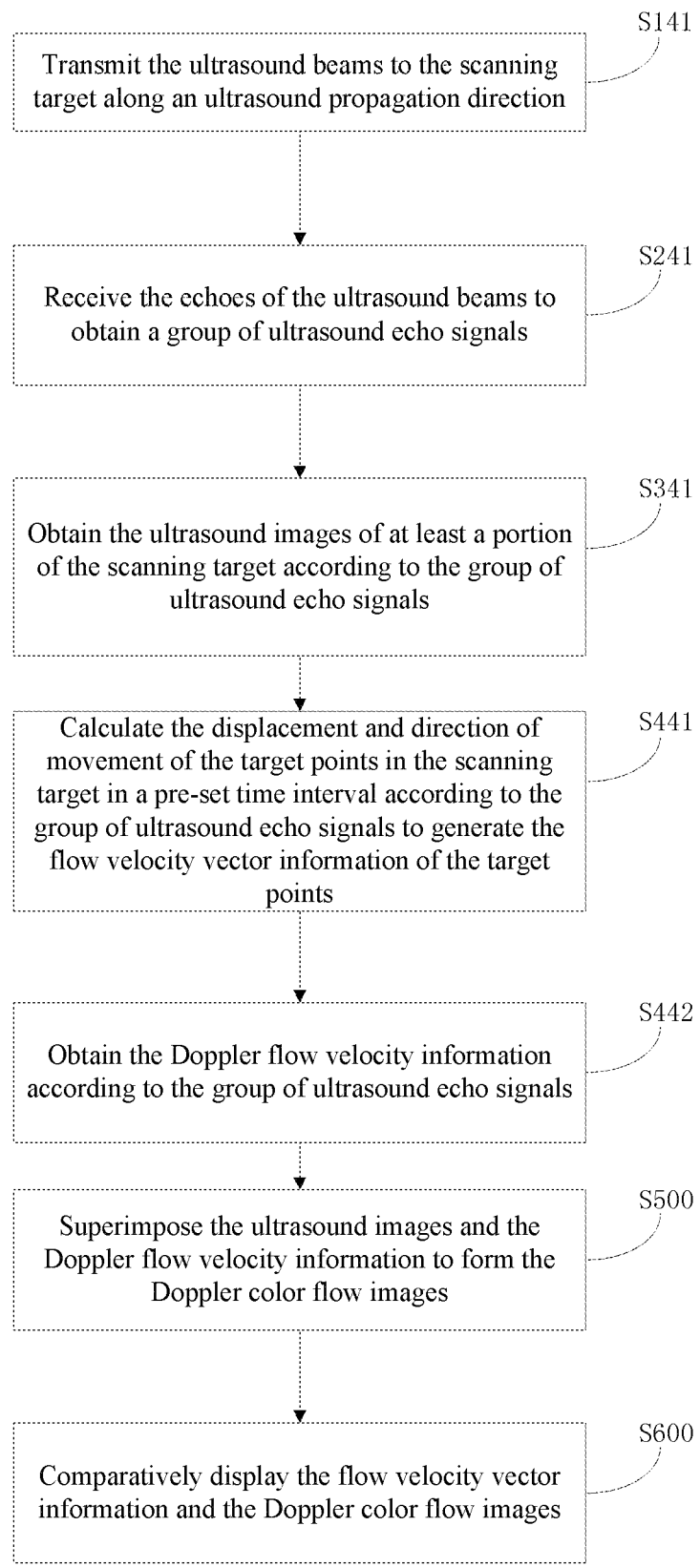
FIG. 9 is a schematic flow chart of a method in an embodiment.
Figure 10:
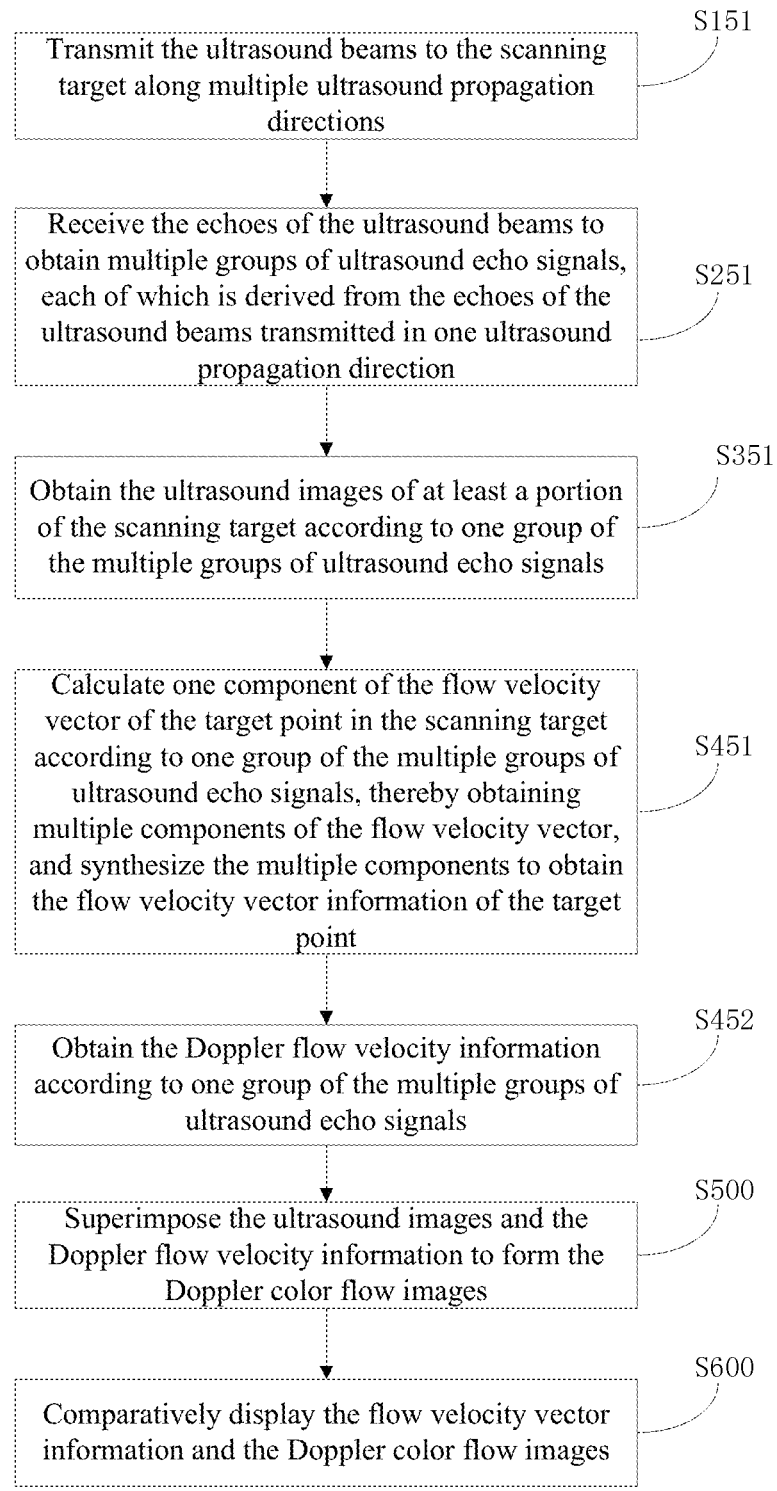
FIG. 10 is a schematic flow chart of a method in an embodiment.

In step S100, the ultrasound beams may be transmitted to the scanning target according Doppler imaging techniques in order to obtaining the ultrasound echo signals to be used for calculating the Doppler flow velocity information. For example, ultrasound beams in a single angle may be transmitted to the scanning target. In order to obtain the flow velocity vector information, ultrasound beams may be transmitted to the scanning target according to vector flow imaging techniques. For example, ultrasound beams in a single angle or multiple angles may be transmitted to the scanning target. In other words, the ultrasound beams may be transmitted to the scanning target in one or more ultrasound propagation directions. In one embodiment, as shown in FIG. 9 and FIG. 10, in step S100, the plane ultrasound beams may be transmitted to the scanning target in one or more ultrasound propagation directions, i.e., in step S100, one of step S 141 in FIG. 9 and step S151 in FIG. 10 may be performed. The more ultrasound propagation directions may include two or more ultrasound propagation directions, and the same as below.

In one embodiment, as shown in FIG. 10, step S100 may include a step S151: transmitting the ultrasound beams to the scanning target in multiple ultrasound propagation directions, in which the ultrasound beams in different ultrasound propagation directions may be transmitted to the scanning target alternately. For example, in the case that the ultrasound beams are transmitted to the scanning target in two ultrasound propagation directions, firstly an ultrasound beam in the first ultrasound propagation direction may be transmitted to the scanning target and then an ultrasound beam in the second ultrasound propagation direction may be transmitted to the scanning target, thereby completing one scanning cycle. Thereafter, the scanning cycle above may be repeated. Alternatively, it may also be possible to transmit the ultrasound beams in one ultrasound propagation direction to the scanning target and then transmit the beams in another ultrasound propagation direction to the scanning target, thereby completing the scanning after the ultrasound beams in all ultrasound propagation directions are successively transmitted. The ultrasound beams with different ultrasound propagation directions may be obtained by adjusting the time delay of each or each part of the transducers used in the transmission of the ultrasound waves, as explained in the description related to FIG. 2 to FIG. 6A-6C.

For example, transmitting the plane ultrasound beams to the scanning target in multiple ultrasound propagation directions may include transmitting a first ultrasound beam with a first steered angle to the scanning target and transmitting a second ultrasound beam with a second steered angle to the scanning target. The echoes of the first ultrasound beam and the echoes of the second ultrasound beam may be received, thereby obtaining a first ultrasound echo signal and a second ultrasound echo signal. The method for achieving the steered angle may be the same as the detailed description with respect to FIG. 2 above. In one embodiment, the first ultrasound beam and the second ultrasound beam may be plane ultrasound beam, and correspondingly, the first ultrasound echo signal and the second ultrasound echo signal may be the first plane ultrasound echo signal and the second plane ultrasound echo signal.

In one embodiment, transmitting the plane ultrasound beams to the scanning target in multiple ultrasound propagation directions may include transmitting ultrasound beams to the scanning target in N (N may be a natural number greater than or equal to 3) ultrasound propagation directions. The echoes of the ultrasound beams may be received, thereby obtaining N (N may be a natural number greater than or equal to 3) groups of ultrasound echo signals, where each group of ultrasound echo signals may be derived from the ultrasound beam transmitted in one ultrasound propagation direction. The N groups of ultrasound echo signals may mainly be used to calculate the flow velocity vector information, which may be described in detail below.

In one embodiment, the ultrasound beams may be transmitted to the scanning target in at least three ultrasound propagation directions, which may include:

exciting a part, or all, of the transducers to transmit ultrasound beams to the scanning target in at least three ultrasound propagation directions such that the ultrasound beams to propagate in a space in which the scanning target is located to form at least three scanning bodies. The ultrasound beams in the present embodiment may be, for example, plane ultrasound beams.

Alternatively, in one embodiment, transmitting ultrasound beams to the scanning target in at least three ultrasound propagation directions may include:

dividing the transducers into multiple transducer regions and exciting a part, or all, of the transducer regions to transmit ultrasound beams to the scanning target in at least three ultrasound propagation directions such that the ultrasound beams propagate in a space in which the scanning target is located to form at least three scanning bodies, where each scanning body may be derived from the ultrasound beam transmitted in one ultrasound propagation direction. The forming of the scanning bodies may be the same as the detailed description with respect to FIG. 6A to FIG. 6C above and will not be described again. The ultrasound beams in the present embodiment may, for example, include one of the focused ultrasound beam and the plane ultrasound beam, etc., but not limited thereto. In the present embodiment, in the case that the focused ultrasound beams are used and the transducers are divided into multiple transducer regions, exciting one of the transducer regions may generate one focused ultrasound beam, and simultaneously exciting multiple transducer regions may generate multiple focused ultrasound beams which may form one scanning body.

In one embodiment, the ultrasound beams in each ultrasound propagation direction may be transmitted to the scanning target for multiple times, thereby obtaining multiple ultrasound echo signals for subsequent processing of the ultrasound image data. For example, the plane ultrasound beam may respectively be transmitted to the scanning target for multiple times in each of the multiple propagation directions, or the focused ultrasound beam may respectively be transmitted to the scanning target for multiple times in each of one or more ultrasound propagation direction. Each transmission of the ultrasound beam may correspondingly obtain one ultrasound echo signal.

Transmitting the ultrasound beams to the scanning target for multiple times alternately in different ultrasound propagation directions may enable the calculation of the flow velocity of a target point at a certain time using the echo data and increase the accuracy of the calculation of the flow velocity vector information. For example, in the case that the ultrasound beams will be transmitted to the scanning target for N times respectively in three ultrasound propagation directions, the ultrasound beam may be transmitted to the scanning target in a first ultrasound propagation direction for at least one time, then the ultrasound beam may be transmitted to the scanning target in a second ultrasound propagation direction for at least one time, and then the ultrasound beam may be transmitted to the scanning target in a third ultrasound propagation direction for at least one time, thereby completing one scanning cycle. The scanning cycle above may be repeated until all scanning in all ultrasound propagation directions are completed. The numbers of the transmission of the ultrasound beam in different ultrasound propagation directions in one scanning cycle may be the same or different. For example, in the case that the ultrasound beam will be transmitted in two ultrasound propagation directions, the transmission sequence may be A1 B1 A2 B2 A3 B3 A4 B4 beams will be transmitted to the scanninth transmission in a first ultrasound propagation direction and Bi may be the ith transmission in a second ultrasound propagation direction. In the case that the ultrasound beam will be transmitted in three ultrasound propagation directions, the transmission sequence may be A1 B1 B1C1 A2 B2 B2C2 A3 B3 B3C3 in a seBi Ci, and so on, where Ai may be the ith transmission in a first ultrasound propagation direction, Bi may be the ith transmission in a second ultrasound propagation direction, and Ci may be the ith transmission in a third ultrasound propagation direction.

In addition, in the case that two kinds of ultrasound beams will be transmitted to the scanning target in step S100, the two kinds of ultrasound beams may be transmitted alternately. For example, in one embodiment, step S100 may include:

step S101: transmitting the focused ultrasound beams to the scanning target for multiple times to obtain the image data used for reconstructing the ultrasound images; and step S102: transmitting the plane ultrasound beams to the scanning target for multiple times in one or more ultrasound propagation directions to obtain the image data used for calculating the flow velocity vector information.

In this embodiment, the transmissions of the plane ultrasound beams to the scanning target may be inserted between the transmissions of the focused ultrasound beams to the scanning target. For example, the multiple transmissions of the focused ultrasound beam to the scanning target may be evenly inserted into the process of step S102 above.

For example, the transmission sequence "Ai Bi Ci" mentioned above may be mainly used to obtain the data used for calculating the flow velocity information or the flow velocity vector information, and the transmissions of another kind of ultrasound beams used to obtain the data used for reconstructing the ultrasound images may be inserted between the transmission sequence "Ai Bi Ci" mentioned above. Taking inserting multiple transmissions of focused ultrasound beams to the scanning target between the transmission sequence "Ai Bi Ci" mentioned above as an example, the method for transmitting alternately two kinds of ultrasound beams will be described in detail below.

The plane ultrasound beams may be transmitted to the scanning target respectively in three ultrasound propagation directions in the following order:

A1 B1 C1 D1A2 B2 C2 D2 A3 B3 C3 D3 . . . Ai Bi Ci Di, and so on.

Where Ai may be the ith transmission in a first ultrasound propagation direction, Bi may be the ith transmission in a second ultrasound propagation direction, Ci may be the ith transmission in a third ultrasound propagation direction, and Di may be the ith transmission of the focused ultrasound beam.

In the embodiment above, a relatively simple transmission method in which the transmissions of the focused ultrasound beams are inserted may be provided. Alternatively, it may also be possible that one transmission of the focused ultrasound beam is inserted after the multiple transmissions of the plane ultrasound beams in all of the ultrasound propagation directions are completed; or, at least a part of the multiple transmissions of the plane ultrasound beams to the scanning target and at least a part of the multiple transmissions of the focused ultrasound beams to the scanning target may be performed alternately; etc. Alternatively, any method which can achieve the alternate transmitting of at least a part of the multiple transmissions of the plane ultrasound beams to the scanning target and at least a part of the multiple transmissions of the focused ultrasound beams to the scanning target may be used. In the present embodiment, the focused ultrasound beams may be used to obtain the ultrasound images with better quality, while the plane ultrasound beams with high frame rate may be used to obtain the velocity vector information with high real-time. Furthermore, two kinds of ultrasound beams may be transmitted alternately so as to the data acquisition of the two kinds of ultrasound beams may have better synchronization.

Therefore, the order and rules of the multiple transmissions of the ultrasound beams to the scanning target in the ultrasound propagation directions may be selected arbitrarily and will not be listed one by one herein, but will not be limited to the specific embodiments described above.

In step S200, the receiving circuit 4 and the beam-forming unit 5 may receive the echoes of the ultrasound beams transmitted in step S100 above to obtain the ultrasound echo signals. For example, as shown in FIG. 8, in step S221, the echoes of the focused ultrasound beams may be received to obtain the focused ultrasound echo signals; in step S242, the echoes of the plane ultrasound beams may be received to obtain the plane ultrasound echo signals; and so on.

When the receiving circuit 4 and the beam-forming unit 5 receive the echoes of the ultrasound beams transmitted in step S100 above, each or each part of the transducers used in the transmission of the ultrasound beams may be used to receive the echoes in time-sharing with the transmission of the ultrasound beams. Alternatively, the transducers in the probe may be divided into receiving part and transmitting part, and each or each part of the transducers in the receiving part may be used to receive the echoes of the ultrasound beams transmitted in step S100 above. The receiving of echoes of the ultrasound beams and the obtaining of the ultrasound echo signals may be similar to those well known in the art.

In step S100, the ultrasound beams may be transmitted in each ultrasound propagation direction, and correspondingly, in step S200, the echoes of the ultrasound beams may be received to obtain a group of ultrasound echo signals. For example, in the embodiment shown in FIG. 9, in step S241, the echoes of the ultrasound beams transmitted to the scanning target in an ultrasound propagation direction may be received to obtain a group of ultrasound echo signals, and correspondingly, in step S300, step S341 as shown in FIG. 9 may be performed to obtain the ultrasound images of at least a part of the scanning target based on the group of ultrasound echo signals; while in the embodiment shown in FIG. 10, in step S251, the echoes of the ultrasound beams transmitted to the scanning target in multiple ultrasound propagation directions may be received to obtain multiple groups of ultrasound echo signals, where each of the groups of ultrasound echo signals may be derived from the echoes of the ultrasound beams transmitted in one ultrasound propagation direction, and correspondingly, in step 300, step S351 as shown in FIG. 10 may be performed to obtain the ultrasound images of at least a part of the scanning target based on one of the multiple groups of ultrasound echo signals.

In addition, the ultrasound beam may be transmitted in each ultrasound propagation direction for multiple times, and the group of ultrasound echo signals correspondingly obtained by receiving the echoes of the ultrasound beams in step S200 may include multiple ultrasound echo signals, where one ultrasound echo signals may be obtained by transmitting the ultrasound beam for one time.

For example, as shown in FIG. 10, in step S151, the plane ultrasound beam may be transmitted to the scanning target respectively in multiple ultrasound propagation directions for multiple times, and in step S200, step S251 may be performed to respectively receive the echoes of the plane ultrasound beams corresponding to the multiple ultrasound propagation directions to obtain multiple groups of plane ultrasound echo signals, where each group of plane ultrasound echo signals may include at least two plane ultrasound echo signal each of which may be derived from the echoes obtained by transmitting the ultrasound beam to the scanning target in one ultrasound propagation direction for one time.

Alternatively, in the case that the focused ultrasound beam are transmitted to the scanning target for multiple times in step S100, the echoes of the focused ultrasound beams may be received in step S200 to obtain multiple groups of focused ultrasound echo signals.

Therefore, the kind of the ultrasound beam transmitted in step S100 may correspond to the kind of the echoes of the ultrasound beams and the kind of ultrasound echo signal generated thereby. For example, the focused ultrasound beams correspond to the focused ultrasound echo signal, the plane ultrasound beams correspond to the plane ultrasound echo signal, the diffused ultrasound beams correspond to the diffused ultrasound echo signal, and so on.

In step S300, the image processing unit 7 may obtain the ultrasound images of at least a part of the scanning target based on the ultrasound echo signals. The ultrasound images herein may be three-dimensional ultrasound images or two-dimensional ultrasound images, such as B mode images, the image of the three-dimensional ultrasound image database obtained by the scanning bodies described above or enhanced B mode images obtained by two-dimensional flow imaging.

In one embodiment, the ultrasound images may be obtained using the plane ultrasound beams or using the focused ultrasound beams. Since the energy of the focused ultrasound beam is concentrated and the imaging is performed at the energy concentration location, the echo signals obtained thereby have high signal-to-noise ratio and the obtained ultrasound images have better quality. Furthermore, since the focused ultrasound beams have narrow main lobe and low side lobes, the obtained ultrasound images have higher lateral resolution. Therefore, in one embodiment, in step S500, the ultrasound images may be obtained using the focused ultrasound beams. Furthermore, in order to obtain ultrasound images with better quality, the focused ultrasound beams may be transmitted for multiple times in step S100 to obtain one frame of ultrasound image.

In one embodiment, the focused ultrasound beam may be transmitted to the scanning target for multiple times in step S100, and the echoes of the focused ultrasound beams may be received to obtain a group of focused ultrasound echo signals in step S200. As shown in FIG. 8, in step S300 above, step S321 may be performed to obtain the ultrasound images of at least a part of the scanning target based on the focused ultrasound echo signals. With the focused ultrasound beams, the ultrasound images with better quality may be obtained. The combination of the transmissions of the plane ultrasound beams and the focused ultrasound beams may be similar to the description above.

In step S400, the image processing unit 7 may respectively obtain the Doppler flow velocity information and the flow velocity vector information of the target points in the scanning target based on the ultrasound echo signals obtained in step S200. The flow velocity vector information mentioned herein may at least include the flow velocity vector (i.e., the magnitude and direction of the flow velocity) of the target points, and may also include the location information of the target points in the ultrasound images. Alternatively, the flow velocity vector information may also include any other information related to the velocity of the target point obtained according to the magnitude and direction of the flow velocity, such as acceleration information or the like.

Figure 11:
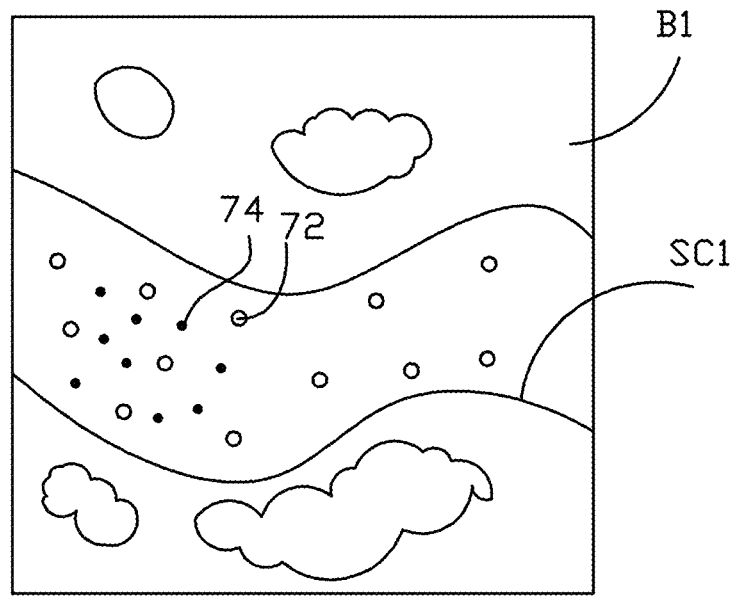
FIG. 11 schematically shows the selectable target points in an embodiment.

In the present embodiment, the target point may be point or location of interest in the scanning target, which may usually be the point or location of interest that can be marked or represented in the image of at least a part of the scanning target shown in the display. For example, as shown in FIG. 11, the scanning target SC1 may be a blood vessel within a human body. In one embodiment, the target points mentioned above may include one or more discrete locations within the scanning target. Alternatively, the target points mentioned above may include the neighborhood or data block of one or more discrete locations. For example, the circles or dots in FIG. 11 may be the target points.

For example, in one embodiment, in step S400, distribution density instructions inputted by the user may be obtained. The target points may be randomly selected in the scanning target according to the distribution density instructions, and the flow velocity vector information corresponding to the selected target points may be calculated, thereby obtaining the flow velocity vector information of the selected target points. The obtained flow velocity vector information may be marked on the background images for displaying on the display. For example, in the scanning target SC1 on the background image B1 in FIG. 11, the user may input the distribution density of the target points to be set within the scanning target SC1 through human-machine interaction device. In FIG. 11, the dots 74 and the circles 72 may represent the selected target points, of which the distribution densities are different. The distribution density herein may be understood as the likelihood that the target point will appear within a certain area. The certain area may be the entire area of the scanning target SC1 in the background image B1, and alternatively may also be the part of the area of the scanning target SC1. For example, in FIG. 11, the target points are located in the front end area of the scanning target SC1 in the flow direction, i.e., the dots 74 are located in the front end area of the scanning target SC1.

Thereafter, the flow velocity vectors corresponding to the selected target points may be calculated to obtain the flow velocity vector information of the selected target points. The obtained flow velocity vector information may be marked on the background image for displaying on the display.

In the present embodiment, the background image may usually be ultrasound image. However, with reference to the embodiments shown in FIG. 22 to FIG. 25, the background image may also be Doppler color flow images, and with reference to the embodiments shown in FIG. 28 to FIG. 30, the background image may also be enhanced B mode image. Therefore, the background image may be understood as the basic image on which the flow velocity vector information will be superimposed when the flow velocity vector information is displayed. In the present disclosure, the background image will be determined according to the display mode of the system and shall not be limited to the ultrasound image.

For example, in one embodiment, step S400 may further include:

obtaining location indicating instructions inputted by the user, obtaining the selected target points according to the location indicating instructions, and calculating the flow velocity vector information corresponding to the selected target points to obtain the flow velocity vector information of the selected target points. The obtained flow velocity vector information may be marked on the background image for displaying on the display. For example, in FIG. 12, the user may input the location indicating instructions in the scanning target SC1 by controlling the location of the cursor 71 in the scanning target SC1 on the background image B1 through the human-machine interaction device, thereby selecting the location of the target point on the background image, such as the dots 73 in FIG. 12.

In the present embodiment, the target points may be selected by the user, and the two specific embodiments above provide two ways for selecting the target points. However, the present disclosure will not be limited thereto. In this way, the user can flexibly select the target points, thereby increasing the use experience.

In step S400, the flow velocity vector information of the target points in the scanning target may be obtained based on the ultrasound echo signals, which will be described in detail below.

The flow velocity vector information of the target points obtained in step S400 may mainly be used to be displayed together with the Doppler color flow images in step S600 below. Therefore, based on the display mode of the flow velocity vector information, different flow velocity vector information may be obtained in step S400.

Figure 13A:
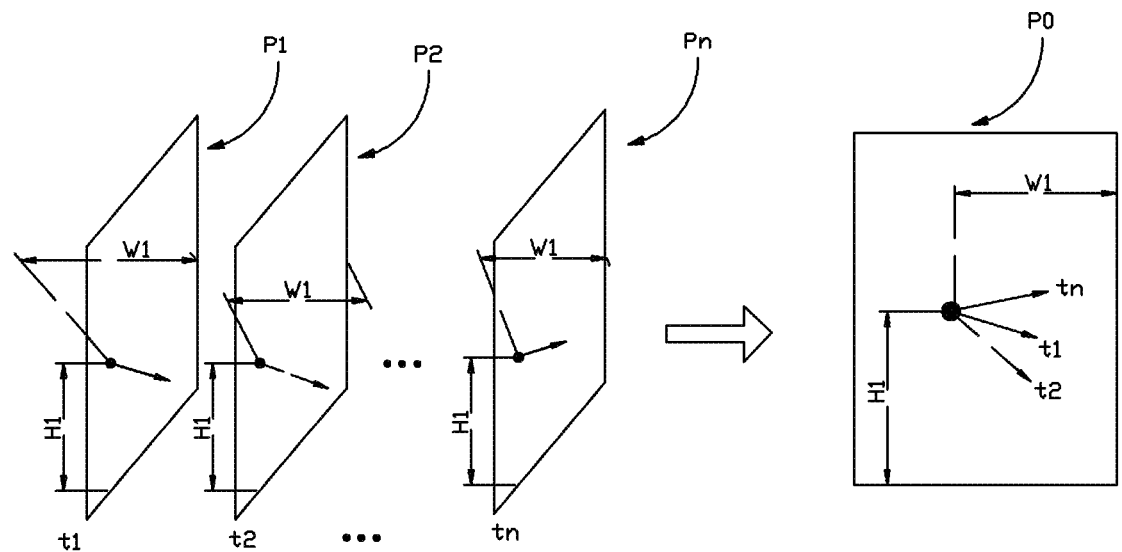
FIG. 13A schematically shows the calculation of the flow velocity vector information in the first mode in an embodiment.

For example, in one embodiment, step S400 may include calculating the flow velocity vectors of the target point when the target point is located at a first position in the ultrasound images at different times to obtain the flow velocity vector information of the target point in the ultrasound images at different times. In step S600, what is comparatively displayed may be the flow velocity vector information at the first position in the ultrasound images at different times. As shown in FIG. 13A, the ultrasound image data P1, P2 displayed may be the flow velocity vector information at the first position in the ultrasound images at different times. A then the flow velocity vectors of the target points at the first position (such as the position represented by the black dot in the figure) in the ultrasound images at these times. In the present embodiment, the first position of the target point in the ultrasound images at those times may be at the position (H1, W1) in the two-dimensional image. Based on this, in subsequent step S700, when the flow velocity vector information is comparatively displayed, the calculated flow velocity vectors corresponding to different times may be displayed at the position (H1, W1) in the ultrasound image P0 displayed on the display. In the case that a part, or all, of the target points are selected by the user as described in the embodiments above, or selected by the system, the corresponding first position may be correspondingly obtained, and the flow velocity vector information at the first position in the ultrasound image at the current time may be calculated for displaying. In the present disclosure, this display mode may be referred to as a first mode. FIG. 13A schematically shows the flow velocity vector information in a two-dimensional image P0. However, the flow velocity vector information may also be displayed in a three-dimensional image, i.e., the ultrasound images at those times may be three-dimensional images mentioned above and the first position may be a spatial position in the three-dimensional images, which will not be described again.

In one embodiment, in step S400, the flow velocity vectors at the positions to which the target point is successively moved in the ultrasound images may be calculated according to the ultrasound echo signal obtained in step S200, thereby obtaining the flow velocity vector information of the target point. In the present embodiment, the flow velocity vectors of the target point when the target point is successively moved from an initial position to the corresponding positions in the ultrasound images may be obtained by repeatedly calculating the flow velocity vector of the target point when the target point is moved from one position to another position in the ultrasound images in a time interval. In other words, the position in the ultrasound image used for the calculation of the flow velocity vector may be obtained by calculation. In subsequent step S600, what are comparatively displayed may be the flow velocity vector information at the positions obtained by calculation in the ultrasound images at those times.

Figure 13B:
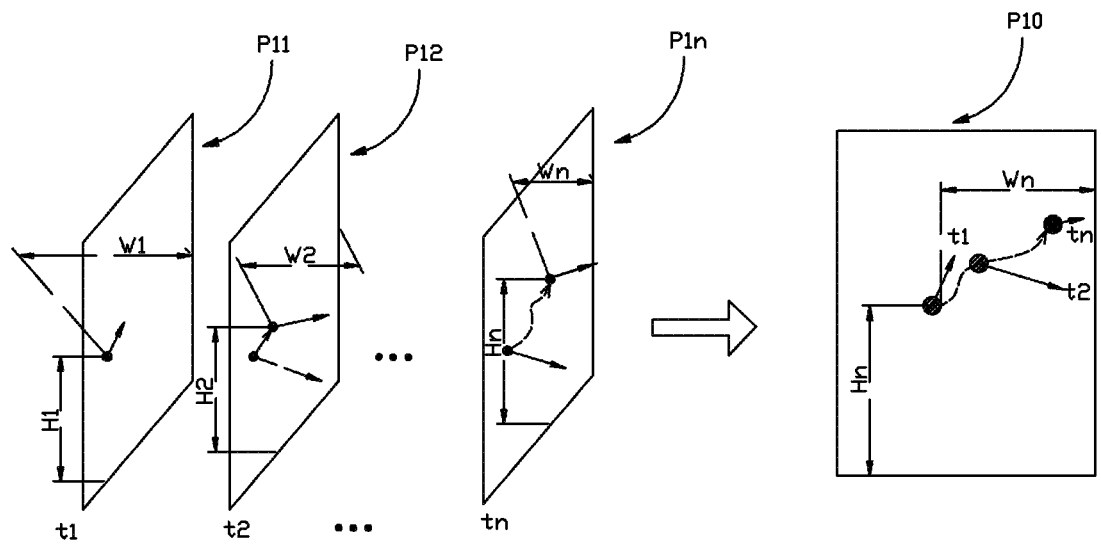
FIG. 13B schematically shows the calculation of the flow velocity vector information in the second mode in an embodiment.

As shown in FIG. 13B, the ultrasound image data P11, P12 . . . P1n at the times t1, t2 . . . to may be respectively obtained according to the ultrasound echo signals obtained in step S200. Thereafter, the initial position of the target point may be determined according to the part, or all, of the target points selected by the user or the density of the target points set by the system as described in the embodiments above. For example, the first point with coordinates (H1, W1) in FIG. 13B may be the initial position. Next, the flow velocity vector A1 at the initial position in the ultrasound image P11 at time t1 may be calculated. Thereafter, the position (H2, W2) in the ultrasound image P12 at time t2 to which the target point (such as the black dot in the figure) is moved from the initial position in the ultrasound image P11 may be calculated, and the flow velocity vector at the position (H2, W2) in the ultrasound image P12 may be obtained according to the ultrasound echo signals for displaying. For example, the displacement of the target point at the second time t2 in the direction of the flow velocity vector at the position (H1, W1) in the ultrasound image P11 at time t1 during a time interval (where the time interval=time t2−time t1) may be calculated, thereby obtaining a second position of one target point at the first time t1 in the ultrasound image at the second time. Next, the flow velocity vector at the second position may be obtained according to the ultrasound echo signals obtained in step S200, thereby obtaining the flow velocity vector information of the target point in the ultrasound image at the time t2, and so on. For two adjacent times, the displacement of the target point in the direction of the flow velocity vector corresponding to the first time during the time interval between the two times may be obtained, the corresponding position of the target point in the ultrasound image at the second time may be determined according to the displacement, and the flow velocity vector at the corresponding position to which the target point is moved from the first time to the second time may be obtained according to the ultrasound echo signals. This way, the flow velocity vector information when the target point is successively moved from position (H1, W1) to position (Hn, Wn) in the ultrasound images may be obtained, thereby obtaining the flow velocity vectors of the target point when the target point is successively moved from the initial position to corresponding positions in the ultrasound images at different times. Thereby, the flow velocity vector information of the target point may be obtained and displayed together with the Doppler color flow images.

Figure 12:
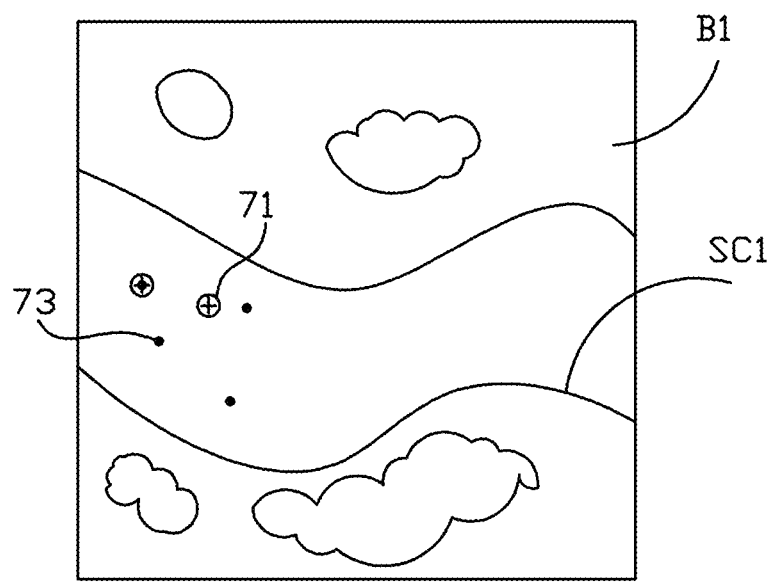
FIG. 12 schematically shows the selectable target points in an embodiment.

In the present embodiment, the displacement of the target point during a time interval may be calculated and the corresponding position of the target point in the ultrasound images may be determined based on such displacement. The target point may be moved starting from the initial position according to the time interval. The time interval may be determined based on the transmission frequency of the system or based on the display frame rate. Alternatively, the time interval may also be inputted by the user. The position to which the target point is moved may be calculated according to the time interval inputted by the user, and the flow velocity vector information at such position may be obtained for display. Initially, N initial target points may be selected in the image using the methods as shown in FIG. 11 and FIG. 12 above, and each initial target point may have arrow which represents the magnitude and direction of the velocity at this point, as shown in FIG. 13B. In step S600, the flow velocity vectors at the corresponding positions to which the target point is successively moved may be displayed to form flowing marks which flow over time. By displaying the flow velocity vector information obtained using the methods as shown in FIG. 13B, as time changes, the location of the arrow at each point in the subsequent image will change. Thereby, a flowing mark which can represent the flowing of the flow may be obtained by the movement of the arrow, such that the user can observe flowing flow similar to real blood flow. In the present disclosure, this display mode may be referred to as a second mode. FIG. 13B schematically shows the flow velocity vector information in a two-dimensional image P10. However, the flow velocity vector information may also be displayed in a three-dimensional image, i.e., the ultrasound images at those times may be three-dimensional images mentioned above and the first position may be a spatial position in the three-dimensional images, which will not be described again.

In the embodiments above, based on a part, or all, of the target points selected by the user or the ultrasound imaging system and the type of the transmission of the ultrasound beam mentioned in step S100 above, the flow velocity vector at the target point in the scanning target in the ultrasound image at a certain time may be obtained based on the ultrasound echo signals using a variety of methods as below.

FIG. 9 schematically shows the first method. In step S441, the flow velocity vector information of the target point in the scanning target may be calculated using one group of ultrasound echo signals obtained by transmitting the ultrasound beams in one ultrasound propagation direction in step S141. In this process, the flow velocity vector of the target point at the corresponding position in the ultrasound image may be obtained by calculating the magnitude and direction of the displacement of the target point within the preset time interval.

As mentioned above, the flow velocity vector information of the target point may be calculated using the plane ultrasound echo signals. Therefore, in one embodiment, the magnitude and direction of the displacement of the target point in the scanning target within the preset time interval may be calculated using one group of plane ultrasound echo signals.

In the present embodiment, the methods for calculating the flow velocity vector of the target point at the corresponding position in the ultrasound image may be the methods similar to speckle tracking methods. Alternatively, the Doppler ultrasound imaging methods may be used to obtain the flow velocity vector of the target point in an ultrasound propagation direction. Alternatively, the time gradient and the spatial gradient at the target point may be used to obtain the component of the velocity vector of the target point. Other methods may also be used.

For example, in one embodiment, obtaining the flow velocity vector of the target point in the scanning target at a certain position in the ultrasound image using the ultrasound echo signals may include the steps below.

First, at least two frames of image data may be obtained based on the ultrasound echo signals obtained as described above. For example, at least a first frame of image data and a second frame of image data may be obtained. As mentioned above, in the present embodiment, the plane ultrasound beams may be used to obtain the image data used for calculating the flow velocity vectors of the target point. Since the plane ultrasound beams propagate substantially in entire imaging region, generally one frame of plane beam echo image data may be obtained by processing the one plane beam echo signals obtained by transmitting the plane ultrasound beam for one time. In the present disclosure, the ultrasound image data of the scanning target obtained by processing the plane beam echo signals of the plane ultrasound beams may be referred to as "plane beam echo image data".

Next, a tracking region may be selected in the first frame of image data. The tracking region may contain the target point of which the velocity vector is desired to be obtained. For example, the tracking region may be a neighborhood of the target point or a data block containing the target point.

Thereafter, a region corresponding to the tracking region may be searched in the second frame of image data. For example, a region which has maximum similarity with the tracking region may be searched out as the tracking result region. In the present disclosure, the common methods for measuring similarity in the art may be used to measure the similarity.

Finally, the velocity vector of the target point may be calculated based on the locations of the tracking region and the tracking result region and the time interval between the first frame of image data and the second frame of image data. For example, the magnitude of the flow velocity vector may be obtained by dividing the distance (i.e., the displacement of the target point within the preset time interval) between the tracking region and the tracking result region by the time interval between the first frame of plane beam echo image data and the second frame of plane beam echo image data, and the direction of the flow velocity vector may be the direction from the tracking region to the tracking result region, i.e., the direction of the movement of the target point in the preset time interval.

In one embodiment, the method for obtaining the velocity vectors of the target point based on the time gradients and the spatial gradients at the target point may include following steps.

First, at least two frames of ultrasound image data may be obtained according to the ultrasound echo signals.

Next, a first gradient in the time direction at the target point may be obtained according to the ultrasound image data, a second gradient in the ultrasound propagation direction at the target point may be obtained according to the ultrasound image data, and a third gradient in the direction perpendicular to the ultrasound propagation direction at the target point may be obtained according to the ultrasound image data. Thereafter, a fifth velocity component in the ultrasound propagation direction and a sixth velocity component in the direction perpendicular to the ultrasound propagation direction of the target point may be calculated using the first gradient, the second gradient and the third gradient.

Thereafter, the velocity vector of the target point may be synthesized using the fifth velocity component and the sixth velocity component.

In one embodiment, the Doppler ultrasound imaging methods may be used to obtain the flow velocity vectors of the target point, which will be described below.

In the Doppler ultrasound imaging methods, the ultrasound beams may be successively transmitted to the scanning target in one ultrasound propagation direction for multiple times. The echoes of the ultrasound beams transmitted for multiple times may be received to obtain multiple ultrasound echo signals, where each vale of each ultrasound echo signal may be the value of one target point to be obtained by scanning in one ultrasound propagation direction. The step S400 may include the following steps.

First, the Hilbert transform may be performed on the multiple ultrasound echo signals respectively in the ultrasound propagation direction, thereby obtaining multiple groups of image data which represents the value at each target point in complex number. Therefore, after transmitting and receiving for N times, N complex numbers which change over time may be obtained at each target point. Thereafter, the magnitude of the velocity in the ultrasound propagation direction of a target point z may be calculated using the following two formulas:

$$V_z = -\frac{c}{4\pi f_0 T_{prf}} \arctan\left(\frac{\Im\{R(1)\}}{\Re\{R(1)\}}\right) \quad \text{Formula (1)}$$

$$R(1) = \frac{1}{N-1}\sum_{i=0}^{N-2} x(i)x(i+1) + y(i)y(i+1) + j[y(i+1)x(i) - x(i+1)y(i)] \quad \text{Formula (2)}$$

where Vz is the calculated velocity value in the ultrasound propagation direction, c is the velocity of sound, f0 is the center frequency of the probe, Tprf is the time interval between two transmission, N is the number of the transmission, x(i) is the real part obtained by the ith transmission, y(i) is the imaginary part obtained by the ith transmission, $\Im$ is the operator for taking the imaginary part, and $\Re$ is the operator for taking the real part. The formulas above may be used to calculate the flow velocity at a fixed location.

Similarly, the magnitude of the flow velocity vector at each target point may be calculated based on the N complex numbers.

The direction of the flow velocity vector may be the ultrasound propagation direction, i.e., the ultrasound propagation direction corresponding to the multiple ultrasound echo signals.

Generally, in ultrasound imaging, the velocity of the scanning target or the moving part within the scanning target may be obtained by performing Doppler processing on the ultrasound echo signals based on the Doppler principle. For example, after the ultrasound echo signals are obtained, the velocity of the scanning target or the moving part within the scanning target may be obtained according to the ultrasound echo signals by autocorrelation estimation or cross correlation estimation. The methods for performing the Doppler processing on the ultrasound echo signals to obtain the velocity of the scanning target or the moving part within the scanning target may be any method being used now or to be used in the future in the art by which the velocity of the scanning target or the moving part within the scanning target may be calculated using the ultrasound echo signals, and will not be described in detail herein.

Of course, in the present disclosure, the methods for processing the ultrasound echo signals in an ultrasound propagation direction will not be limited to the two methods above. Other methods which are known or will be used in the future in the art may also be used. The ultrasound image data mentioned in the present disclosure may be two dimensional image data, or may also be three dimensional image data formed by multiple two dimensional image data.

FIG. 10 schematically shows the second method. In step S451, the flow velocity vector information of the target point within the scanning target may be calculated according to the multiple groups of ultrasound echo signals obtained by transmitting the ultrasound beams in multiple ultrasound propagation directions in step S151. During this process, first, one flow velocity vector component of the target point within the scanning target at the corresponding position in the ultrasound image may be calculated based on one group of ultrasound echo signals of the multiple groups of ultrasound echo signals, thereby multiple velocity vector components at the corresponding position being obtained according to the multiple groups of ultrasound echo signals. Thereafter, the flow velocity vector of the target point at the corresponding position in the ultrasound image may be synthesized using the multiple flow velocity vector components.

As mentioned above, the plane ultrasound echo signals may be used to calculate the flow velocity vector of the target point. Therefore, in one embodiment, one flow velocity vector component of the target point within the scanning target at one position may be calculated based on one group of plane ultrasound echo signals of multiple groups of plane ultrasound echo signals, thereby obtaining multiple flow velocity vector components at the position according to the multiple groups of plane ultrasound echo signals.

In the present embodiment, the first method described above may be used to calculate one flow velocity vector component of the target point within the scanning target based on one group of ultrasound echo signals of multiple groups of ultrasound echo signals. For example, the flow velocity vector component of the target point at the corresponding position may be obtained by calculating the displacement and direction of the movement of the target point in the preset time interval according to one group of ultrasound echo signals. In the present embodiment, the methods for calculating the velocity vector component of the target point may be speckle tracking methods; alternatively, the Doppler ultrasound imaging methods may also be used to obtain the velocity vector component of the target in an ultrasound propagation direction; alternatively, the flow velocity vector component of the target point may also be obtained based on the time gradients and the spatial gradients at the target point; and so on. The details of these methods may refer to the detailed description with respect to the first method above and will not be described again.

Figure 14A:
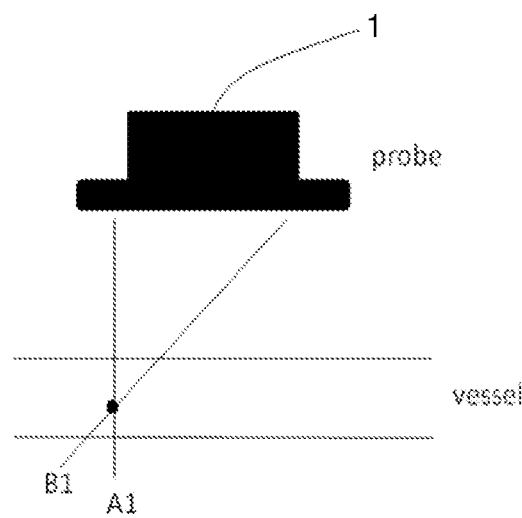
FIG. 14A schematically shows the transmission in two ultrasound propagation directions in an embodiment.
Figure 14B:
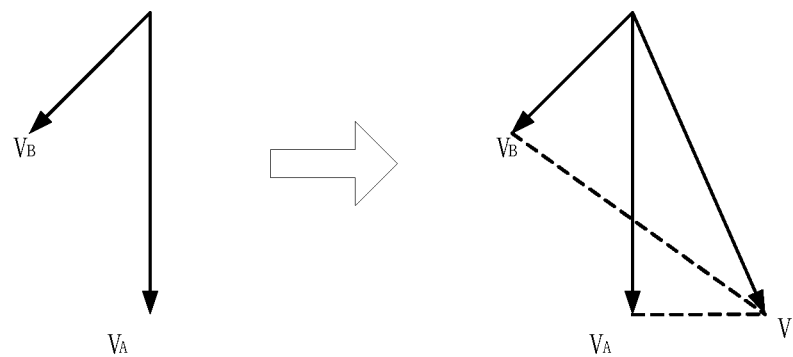
FIG. 14B schematically shows the synthesis of the flow velocity vectors shown in FIG. 14A.

In the case that there are two angles in step S151 in FIG. 10, the magnitudes and directions of the flow velocities at all positions desired to be measured at one time may be obtained by 2N transmissions; in the case that there are three angles, 3N transmissions may be needed; and so on. FIG. 14A shows two transmissions A1 and B1 in different angles, in which the magnitude and direction of the velocity at the dot may be calculated by velocity synthesis. The velocity synthesis may be shown in FIG. 14B. In FIG. 14B, VA and VB may respectively be the flow velocity vector component of the target point at the corresponding position in the ultrasound propagation directions A1 and B1 shown in FIG. 14A. In the case that there are two ultrasound propagation directions, the image data obtained by each transmission may be repeatedly used to calculate the flow velocity vector component using the Doppler imaging methods, thereby reducing the time interval between obtaining the magnitudes and directions of the velocities in the whole field for two times. The minimum time interval in case of two ultrasound propagation directions may be the time used for two transmissions, the minimum time interval in case of three ultrasound propagation directions may be the time used for three transmissions, and so on. With the methods above, the magnitudes and directions of the velocities at all positions in the whole field may be obtained at each moment.

In the case that there are at least three ultrasound propagation directions in step S151 in FIG. 10, the at least three ultrasound propagation directions corresponding to the at least three groups of echo signals used for calculating at least three flow velocity vector components may not be in the same plane such that the calculated flow velocity vector components may be more close to the real velocity vectors in real three dimensional space, which may be referred to as constraint condition with respect to ultrasound propagation direction below.

For example, in step S100 above, the ultrasound beams may be transmitted to the scanning target in N (3≤N) ultrasound propagation directions. In step S400, each time n flow velocity vector components may be used to calculate the flow velocity vector of the target point at the corresponding position, where 3≤n<N. In other words, in step S100, the ultrasound beams may be transmitted to the scanning target in at least three ultrasound propagation directions, where the adjacent at least three ultrasound propagation directions are not in the same plane. Then, in step S400, one flow velocity vector component of the target point in the scanning target may be calculated based on each one group of echo signals of the at least three groups of echo signals, thereby obtaining at least three flow velocity vector components of the target point at the corresponding positions corresponding to the at least three groups of echo signals received successively. The flow velocity vector of the target point at the corresponding position may be synthesized using the flow velocity vector components in the at least three ultrasound propagation directions.

Alternatively, in order to reduce the calculation and decrease the complexity of the scanning and the calculation, in step S100, the ultrasound beams may be transmitted to the scanning target in N (3≤N) ultrasound propagation directions, while in step S400, each time N flow velocity vector components may be used to calculate the flow velocity vector of the target point at the corresponding position. In other words, in step S100, the ultrasound beams may be transmitted to the scanning target in at least three ultrasound propagation directions, where the at least three ultrasound propagation directions may not be in the same plane. In step S400, one flow velocity vector component of the target point in the scanning target at the corresponding position may be calculated based on each one group of echo signals of the received at least three groups of echo signals, thereby obtaining the flow velocity vector components of the target point at the corresponding positions in all ultrasound propagation directions corresponding to the at least three groups of echo signals. The flow velocity vector of the target point at the corresponding position may be synthesized using the flow velocity vector components in the all ultrasound propagation directions.

In order to satisfy the constraint condition with respect to ultrasound propagation direction mentioned above, either r to satisfy the constraint condition with respect to ultrasound propagation direction mentioned above, be calcee ultrasound propagation directions being not in the same plane" may be achieved by adjusting the time delay between the transducers used in the transmission of the ultrasound beams, and/or driving the transducers used in the transmission of the ultrasound beams to steer to change the emission direction of the ultrasound waves, to achieve different ultrasound propagation directions. Driving the transducers used in the transmission of the ultrasound beams to steer to change the emission direction of the ultrasound waves may be achieved by, for example, providing each transducer with a mechanical drive control unit which may drive the transducer to deflect a preset angle such that there is a preset steered angle between the emission direction of the ultrasound wave and the normal line of the plane in which the transducers are arranged.

In one embodiment, selection items or selection buttons which may be selected by the user may be displayed on the display, by which the number of the ultrasound propagation directions selected by the user or the number of the flow velocity vector components used for synthesizing the flow velocity vector in step S400 above selected by the user may be obtained, thereby generating instruction information. Based on the instruction information, the number of the ultrasound propagation directions in step S100 may be adjusted and the number of the flow velocity vector components used for synthesizing the flow velocity vector in step S400 may be determined according to the number of the ultrasound propagation directions; alternatively, the number of the flow velocity vector components used for synthesizing the flow velocity vector of the target point at the corresponding position is step S400 may be adjusted; thereby providing the user with more comfortable experience and more flexible information extraction interface.

In step S400, the data processing unit may obtain the Doppler flow velocity information according to the ultrasound echo signals. For example, the Doppler flow imaging herein may be color Doppler flow imaging (CDFI) techniques. The color Doppler flow imaging may also be referred to as two-dimensional Doppler imaging, in which the signals obtained may be processed by phase detection, autocorrelation and color coding to obtain color images representing the flow velocity which may be display on the B mode image in a superimposed manner. The color Doppler flow imaging can show the flow intuitively, and show the distribution of the nature and velocity of the flow in heart or blood vessel more quickly and more intuitively then pulse wave Doppler imaging. It has unique advantages in displaying left-to-right shunt blood flow and valvular reflux blood flow. However, it is worse in quantitative analysis of blood flow than pulsed wave and continuous wave Doppler imaging. In one embodiment of the present disclosure, the Doppler flow velocity information may include the spectrum information of the flow, etc. The flow velocity may be calculated according to the formula (1) and (2) above. Of course, in the present embodiment, the Doppler flow velocity information may also be obtained using other Doppler flow imaging techniques, which will not be described here in detail.

In addition, the obtained Doppler flow velocity information may be derived from the echoes of one kind of the plane ultrasound beams, focused ultrasound beams and the diffused ultrasound beams transmitted in step S100 above. Alternatively, in another embodiment, the Doppler flow velocity information may be obtained according to a group of plane ultrasound echo signals obtained by transmitting the plane ultrasound beams in one angle.

As shown in FIG. 9, the Doppler flow velocity information may be obtained according to the group of ultrasound echo signals obtained in step S241 above. As shown in FIG. 10, the Doppler flow velocity information may be obtained according to one of the multiple groups of ultrasound echo signals obtained in step S251 above.

In step S500, the data process unit may superimpose the ultrasound image obtained in step S300 above and the Doppler flow velocity information obtained in step S400 above to form the Doppler color flow image, which may be displayed in the display. Taking the display of the color flow image as an example, the flow data may be pseudo-color coded by a color processor based on the direction of the flow and the magnitude of the velocity and then sent to the display for display, thereby obtaining displayed color Doppler flow image. The Doppler color flow images may also be obtained using techniques known in the art, which will not be described here in detail.

In step S600, the flow velocity vector information obtained in step S300 above and the Doppler color flow image obtained in step S600 above may be displayed on the display.

In order to better display the flow velocity vector information and the Doppler color flow image, in one embodiment, the ultrasound image obtained in step S300 and the flow velocity vector information obtained in step S400 may be superimposed to form the vector flow image, and the vector flow image and the Doppler color flow image may be comparatively displayed, thereby implementing the comparative display of the Doppler information and the vector flow image and clearly showing the details of the vector flow information and the Doppler flow information. Superimposing the flow velocity vector information may include marking the flow velocity vector information on the background image thereby obtaining the marks shown on the display interface on the display 8.

With regard to the flow velocity vector information superimposed on the vector flow image, reference may also be made to the description with respect to S400 above.

Figure 15:
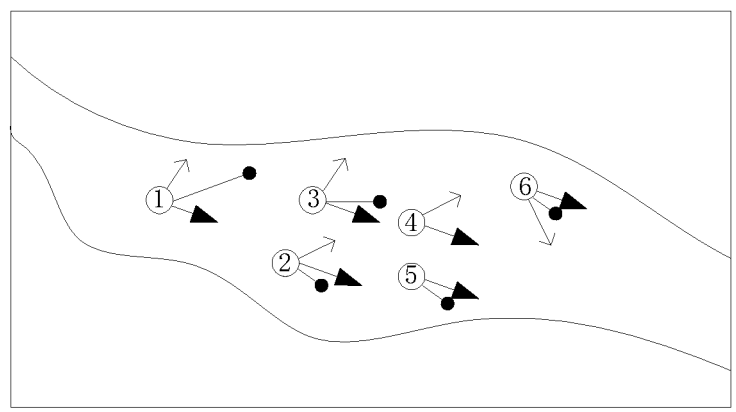
FIG. 15 schematically shows the display of the flow velocity vector information obtained in FIG. 13A.

For example, in step S400, the flow velocity vectors of the target point at the first position in the ultrasound images at different times may be calculated using the methods shown in FIG. 13A according to the ultrasound echo signals obtained in step S200, which may be superimposed on the ultrasound images to form the vector flow images. The vector flow images obtained in step S600 may be as shown in FIG. 15. In FIG. 15, the length of the arrows may represent the magnitude of the flow velocity vectors, and the direction of the arrows may represent the direction of the flow velocity vectors. In FIG. 15, the arrows ①②③④⑤⑥ elocity vectors. In FIG. 15, the arrows fined in step S200, which may be superimposed on the ultrasound images to form the vector flow images. The vector flow images obtained in step S600 may be as shown in FIG. 15. In FIG. 15, the length of the arrow direction of the velocities, and the length of the arrows may represent the magnitude of the velocities.

Figure 16:
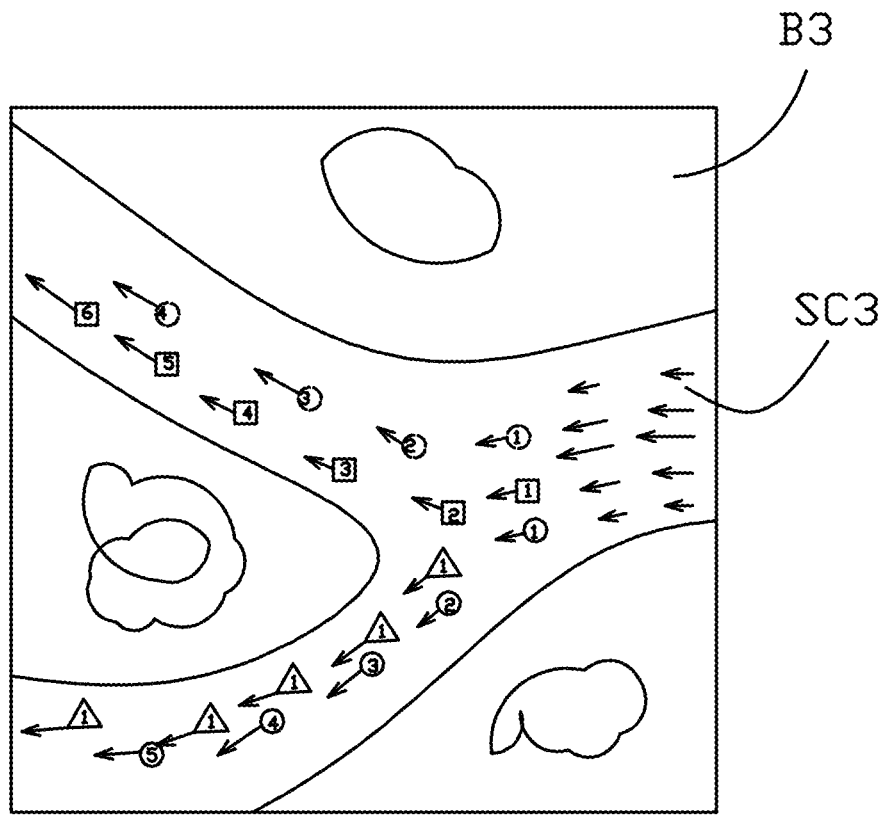
FIG. 16 schematically shows the display of the flow velocity vector information obtained in FIG. 13B.

As another example, in step S400, the flow velocity vectors at the positions to which the target point is successively moved in the ultrasound images may be calculated using the methods shown in FIG. 13B according to the ultrasound echo signal obtained in step S200, which may be superimposed on the ultrasound images to form the vector flow images as shown in FIG. 16. In step S600, by displaying the flow velocity vectors at the corresponding positions to which the target point is successively moved, a flowing mark flowing over time may be obtained. Such mark may be used to represent the flow velocity vector of the target point at the corresponding position in the ultrasound images. For example, an arrow may be used, where the direction of the arrow may represent the direction of the flow velocity vector at the corresponding position, and the length of the arrow may represent the magnitude of the flow velocity vector at the corresponding position. However, the present disclosure will not be limited to the arrows.

In FIG. 16, the scanning target SC3 in the ultrasound image B3 may be a carotid bifurcation, where the squares, the triangles, the circles and the dotted circles may respectively represent the target points and the number 1, 2, 3, 4 and 5, etc. may respectively represent the corresponding positions of the target points at different times. For example, the square with number 1 may represent the position of a first target point in the ultrasound image at time t1, the square with number 2 may represent the position of the first target point in the ultrasound image at time t2, the square with number 3 may represent the position of the first target point in the ultrasound image at time t3, . . . and so on. Therefore, the positions in the ultrasound image at different times to which the target point is successively moved may be shown. The direction of the arrows may represent the direction of the flow velocity vector at the positions, and the length of the arrows may represent the magnitude of the flow velocity vector at the positions. Similarly, the circles with numbers may respectively represent the positions of a second target point in the ultrasound images at time t1, t2 . . . etc.; the triangles with numbers may respectively represent the positions of a third target point in the ultrasound images at time t1, t2 . . . etc.; and the dotted circles with numbers may respectively represent the positions of a fourth target point in the ultrasound images at time t1, t2 . . . etc. As shown in FIG. 16, the display of the target point may present its flowing over time in the direction of the blood flow. Therefore, the displaying based on the flow velocity vector information obtained in step S400 may well present the real flow of the blood in the blood vessel, thereby providing more real blood flow status information for the user. FIG. 15 and FIG. 16 show the first mode and the second mode for displaying the flow velocity vectors, respectively.

Figure 28:
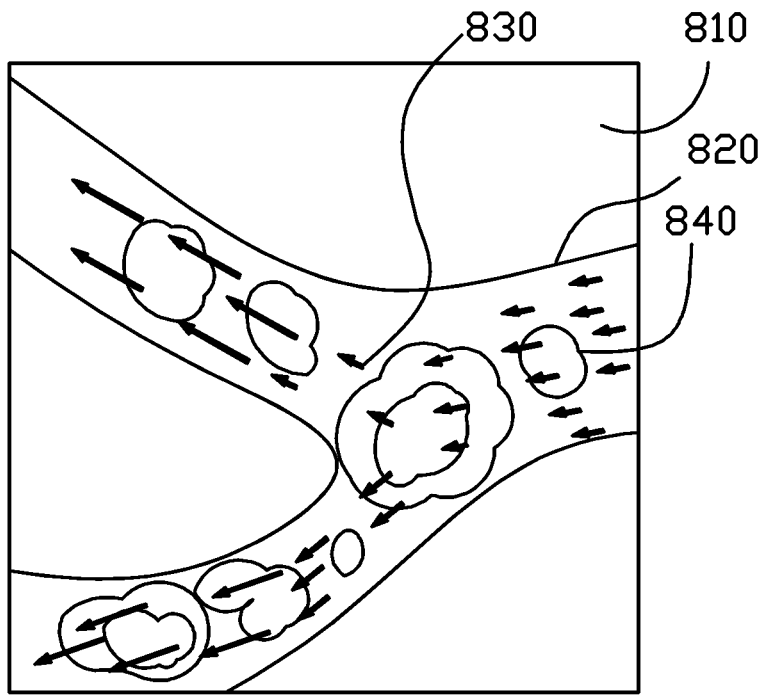
FIG. 28 schematically shows the cluster blocks in the enhanced B mode image in an embodiment.

In addition, the vector flow image may be obtained by superimposing the flow velocity vector information on ordinary ultrasound images, or by superimposing the flow velocity vector information on enhanced B mode images obtained by two dimensional flow imaging techniques. As shown in FIG. 28, after being processed by the two dimensional flow imaging techniques, the grayscale changes of the blood flow in the blood vessel region 820 on the enhanced B mode image 108 may be presented as clusters 840. The enhanced B mode image on which the flow velocity vector information 830 is superimposed is shown in FIG. 28. The clusters 840 may flow in the blood vessel region 820 over time, thereby acting as the background images of the flow velocity vector information 830.

Figure 29:
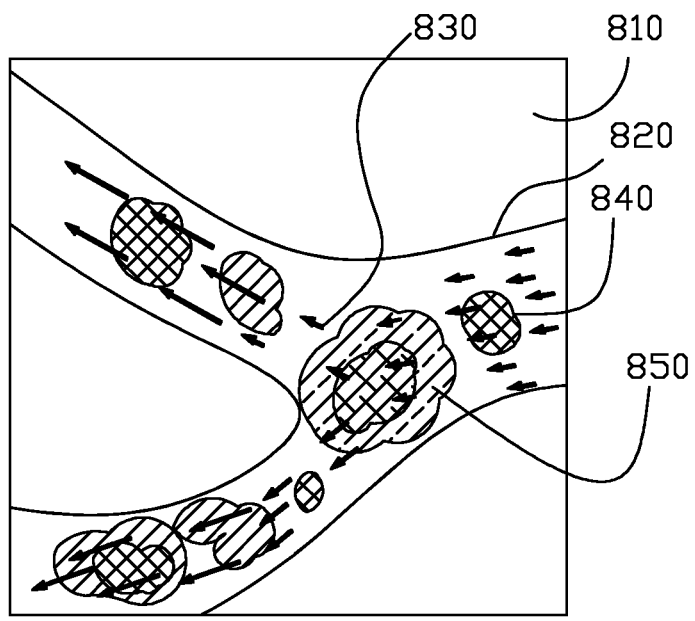
FIG. 29 schematically shows adding the color information on FIG. 28 in an embodiment.
Figure 30:
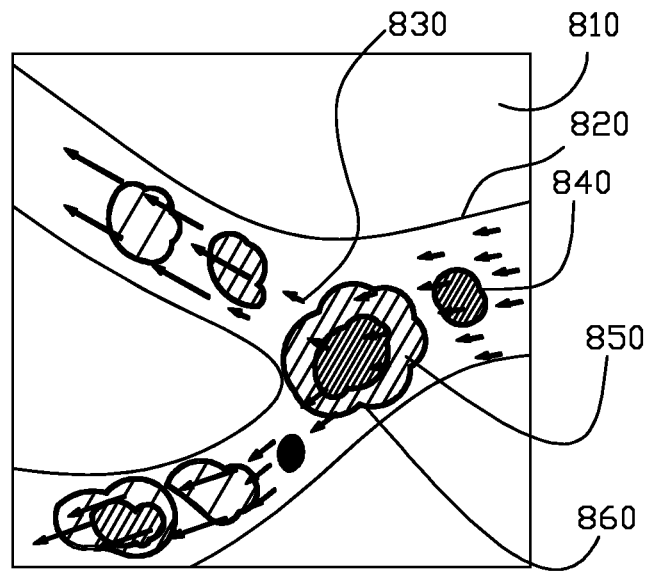
FIG. 30 schematically shows adding the color information on FIG. 28 in an embodiment.

In order to better comparatively display the flow velocity vector information and the ultrasound images to clearly show the grayscale changes in the blood vessel region in the ultrasound image, in one embodiment, colors may be added to the region of interest representing the flow region in the enhanced B mode image. For example, as shown in FIG. 29, in the blood vessel region 820 in the enhanced B mode image 810, the clusters 840 representing the grayscale changes may be filled with different colors. As shown in FIG. 29 and FIG. 30, the hatchings 850 with different types of line may be added to the clusters 840 to represent different color information. Besides representing the grayscale changes in the region of interest with different colors to obtain the color information mentioned above, one of the following steps A1 and A2 may be performed on the region of interest (e.g., the blood vessel region 820) representing the flow region in the enhanced B mode image to add the color information thereon.

Step A1: extracting the boundaries 860 of the cluster blocks in the region of interest based on the grayscale and marking the boundaries 860 with different colors. As shown in FIG. 30, the boundaries of the clusters 840 may be certain pixel areas. The pixel areas may be marked with different colors to distinguish the clusters with different gray average.

Step A2: extracting the cluster blocks 840 in the region of interest based on the image grayscale and filling the cluster blocks 840 with different colors, as shown in FIG. 29.

The steps A1 and A2 may be freely combined. For example, in FIG. 30, the color may be added on the boundaries 860 of the cluster blocks or be filled within the cluster blocks 840. The color may be obtained by adjusting any one of the hue (color), the saturation and the contrast, etc. For example, in one embodiment, the colors may be the same hue with different saturations.

In step S600, comparatively displaying the vector flow images and the Doppler color flow images may further include at least one of the following steps:
- switching between displaying the vector flow images individually on the display and displaying the Doppler color flow images individually on the display (hereinafter, "time-sharing display mode"); and
- simultaneously displaying the vector flow images and the Doppler color flow images (hereinafter, "simultaneous display mode").

In one embodiment, the time-sharing display mode and the simultaneous display mode may be freely switched between each other according to the mode switching instruction inputted by the user.

In the time-sharing display mode, the switching between individually displaying the vector flow images and individually displaying the Doppler color flow images may be achieved according to set switching frequency, set switching period, duration of individual display, or the switching instructions inputted by the user, etc. The individual display may refer to the display mode in which only one kind of images are displayed on the display in a certain time period.

Figure 17:
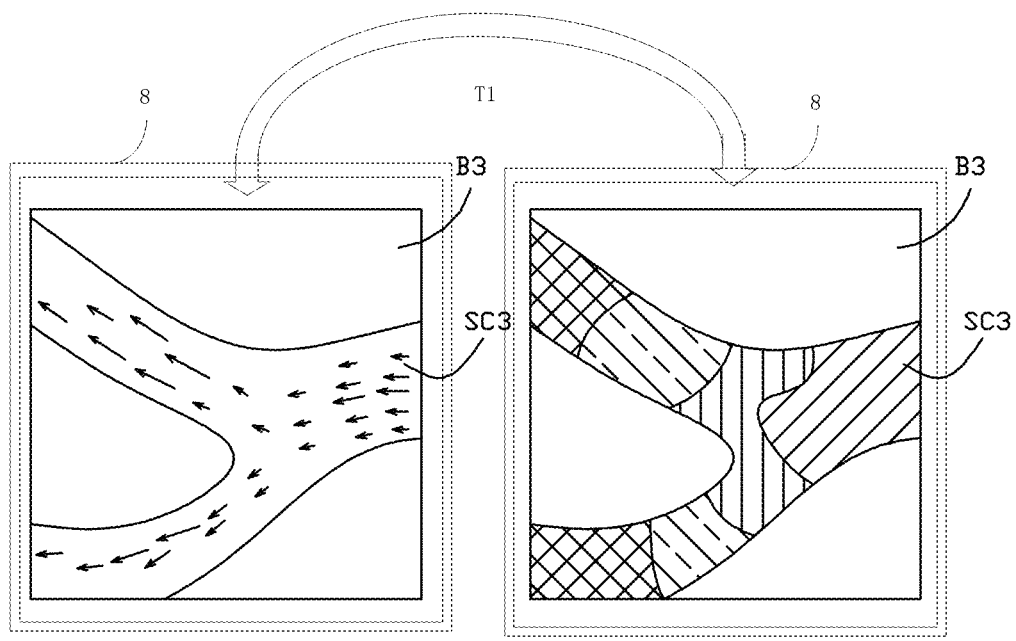
FIG. 17 schematically shows the time-sharing display mode in an embodiment.

For example, in one embodiment, as shown in FIG. 17, the switching period T1 may be set. When the time for the individual display reaches the switching period T1, the individual display of the vector flow images (the figure on the left) and the individual display of the Doppler color flow images (the figure on the right) will be switched between each other, and when not reaches the switching period T1, the current display mode will not be changed. In FIG. 17, the figure on the left shows the vector flow image, and the figure on the right shows the Doppler color flow image, both of which may be based on the ultrasound image B3 of the carotid bifurcation SC3. In the figure on the right, the different hatched areas in the Doppler color flow image may represent the Doppler flow velocity information displayed with different colors. In the figure on the left, the arrows in the vector flow image may be the marks used for marking the flow velocity vector information of the target points.

As another example, the user may input the switching instructions to switch between the individual display of the vector flow image and the individual display of the Doppler color flow image.

In another embodiment, the duration of the individual display mode may be set, which may be used to achieve the switching between the individual display of the vector flow image and the individual display of the Doppler color flow image. For example, a user interface, such as a window for inputting the set time, may be provided, in order to obtain the duration of the individual display of the vector flow image and the duration of the individual display of the Doppler color flow image inputted by the user. For example, the duration of the individual display of the vector flow image may be set as 1 minute, and the duration of the individual display of the Doppler color flow image may be set as 2 minutes. Thereafter, according to the durations, when the vector flow images have been individually displayed for the set duration, it will be switched into the individual display of the Doppler color flow image. When the Doppler color flow images have been individually displayed for the set duration, it will be switched into the individual display of the vector flow image. Therefore, the individual display of the vector flow image and the individual display of the Doppler color flow image may be freely switched between each other according to the needs of the user.

In these embodiments, the time-sharing display mode will not be limited to the three switching methods described above, and other switching methods which are not listed may also be used. Any method by which the individual display of the vector flow image and the individual display of the Doppler color flow image can be switched between each other according to pre-set time, switching frequency or other parameters are contemplated by the present disclosure.

The simultaneous display mode mentioned above may refer to the mode in which the vector flow image and the Doppler color flow image are simultaneously displayed in a same period.

For example, two displays may be used to respectively display the vector flow images and the Doppler color flow images. For example, two displays may be simultaneously connected to the output of the data processing unit to respectively receive the image data of the vector flow image and the Doppler color flow image for display.

Figure 18:
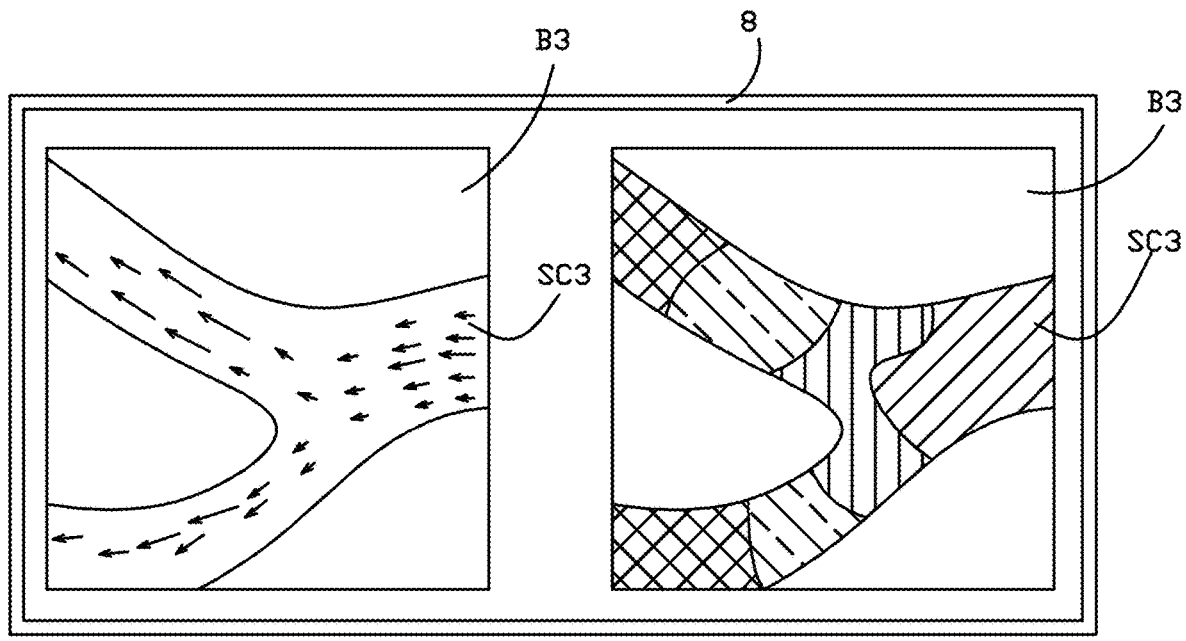
FIG. 18 schematically shows the simultaneous display mode in an embodiment.

In another embodiment, as shown in FIG. 18, the vector flow image and the Doppler color flow image may be simultaneously displayed in different windows on the same display interface on the display 8. In FIG. 18, the figure on the right represents the Doppler color flow image, and the figure on the left represents the vector flow image, both of which are located on the same displaying interface.

Figure 19:
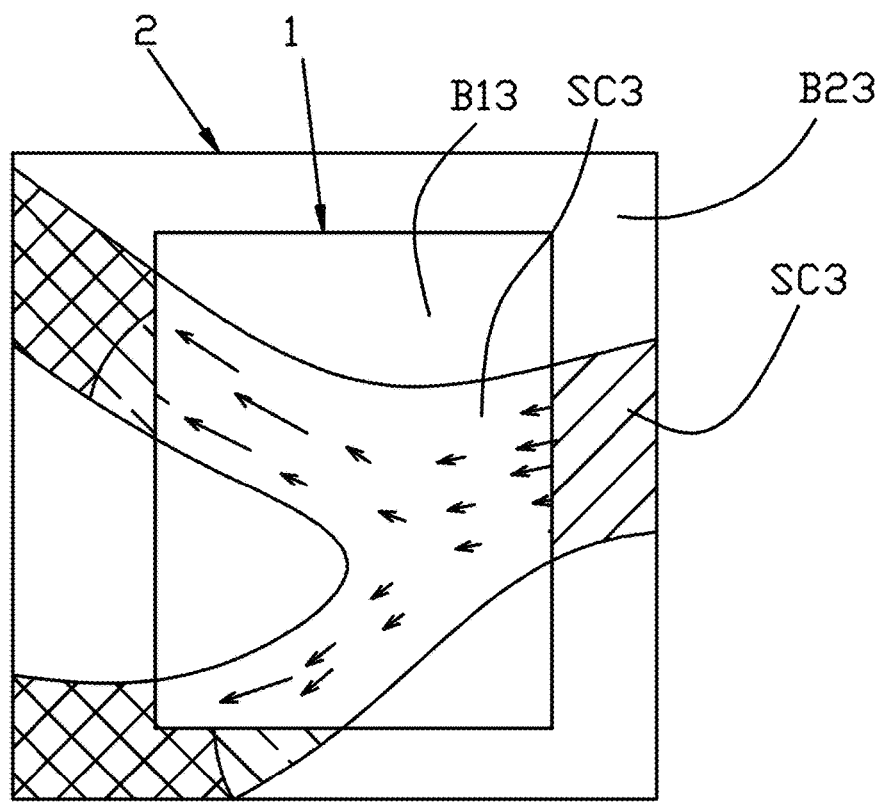
FIG. 19 schematically shows the simultaneous display mode in an embodiment.

In another embodiment, the vector flow image may be superimposed on the Doppler color flow image. As shown in FIG. 19, the Doppler color flow image 2 may be located at the bottom, and the vector flow image 1 may be located at the top. Both of them may be obtained based on the ultrasound image B3 of the carotid bifurcation SC3. The Doppler flow velocity information may be superimposed on the ultrasound image B23 to obtain the Doppler color flow image 2, and the flow velocity vector information may be superimposed on the ultrasound image B13 to obtain the vector flow image 1. Here, the ultrasound image B23 and the ultrasound image B13 may be the same, or different. For example, the ultrasound image B13 may be an enhanced B mode image.

In FIG. 19, the vector flow image may be displayed within a display region (such as the solid box in FIG. 19) in the Doppler color flow image. In addition, the transparency may also be used to distinguish the two kinds of images. For example, in one embodiment, the transparencies of the Doppler color flow image and the vector flow image may be adjustable. For example, the transparencies of the Doppler color flow image and the vector flow image may be adjusted in opposite ways. When the transparency of the Doppler color flow image is adjusted from 100% to 0%, the transparency of the vector flow image may be adjusted from 0% to 100%. They may be adjusted in opposite ways such that there is a difference between them to display the two images in contrast, thereby providing a display mode with more comfort and stronger contrast. In FIG. 19, within the display region, the transparency of the Doppler color flow image may be 100%. The adjustment of the transparency may be performed by the imaging system by default. Alternatively, the adjustment of the transparency may be performed according to inputs inputted by the user through the user interface. Besides the transparency, colors may also be used to distinguish the two kinds of images such that the Doppler color flow image 2 at the bottom and the vector flow image 1 at the top may be displayed in a contrast manner.

Figure 23:
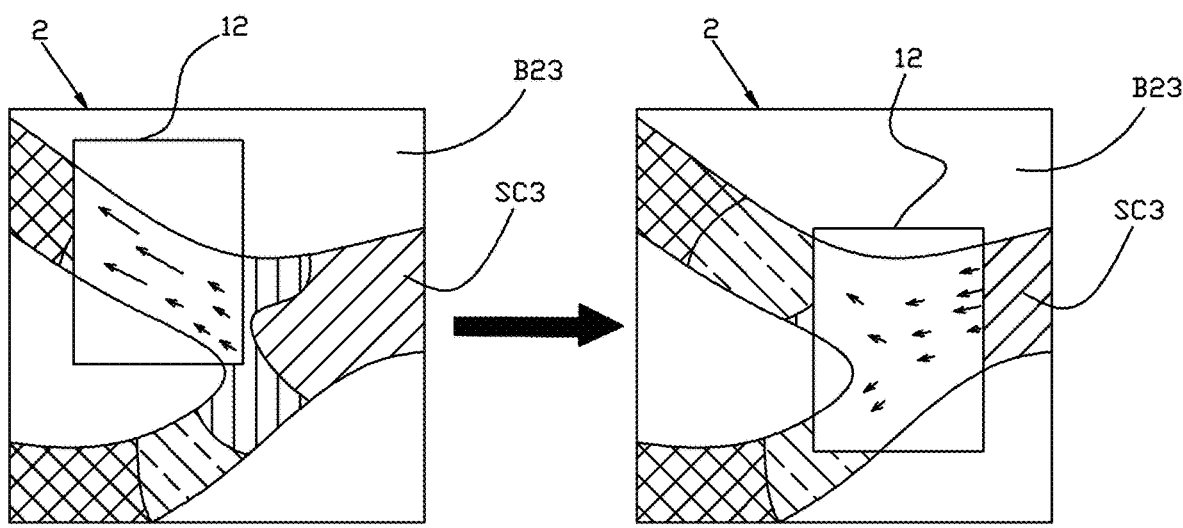
FIG. 23 schematically shows a display mode in an embodiment.

As shown in FIG. 19 and FIG. 23, in one embodiment, at least a part of the vector flow image may be displayed within a first vector flow display region 12 formed in the display region in the Doppler color flow image 1. In addition, as shown in FIG. 23, the user may move the first vector flow display region 12 in the display region of the Doppler color flow image 1 through the user interface. When the first vector flow display region 12 is moved, at least a part of the vector flow image which corresponds to the first vector flow display region 12 may be displayed within the first vector flow display region 12. Therefore, the flow velocity vector information at different locations in the Doppler color flow image 1 may be displayed.

In some embodiments, simultaneously displaying the vector flow image and the Doppler color flow image will not be limited to the methods described above.

Figure 20:
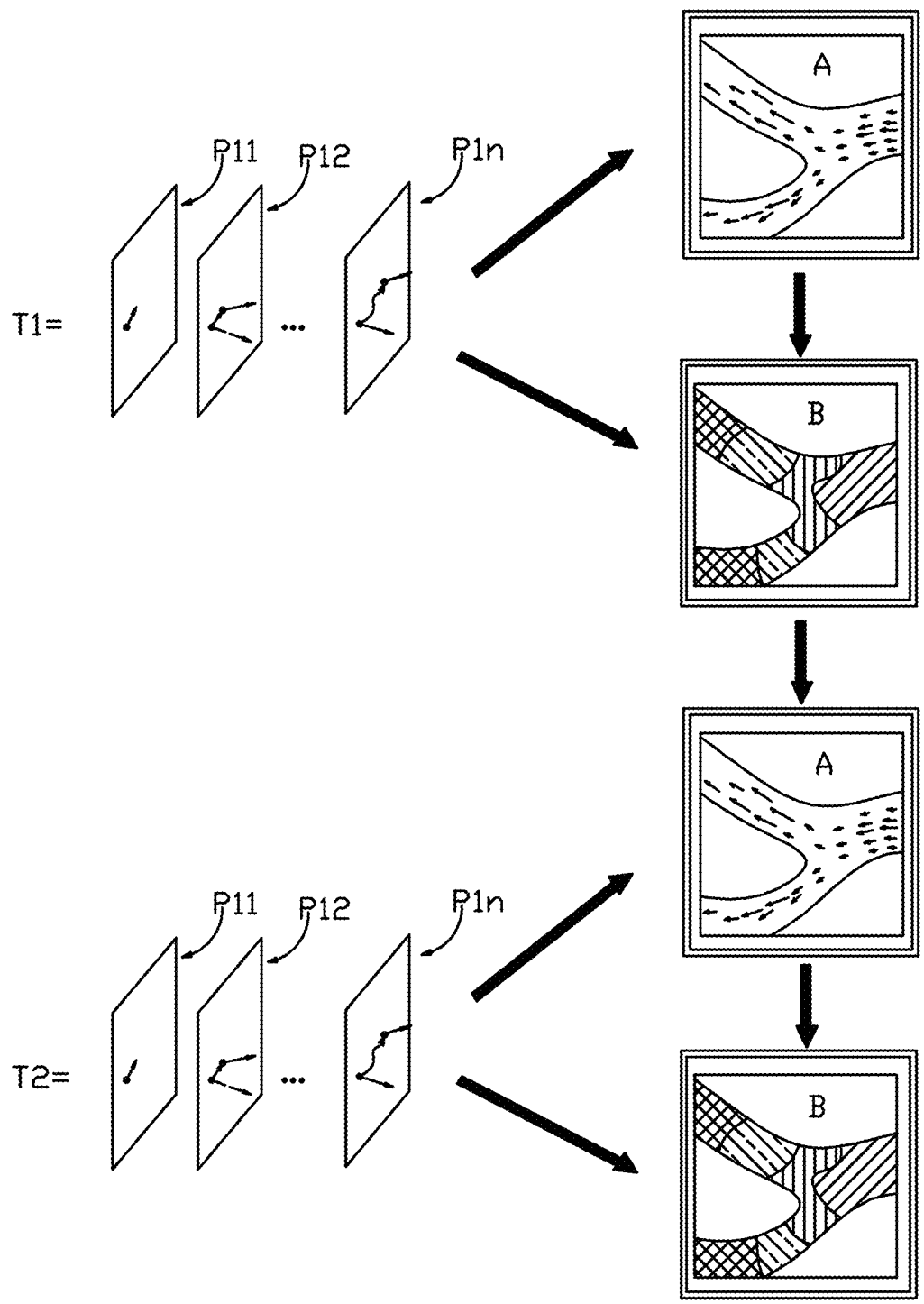
FIG. 20 schematically shows the obtaining of the image data in an embodiment.
Figure 21:
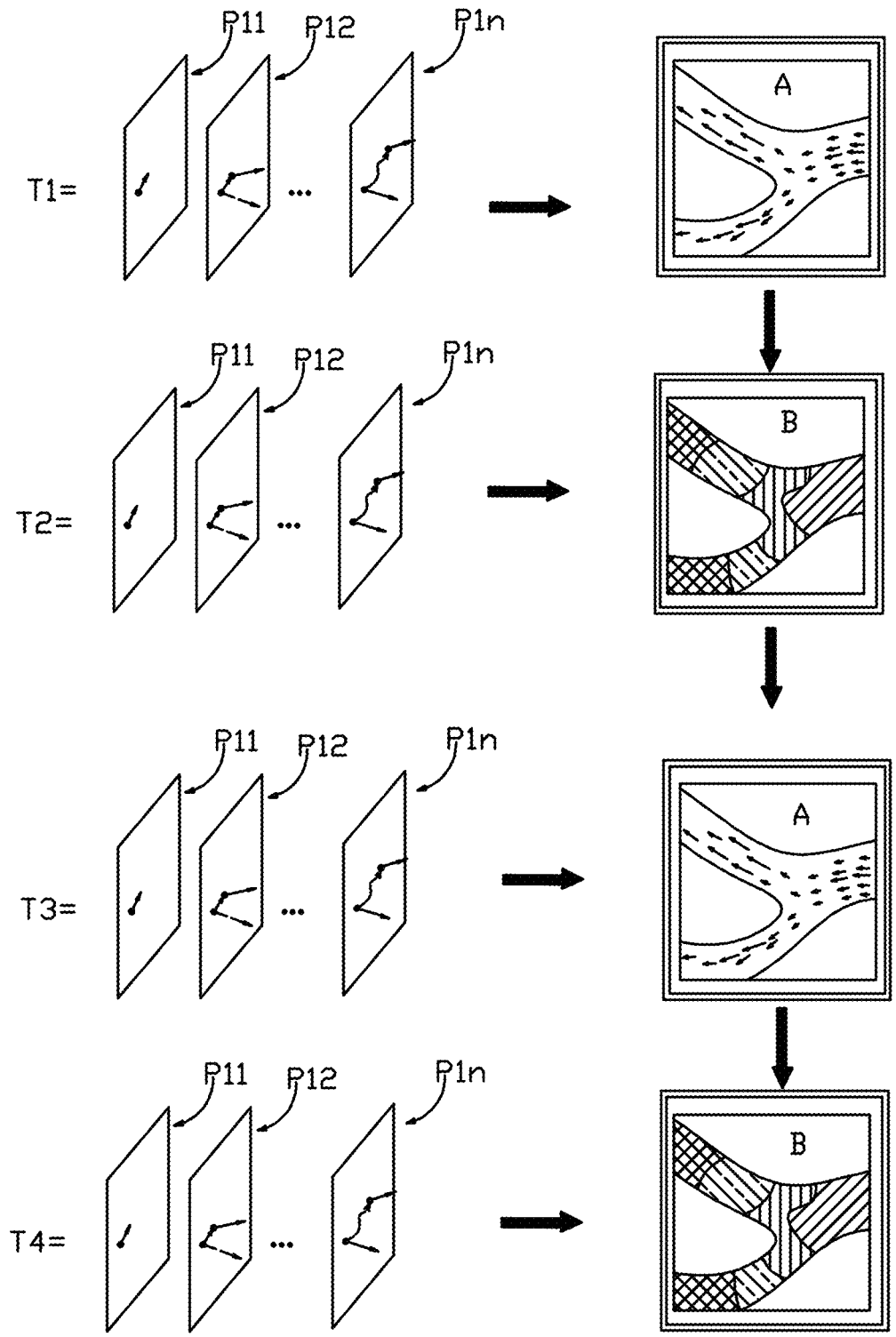
FIG. 21 schematically shows the obtaining of the image data in an embodiment.

In the time-sharing display mode or the simultaneous display mode, the flow velocity vector information and the Doppler flow velocity information obtained in step S400 may both be derived from the ultrasound echo signals obtained in a same pre-set sampling period, or may be respectively derived from the ultrasound echo signals obtained in two adjacent sampling periods. Here, the sampling period may be the imaging period obtained according to the display frame rate, or a time period set by the user or the imaging system. One or more frames of ultrasound image data may be obtained according to the ultrasound echo signals obtained in one preset sampling period. As shown in FIG. 20 and FIG. 21, in the successive sampling periods T1, T2, T3, T4 . . . , according to the ultrasound echo signals obtained in each sampling period, one or more frames of ultrasound image data P11, P12 . . . P1$n$ may be obtained, where n ≥ 1.

For example, in step S200, the echoes of the ultrasound beams may be received to obtain the ultrasound echo signals corresponding to a sampling period. In step S300, the ultrasound images may be obtained according to the ultrasound echo signals in the sampling period. In step S400, the flow velocity vector information and the Doppler flow velocity information of the target points may be obtained according to the ultrasound echo signals in the sampling period, respectively. In step S600, the Doppler color flow image and the vector flow image may be comparatively displayed, where, the vector flow image may be obtained by superimposing the flow velocity vector information of the target points on the ultrasound image obtained according to the ultrasound echo signals in the same sampling period, and the Doppler color flow image may be obtained by superimposing the Doppler flow velocity information on the ultrasound image obtained according to the ultrasound echo signals in the same sampling period.

As shown in FIG. 20, in the time-sharing display mode, one or more frames of ultrasound image data P11, P12 . . . P1$n$ may be respectively obtained in two successive sampling periods T1 and T2 according to the ultrasound echo signals corresponding to the sampling periods T1 and T2.

The flow velocity vector information V1 of the target points and the Doppler flow velocity information C1 may be respectively obtained according to the one or more frames of ultrasound images b1 of the sampling period T1, and the flow velocity vector information V2 of the target points and the Doppler flow velocity information C2 may be respectively obtained according to the one or more frames of ultrasound images b2 of the sampling period T2. In the time-sharing display mode, the vector flow image A obtained by superimposing the flow velocity vector information V1 on the ultrasound image b1 may firstly be individually displayed on the display 8, Thereafter, it may be switched into individually displaying on the display 8 the Doppler color flow image B obtained by superimposing the Doppler flow velocity information C1 on the ultrasound image b1. Thereafter, it may be switched into individually displaying on the display 8 the vector flow image A obtained by superimposing the flow velocity vector information V2 on the ultrasound image b2. Thereafter, it may be again switched into individually displaying on the display 8 the Doppler color flow image B obtained by superimposing the Doppler flow velocity information C2 on the ultrasound image b2. This way, the image data obtained in the two successive sampling periods T1 and T2 may be displayed in a time-sharing manner.

Similarly, in the simultaneous display mode, the vector flow image A obtained by superimposing the flow velocity vector information V1 on the ultrasound image b1 and the Doppler color flow image B obtained by superimposing the Doppler flow velocity information C1 on the ultrasound image b1 may be simultaneously displayed on the display 8. Thereafter, the vector flow image A obtained by superimposing the flow velocity vector information V2 on the ultrasound image b2 and the Doppler color flow image B obtained by superimposing the Doppler flow velocity information C2 on the ultrasound image b2 may be simultaneously displayed on the display 8. This way, the image data obtained in the two successive sampling periods T1 and T2 may be displayed in a time-sharing manner.

As another example, in step S200, the echoes of the ultrasound beams may be received to obtain the ultrasound echo signals corresponding to two adjacent sampling periods. In step S300, ultrasound images may be obtained according to the ultrasound echo signals corresponding to the two adjacent sampling periods. In step S400, the flow velocity vector information of the target points may be obtained according to the ultrasound echo signals obtained in one sampling period of the two adjacent sampling periods, and the flow velocity vector information may be superimposed on the ultrasound image obtained according to the ultrasound echo signals in this sampling period to form the vector flow image to be displayed in step S600. The Doppler flow velocity information may be obtained according to the ultrasound echo signals obtained in the other sampling period of the two adjacent sampling periods, and the Doppler flow velocity information may be superimposed on the ultrasound image obtained according to the ultrasound echo signals in said other sampling period to form the Doppler color flow image to be displayed in step S600.

Therefore, in step S600, the displayed Doppler color flow image and vector flow image may represent the image data obtained in successive sampling periods. For example, in the time-sharing display mode, as shown in FIG. 21, in four successive sampling periods T1, T2, T3 and T4, one or more frames of ultrasound image data P11, P12 . . . P1$n$ may be obtained respectively according to the ultrasound echo signals in each sampling period. The flow velocity vector information V1 of the target points may be obtained according to the one or more frames of ultrasound images b1 in the sampling period T1, the Doppler flow velocity information C2 may be obtained according to the one or more frames of ultrasound images b2 in the sampling period T2, the flow velocity vector information V3 of the target points may be obtained according to the one or more frames of ultrasound images b3 in the sampling period T3, and the Doppler flow velocity information C4 may be obtained according to the one or more frames of ultrasound images b4 in the sampling period T4.

In the time-sharing display mode, firstly, the vector flow image A obtained by superimposing the flow velocity vector information V1 on the ultrasound image b1 may be individually displayed on the display 8, Thereafter, the Doppler color flow image B obtained by superimposing the Doppler flow velocity information C2 on the ultrasound image b2 may be individually displayed on the display 8, Thereafter, the vector flow image A obtained by superimposing the flow velocity vector information V3 on the ultrasound image b3 may be individually displayed on the display 8, Thereafter, the Doppler color flow image B obtained by superimposing the Doppler flow velocity information C4 on the ultrasound image b4 may be individually displayed on the display 8. This way, the image data obtained in four successive sampling periods T1 to T4 may be displayed in a time-sharing manner.

Similarly, in the simultaneous display mode, firstly, the vector flow image A obtained by superimposing the flow velocity vector information V1 on the ultrasound image b1 and the Doppler color flow image B obtained by superimposing the Doppler flow velocity information C2 on the ultrasound image b2 may be simultaneously displayed on the display 8, and then the vector flow image A obtained by superimposing the flow velocity vector information V3 on the ultrasound image b3 and the Doppler color flow image B obtained by superimposing the Doppler flow velocity information C4 on the ultrasound image b4 may be simultaneously displayed on the display 8. This way, the image data obtained in four successive sampling periods T1 to T4 may be displayed in a time-sharing manner.

In another embodiment, the flow velocity vector information obtained in step S400 may be superimposed on the Doppler color flow image.

Figure 22:
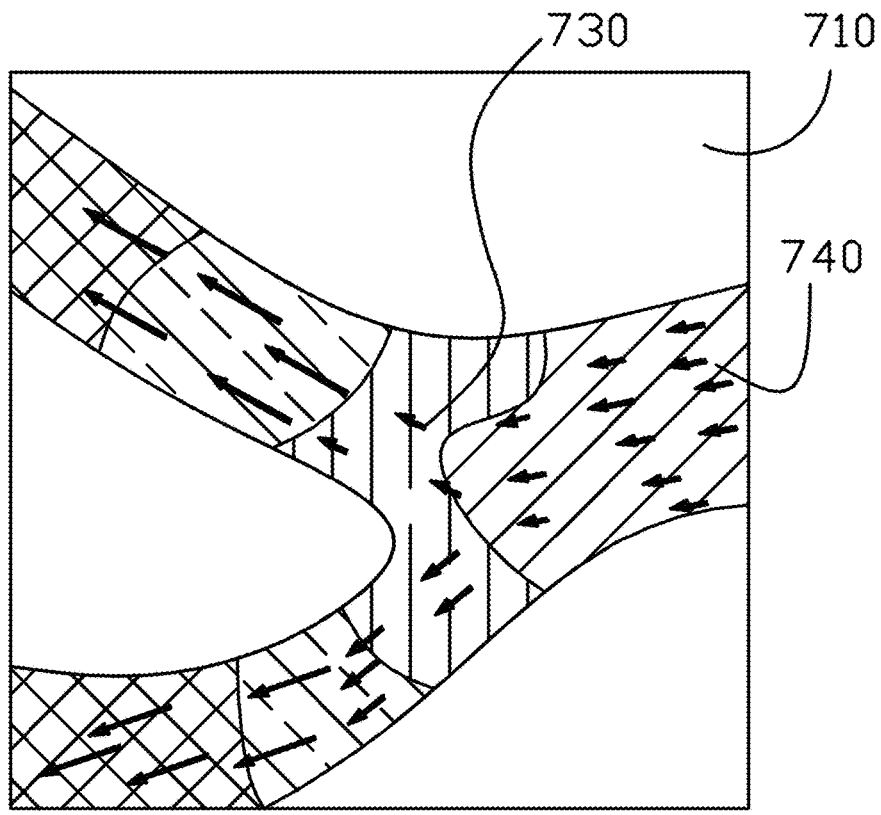
FIG. 22 schematically shows superimposing the flow velocity vector information on the Doppler color flow image in an embodiment.

When the images are displayed, the transparency of the flow velocity vector information may be adjustable. The transparency may be adjusted by the imaging system by default, or by inputs inputted by the user through the human-machine interaction device. Alternatively, the superimposed flow velocity vector information may be marked with colors which are different from the colors of the Doppler flow velocity information on the Doppler color flow image in order to distinguish the flow velocity vector information from the background image. As shown in FIG. 22, the flow velocity vector information 730 may be superimposed on the Doppler color flow image 710, and the hatchings on the Doppler color flow image 710 may represent the colors or hues of the Doppler flow velocity information. For example, the magnitude of velocity in the Doppler flow velocity information may be represented with colors such as red, yellow, orange, green or blue, etc. Alternatively, the magnitude of velocity in the Doppler flow velocity information may be represented with color with different saturations in the range of 0-100% (e.g., graded blue). Therefore, the marks used for marking the flow velocity vector information may be distinguished from the Doppler flow velocity information by colors or transparency, etc. For example, the marks of the flow velocity vector information may be represented by colors such as purple or cyan, or by color with saturation adjustable in the range of 0-100% (such as graded red) which is different from that of the Doppler flow velocity information. In FIG. 22, the arrows may represent the flow velocity vector information. In the embodiment, two kinds of flow velocity vector information may be obtained according to the first mode and the second mode described above, and marked on the Doppler color flow image according to the Doppler color flow image currently displayed.

Figure 24:
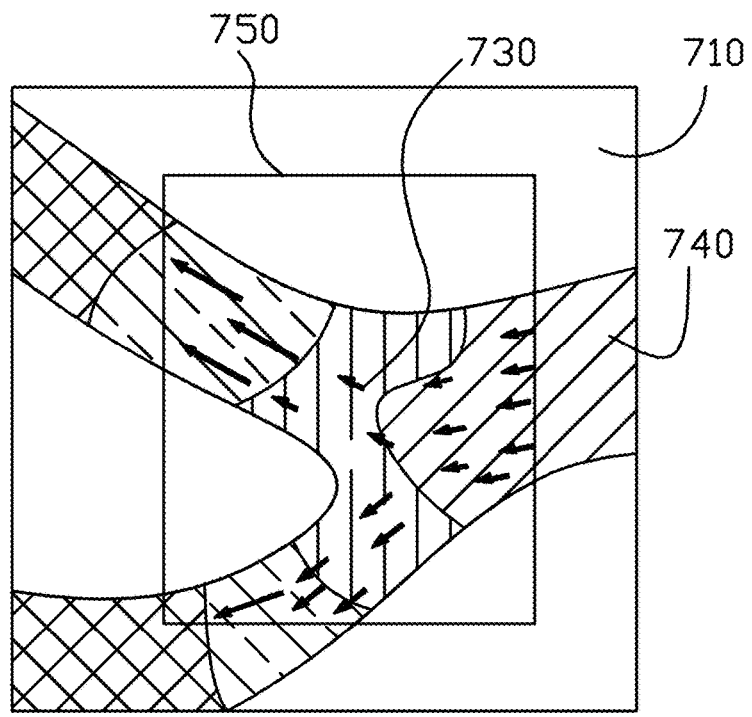
FIG. 24 schematically shows a display mode in an embodiment.
Figure 25:
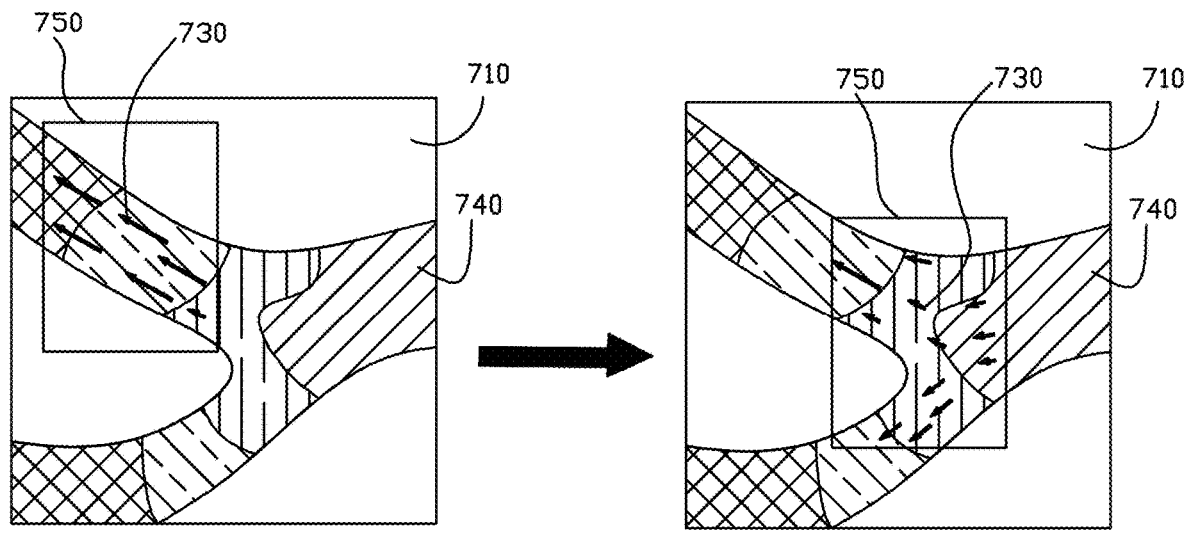
FIG. 25 schematically shows a display mode in an embodiment.

As shown in FIG. 22, the flow velocity vector information 730 may be superimposed on the entire display region of the Doppler color flow image 710. Alternatively, as shown in FIG. 24, the flow velocity vector information 730 may be displayed within a second vector flow display region 750 in the display region of the Doppler color flow image 710. In addition, as shown in FIG. 25, the user may move the second vector flow display region 750 in the display region of the Doppler color flow image 710 through the human-machine interaction device. When the second vector flow display region 750 is moved, the flow velocity vector information of the target points within said second vector flow display region may be superimposed in the second vector flow display region 750.

Multiple display modes have been described above, such as the individual display mode where the vector flow image or the Doppler color flow image may be individually displayed, the display modes where the flow velocity vector information may be superimposed on the Doppler color flow image, and the display modes where the vector flow image and the Doppler color flow image may be displayed simultaneously or in a time-sharing manner, etc. In one embodiment, the mode switching instruction inputted by the user through the human-machine interaction device may be obtained. The current display mode may be switched into any other display mode obtained by performing step S600 according to the mode switching instruction inputted by the user. The display modes obtained by performing step S600 may include:

1. the mode where the user may select the target points freely, as shown in FIG. 11 or FIG. 12;
2. the time-sharing display mode, for example, the display mode as shown in FIG. 17;
3. the simultaneous display mode, for example, the display mode as shown in FIG. 18 or FIG. 19;
4. the display mode where the flow velocity vector information may be superimposed on the Doppler color flow image, as shown in FIG. 22;
5. the display mode where the flow velocity vector information may be superimposed in the second vector flow display region in the Doppler color flow image, as shown in FIG. 24;
6. the display mode where the second vector flow display region may be moved, as shown in FIG. 25;
7. the display mode where the first vector flow display region may be moved, as shown in FIG. 23; and
8. the display mode where two displays may be used to simultaneously display the vector flow image and the Doppler color flow image; etc.

Figure 26:
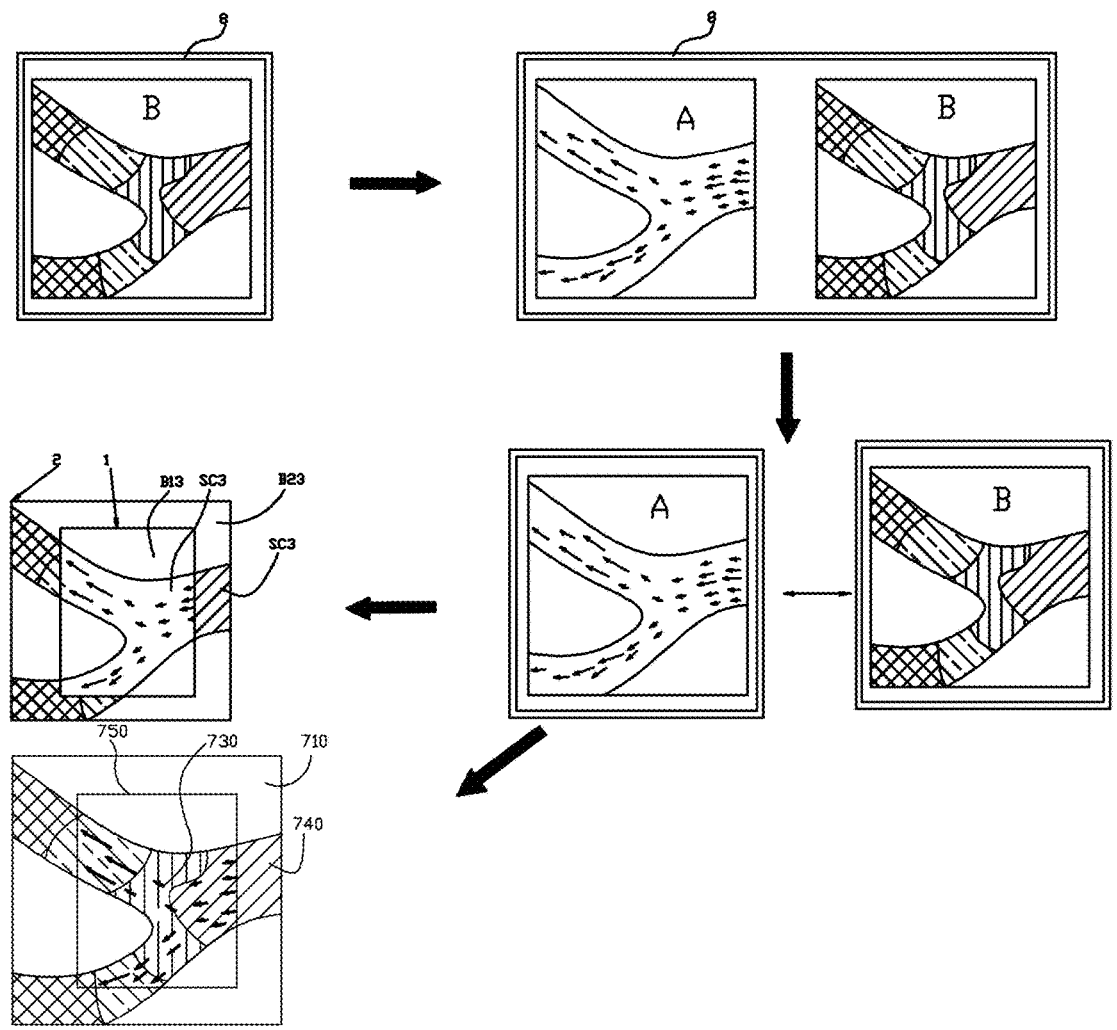
FIG. 26 schematically shows the switching between the modes according to the mode switching instruction in an embodiment.

For example, as shown in FIG. 26, it may be switched from the display mode where the vector flow image is individually displayed on the display 8 into the display mode where the vector flow image A and the Doppler color flow image B are simultaneously displayed on the display 8 according to the mode switching instruction inputted by the user. Thereafter, again according to the mode switching instruction inputted by the user, it may further be switched from the display mode where he vector flow image A and the Doppler color flow image B are simultaneously displayed on the display 8 into the time-sharing display mode as shown in FIG. 17 where the vector flow image A and the Doppler color flow image B are displayed alternately. Thereafter, it may further be switched into the display mode as shown in FIG. 19 where the vector flow image and the Doppler color flow image are simultaneously displayed according to the mode switching instruction inputted by the user. Alternatively, it may further be switched into the display mode as shown in FIG. 24 where the flow velocity vector information is superimposed on the second vector flow display region in the Doppler color flow image according to the mode switching instruction inputted by the user.

As another example, it may be switched from the display mode where the vector flow image or the Doppler color flow image is individually displayed on the display 8 into the display mode where the vector flow image and the Doppler color flow image are simultaneously on two displays. For example, in the case that two displays are used to simultaneously display the vector flow image and the Doppler color flow image, the data processing unit may provide two outputs of image data, one of which may be provided to the first display where the vector flow image may be displayed, the other may be provided to the second display where the Doppler color flow image may be displayed.

Multiple display modes for displaying the Doppler color flow images and the flow velocity vector information have been described above. In one embodiment, the imaging region of the vector flow image may be selectable. For example, in step S600, the vector flow image may be formed by superimposing the ultrasound image and the flow velocity vector information such that at least a portion of the vector flow image is displayed in the vector flow display region formed in the display region of the Doppler color flow image. Alternatively, the flow velocity vector information may be displayed on the vector flow display region formed in the display region of the Doppler color flow image. For example, the boxes with solid lines in FIG. 23 and FIG. 24 may represent the vector flow display regions.

The user may move the vector flow display region through the human-machine interaction device. After obtaining the moved vector flow display region, the ultrasound imaging system may obtain the range of the vector flow display region, and obtain the flow velocity vector information of the target points within said range. The ultrasound imaging system may display at least a portion of the vector flow image within the moved vector flow display region, where said portion of the vector flow image may be formed by superimposing the obtained flow velocity vector information of the target points on at least a portion of the ultrasound image. Alternatively, the ultrasound imaging system may display the obtained flow velocity vector information of the target points within the moved vector flow display region.

In the embodiments above, in the step for superimposing the flow velocity vector information on the ultrasound image to form the vector flow image, the flow velocity vector information may be superimposed on the ultrasound image obtained in step S300 above, or the flow velocity vector information of a portion of the target points may be displayed on the ultrasound image, or the flow velocity vector information may be displayed on the vector flow display region formed in the display region of the Doppler color flow image. For example, the box with solid lines in the Doppler color flow image in FIG. 19 may represent the vector flow display region.

In order to highlight the flow velocity vector information on the display interface of the display 8, in step S600 for comparatively displaying the flow velocity vector information and the Doppler color flow image, marks may be used to mark the flow velocity vector information at corresponding positions in the background image, thereby highlighting the flow velocity vector information from the background image. In one embodiment, one or more of the color, the transparency, the contrast and the shape of the marks used to mark the flow velocity vector information on the background image may be configured to distinguish the marks from the background image. For example, the color of the marks may be red, yellow or blue, etc., and the marks may be the arrows, dots, triangles or squares, etc. in FIG. 15 and FIG. 16. In the case that the arrows are used as the marks marking the flow velocity vector information, the type of the line may also be selectable. In addition, in one embodiment, the transparency of the marks may be adjustable. Alternatively, the transparency of the marks may change gradually. For example, the marks with transparencies changing in the range of 50-100% may be used on the background image.

Figure 27:
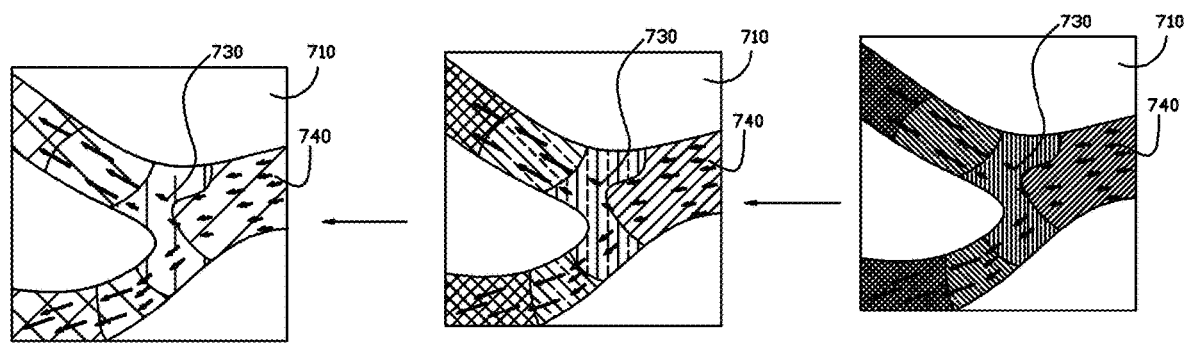
FIG. 27 schematically shows the background image whose transparency is adjustable in an embodiment.

The background image mentioned above may include entire or a portion of the ultrasound image or the Doppler color flow image, etc. As shown in FIG. 19 and FIG. 20, the background image may be the entire or a portion of the Doppler color flow image. In the vector flow image described above, the background image may be the entire or a portion of the ultrasound image. For example, as shown in FIG. 27, when the flow velocity vector information (the black arrows 730 in the figure) are superimposed on the Doppler color flow image as shown in FIG. 22, the transparency of the background image may be adjusted or may change gradually, thereby highlighting the flow velocity vector information (the black arrows 730 in the figure) superimposed on the background image. In FIG. 27, the density of the hatching 740 in the Doppler color flow image may be different from right to left, thereby representing the difference of the transparency between the regions of the Doppler flow velocity information in the Doppler color flow image. Furthermore, the gradual change of the transparency of the Doppler flow velocity information region may also be represented. Therefore, the marks used to mark the flow velocity vector information, i.e., the black arrows 730 in the figure, may be gradually highlighted on the background image. The ways for highlighting the marks used for marking the flow velocity vector information by adjusting the transparency of the background image may also be used in any display mode described in the embodiments above where the flow velocity vector information may be superimposed on a certain image.

The color of the marks used for marking the flow velocity vector information on the background image may be any color obtained by adjusting one or more parameters of the hue, the saturation and the contrast, etc. The shape of the marks may be multiple dots or arrows or any other marks which are able to indicate the direction. The direction of the marks may be used to represent the direction of the flow velocity vector information, and the attributes of the marks such as length or size, etc. may be used to represent the absolute value of the flow velocity vector information. Alternatively, the color of the marks may be used to represent the velocity level of the absolute value of the flow velocity vector information. For example, the marks used for marking the flow velocity vector information of the target points when comparatively displaying the flow velocity vector information and the Doppler color flow image may include one or more of particles, arrows, flowing lines, squares and dots, etc. In one embodiment, the marks may be set by the user in order to mark the target points to be tracked according to the needs of the user and represent the trajectories of different target points, thereby facilitating understanding the actual blood flow of the lesions in the scanning target and the factors that cause the lesions. These ways may facilitate clearly showing the motion of the flow in the lesions in the scanning target.

The ultrasound echo signals used for calculating the flow velocity vector information and the ultrasound echo signals used for calculating the Doppler flow velocity information and for obtaining the ultrasound images may come from the ultrasound echo signals in the same time period, such that the flow velocity vector information and the Doppler color flow image may be synchronous.

For example, in step S200, the echoes of the ultrasound beams may be received, and the echoes of the ultrasound beams in a preset time period may be stored. Based on the stored echo signals, the flow velocity vector information, the Doppler flow velocity information and the ultrasound image all corresponding to the same group of echo signals may be obtained. The Doppler color flow image in the preset time period may be obtained by superimposing the Doppler flow velocity information and the ultrasound image, and the flow velocity vector information in the preset time period may also obtained.

In another embodiment, in step S200, the echoes of the ultrasound beams may be received, and the ultrasound echo signals in a preset time period may be obtained according to the received echoes, and stored. The flow velocity vector information, the Doppler flow velocity information and the ultrasound image may be obtained according to the obtained ultrasound echo signals. Based on the stored echo signals, the flow velocity vector information, the Doppler flow velocity information and the ultrasound image all corresponding to the same group of echo signals may be obtained. The Doppler color flow image in the preset time period may be obtained by superimposing the Doppler flow velocity information and the ultrasound image, and the flow velocity vector information in the preset time period may also obtained.

In one embodiment, in step S300, the flow velocity vector information of the target points obtained based on the ultrasound echo signals in the preset time period may be stored, such that it may be displayed in step S700. For example, the stored flow velocity vector information may be the flow velocity vector information of the target points within the scanning body obtained as described above in the preset time period, or be the flow velocity vector information of the target points within the two-dimensional ultrasound image in the preset time period.

In the present disclosure, the stored data will not be limited to the data described above. Other ways may also be used. The stored data may be read to obtain the flow velocity vector information, the Doppler flow velocity information and the ultrasound image for comparative display in step S700. For example, the Doppler color flow image in a preset time period and the flow velocity vector information obtained in said preset time period may be comparatively displayed according to the stored data. In another example, the Doppler color flow image may be obtained and displayed in real time according to the echoes received in real time, and the stored flow velocity vector information may be comparatively displayed on the Doppler color flow image displayed in real time. In another embodiment, the Doppler color flow image may be obtained in real time, and Doppler color flow images in a time period may be stored and displayed, where the flow velocity vector information of the target points in the ultrasound images in said time period may be comparatively displayed.

The preset time period in the embodiments above may be one or more sampling periods mentioned above, as described with respect to the sampling period and the FIG. 20 and FIG. 21 above. In one embodiment, the ultrasound echo signals in the preset time period may at least include the data used for forming the ultrasound images at two adjacent times. For example, the ultrasound echo signals in the preset time period may at least include the data used for forming two frames of ultrasound image. The flow velocity vector information of the target points may mainly be used for display in the vector flow image or on the Doppler color flow image. Therefore, the flow velocity vector information of the target points obtained above may be the flow velocity vector information obtained in the first mode and the second mode described above.

Based on the stored data, when the Doppler color flow image and the flow velocity vector information are comparatively displayed, one of the following steps may be performed in step S600 to ensure the synchronization between the Doppler color flow image and the flow velocity vector information:

1. freezing the Doppler color flow image obtained in step S500; and
2. slowing down the display of the flow velocity vector information of the target points, thereby comparatively displaying the slowed down flow velocity vector information and the Doppler color flow image.

The freezing may be implemented by any of the following ways:

1. displaying the Doppler color flow image repeatedly; and
2. slowing down the display of the Doppler color flow image.

The frozen Doppler color flow images may all come from the stored Doppler color flow images in the preset time period, or may be obtained based on the stored ultrasound echo signals in the preset time period. In the display mode where the Doppler color flow images are frozen, the flow velocity vector information obtained in real time may be display normally. Alternatively, the slowed down flow velocity vector information may be displayed in the following manner.

In order to avoid that the displayed flow is too fast to be recognized by human eye, in one embodiment, the flow velocity vector information obtained in step S400 may be slowed down before the comparative display in step S600, such that the slowed down flow velocity vector information and the Doppler color flow image may be comparatively displayed. For example, firstly, the flow velocity vector information may be slowed down to obtain slow flow velocity vector information. Thereafter, the slow flow velocity vector information may be superimposed on the ultrasound image to form the vector flow image, or on the Doppler color flow image, thereby achieving the comparative display of the flow velocity vector information and the Doppler color flow image.

In the present disclosure, related parameters may be inputted by the user to adapt to different applications. In one embodiment, slowing down the flow velocity vector information may include:

firstly, obtaining the ratio selection instruction representing the play ratio selected by the user; and, thereafter, adjusting the play speed of the flow velocity vector information of the target points when the flow velocity vector information and the Doppler color flow images are comparatively displayed in step S600 according to the play ratio selected by the ratio selection instruction. In this embodiment, the user may select the play speed of the flow velocity vector information as needed, thereby more clearly understanding the actual situation of the flow.

Figure 32:
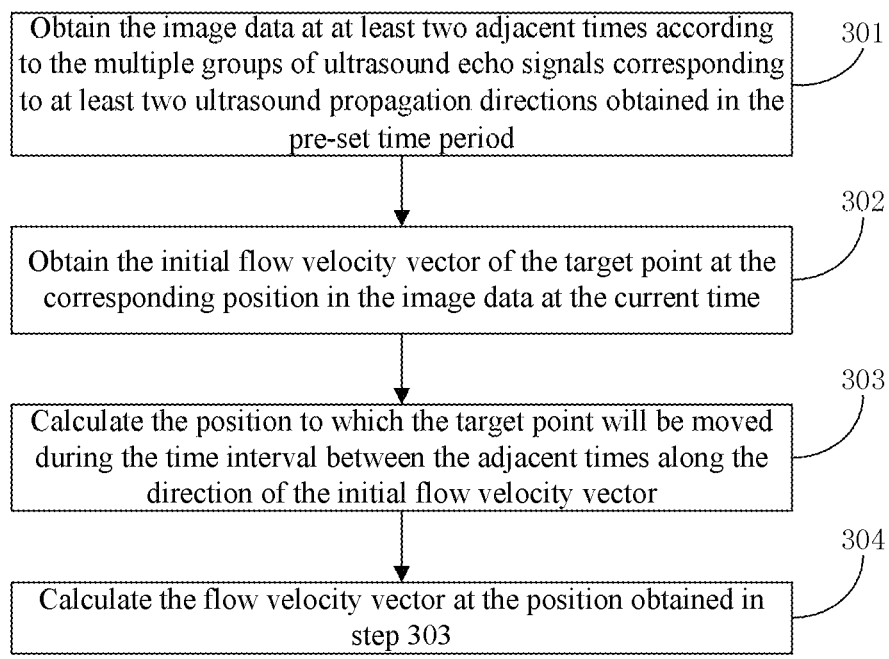
FIG. 32 is a schematic flow chart of the step S400 in an embodiment.

In step S600, the flow velocity vectors at the corresponding positions to which the target point is successively moved may be displayed to form the flowing mark over time. In this case, when the flow velocity vector information of the target points obtained in step S400 is the flow velocity vector information at the corresponding position to which the target point is successively moved, in one embodiment, as shown in FIG. 32, the step S400 may include the following steps.

Step 301: obtaining the image data at least two adjacent times according to the at least two groups of ultrasound echo signals respectively corresponding to at least two ultrasound propagation directions obtained in the preset time period.

Step 302: obtaining the initial flow velocity vector of the target point at the corresponding position in the image data at the current time.

Step 303: calculating the position to which the target point will be moved during the time interval between the adjacent times along the direction of the initial flow velocity vector.

Step 304: calculating the flow velocity vector at this position, and storing or outputting the flow velocity vector and the information of the position in the image data at next time, such that the flow velocity vector information at said position may be displayed when the image data at the next time is displayed.

In step S700, the ultrasound image and the Doppler flow velocity information at the next time may be displayed to form the Doppler color flow image, and the flow velocity vector information at the position obtained in step 303 may be comparatively displayed. The information of the position here may include the pixel position where the flow velocity vector information to be displayed when the image is displayed on the display interface. In order to ensure the consistency of the displayed information, in step S600, the Doppler color flow image obtained according the ultrasound echo signals obtained in the preset sampling period may be frozen, and the flow velocity vector information obtained according to step 302 to step 304 above may be comparatively displayed. At the same time, the flow velocity vector information may be slowed down as described above.

Figure 33:
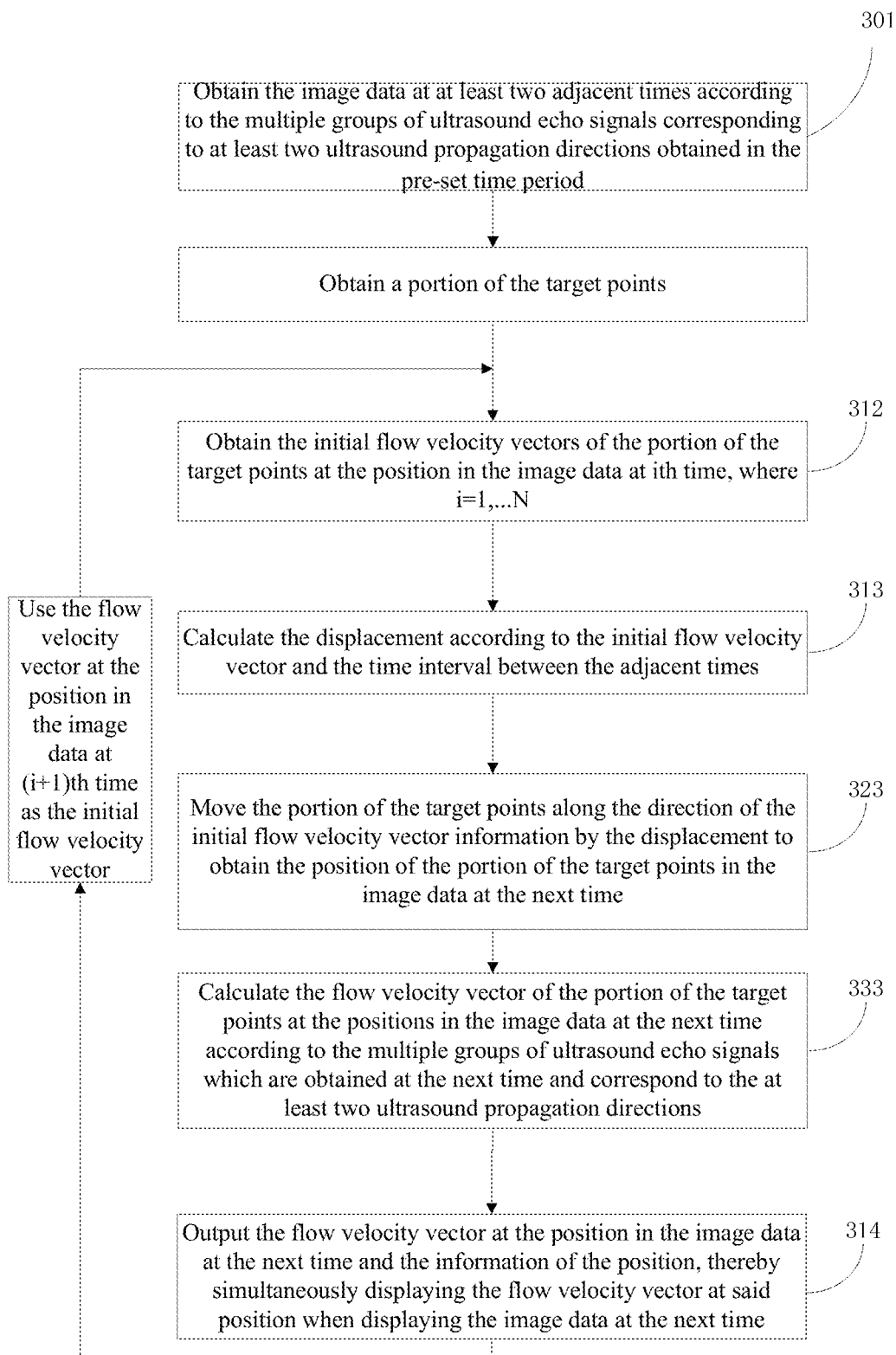
FIG. 33 is a schematic flow chart of the step S400 in an embodiment.

As shown in FIG. 33, the step 302 to step 304 may be performed repeatedly. For example, the flow velocity vector information at the positions in the image data at N times may be performed, and the flow velocity vector information corresponding to each two adjacent times may be obtained by the step 302 to step 304. The flow velocity vector information at the position in the image data at said next time may be used as the initial flow velocity vector information used for calculating the flow velocity vector information at the position in the image data at the next time, i.e., the flow velocity vector information at the position in the image data at i+1 (i=1, ..., N) time may be used as the initial flow velocity vector information, and then it may come back to step 302 to calculate the flow velocity vector information of at least a portion of the target points at the position in the image data at the rest of the times.

In this embodiment, the actual flow direction of the target points in the scanning target may be clearly shown in the vector flow image. Compared with displaying the magnitude and direction of the flow over time only at the fixed position on the image, the actual flowing in the scanning target may be shown more accurately, more real and more vividly. The flowing of the flow may be represented by flowing dots or arrows or other flowing marks which are able to indicate the direction.

In one embodiment, as shown in FIG. 33, in step S300, calculating the flow velocity vector information may include:

step 301: obtaining the image data at at least two adjacent times according to the at least two groups of ultrasound echo signals which are obtained at the preset time period and correspond to at least two ultrasound propagation directions;

step 312: obtaining a portion of the target points, and obtaining the initial flow velocity vector information of the portion of the target points at the positions in the image data at $i^{th}$ time, where i=1, ..., N;

step 313: calculating the displacement according to the initial flow velocity vector information and the time interval between the adjacent times;

step 323: moving at least a portion of the target points along the direction of the initial flow velocity vector information by the displacement to obtain the position of the portion of the target points in the image data at the next time;

step 333: calculating the flow velocity vector information of the portion of the target points at the positions in the image data at the next time according to the multiple groups of ultrasound echo signals which are obtained at the next time and correspond to the at least two ultrasound propagation directions;

step 314: storing or outputting the flow velocity vector information at the position in the image data at the next time and the information of the position, thereby comparatively displaying the flow velocity vector information at said position in the image (e.g., the Doppler color flow image or the ultrasound image) at the next time; and returning to step 312 to use the flow velocity vector information at the position in the image data at $(i+1)^{th}$ time as the initial flow velocity vector information in step 312 to calculate the flow velocity vector information at the position in the image data at the next time.

With the methods in the present embodiment, the flow velocity vector information displayed on the display interface in step S700 may truly represent the movement of the flow in the flow field. The target points represented by marks such as arrows etc. may move to corresponding position over time in the velocity of the flow along the direction of the flow and be displayed.

Performing the step 301 to step 314 may need more calculation. In order to avoid the excessive reduce in real-time due to performing the step 301 to step 314, the calculation of the flow velocity vector information by which at least a portion of the target points may be moved to the position in the image data at the next time during the time interval between the adjacent times may be completed before the ultrasound image at the next time is displayed. In addition, in one embodiment, the calculation for performing the step 301 to step 314 may be reduced. One or more discrete points, or the neighborhoods or data blocks respectively containing the one or more discrete points, may be used as the target points described above, thereby reducing the calculation.

In one embodiment, a plurality of methods for highlighting the flow velocity vector information in step S400 may further be provided. For example, the flow velocity vector information at the position where the cursor is located may be displayed on the display interface, i.e., one or two of the absolute value and direction of the velocity at the position where the cursor is located may be displayed.

Figure 34:
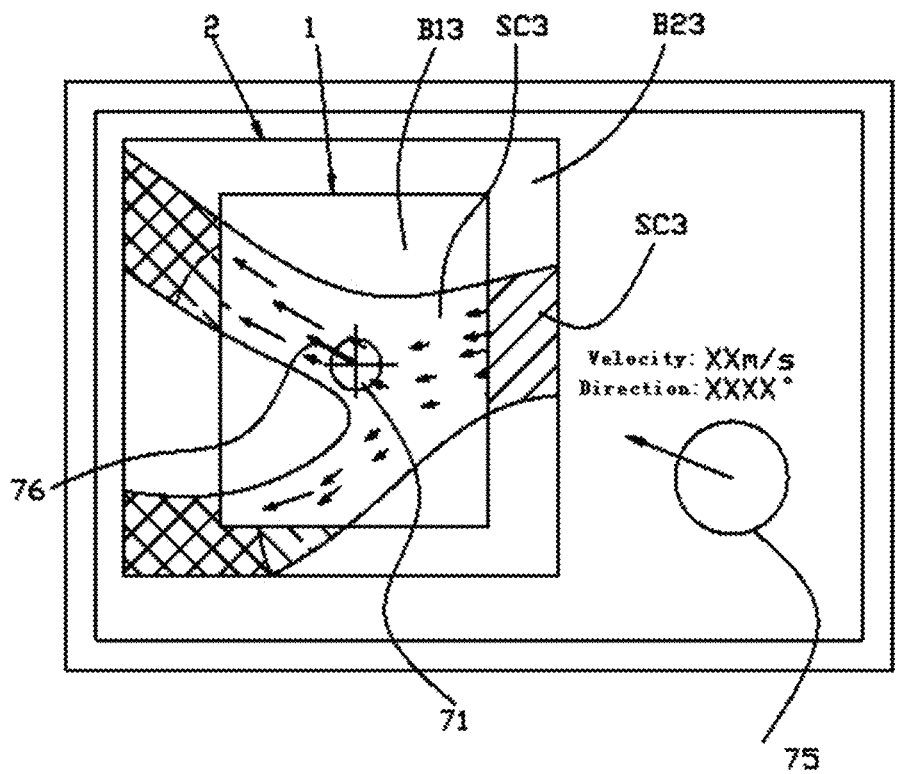
FIG. 34 schematically shows the display of the flow velocity vector information at the position of the cursor in an embodiment.

As shown in FIG. 34, the position of the cursor 71 may be obtained, and thereafter, the flow velocity vector information at said position may be obtained. Then, any one or two or more of the absolute value, the direction and the angular velocity of the flow velocity vector information at said position may be displayed on a region in the display interface. When the cursor is moved, the absolute and/or direction of the flow velocity vector information at said position displayed on the region in the display interface may change accordingly.

In one embodiment, as shown in the region on the right of FIG. 34, a graph whose area is related to the absolute value of the velocity may be displayed in the display region on the display interface above to represent the absolute value of the velocity of the flow velocity vector information at the current position of the cursor. For example, in FIG. 34, a circle whose radius is equal to the absolute value of the velocity of the flow velocity vector information may be displayed on the display interface to represent the absolute value of the velocity of the flow velocity vector information at the current position of the cursor. However, the present disclosure will not be limited to the circle whose radius is equal to the absolute value of the velocity of the flow velocity vector information. Other graphs may also be used, such as the square displayed in the region 75 in FIG. 36 whose side length is equal to the absolute value of the velocity of the flow velocity vector information, etc.

Figure 35:
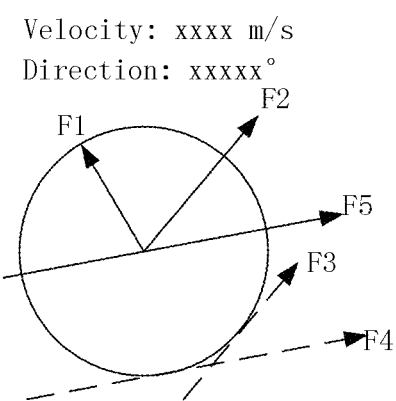
FIG. 35 schematically shows the display of the flow velocity vector information in an embodiment.

In another embodiment, a direction indication line pointing to the direction of the velocity may be displayed on the display interface to represent the direction of velocity of the flow velocity vector information at the current position of the cursor. For example, in FIG. 34, the direction indication line 76 may be displayed at the position of the cursor. In another embodiment, as shown in FIG. 34 and FIG. 35, a direction indication line pointing to the direction of the velocity may be displayed in the graph related to the absolute value of the velocity described above to represent the direction of velocity of the flow velocity vector information. For example, an indication line (such as the arrow on the circle of region 75) which intersects with the circle (the circle displayed at the position where the region 75 is located) and points to the direction of the velocity may be displayed on the display interface according to the direction of velocity of the flow velocity vector information, thereby representing the direction of velocity of the flow velocity vector information at the position of the cursor on the display interface. Alternatively, in FIG. 36, an indication line which intersects with the square (the square displayed at the position where the region 75 is located) and points to the direction of the velocity may be displayed according to the direction of velocity of the flow velocity vector information. The indication line herein may be a line which passes through or starts from the center of the graph and is or partially is straight line. As shown in FIG. 35, the indication line may be the line segment F1 from the center to the border of the circle, the line segment F2 which starts from the center of the circle and passes through the border of the circle, or the line formed by adding arrows at the end of the line segment F1 or F2, or the line segment F5 which passes through the center and the border of the circle, etc. The indication line herein may also be line which is parallel to the straight line or straight line segment passing through or starting from the center of the circle and intersects with the circle, such as the line segment F3 or F4 shown in FIG. 18. Therefore, in the present disclosure, the position of the direction indication line will not be limited. The direction indication line may be displayed at any position on the display interface. For example, the direction indication line pointing to the direction of the velocity may be displayed in the graph related to the absolute value of the velocity. In the present disclosure, the type of the line of the indication line will not be limited to those described above, and arrow is also not necessary. Any indication line which can represent the direction of the velocity of the flow at the cursor may be used.

Figure 36:
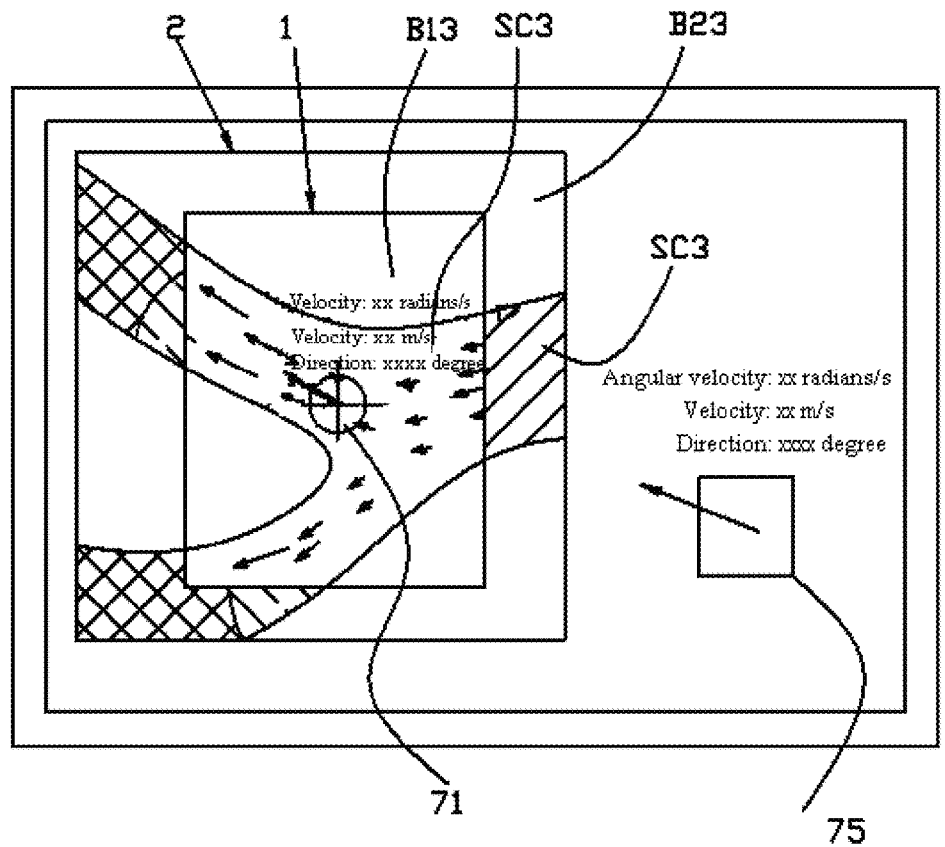
FIG. 36 schematically shows the display of the flow velocity vector information at the position of the cursor in an embodiment.

In one embodiment, the text information representing the flow velocity vector information may be displayed on the display interface to more clearly show the flow velocity vector information. For example, in FIG. 36, the text information "velocity: xxxx m/s", "direction: xxxx degree" and "angular velocity: xxx radians/second" may be displayed near the position of the cursor. In other embodiment, the text information representing the flow velocity vector information may be displayed near the graph described above. As shown in FIG. 34 to FIG. 36, the information "velocity: xxxx m/s", "direction: xxxx degree" and "angular velocity: xxx radians/second" may be displayed near the region 75. This way, the flow velocity vector information may be shown clearly and intuitively. In one embodiment, the angle information obtained according to the direction of the velocity in the plane coordinate system may be used to display the text information representing the direction of the velocity. When the cursor is moved, the radius of the circle, the side length of the square or the pointing direction of the arrow and the displayed text information in FIG. 34 and FIG. 36 may be moved and updated correspondingly.

Figure 37A:
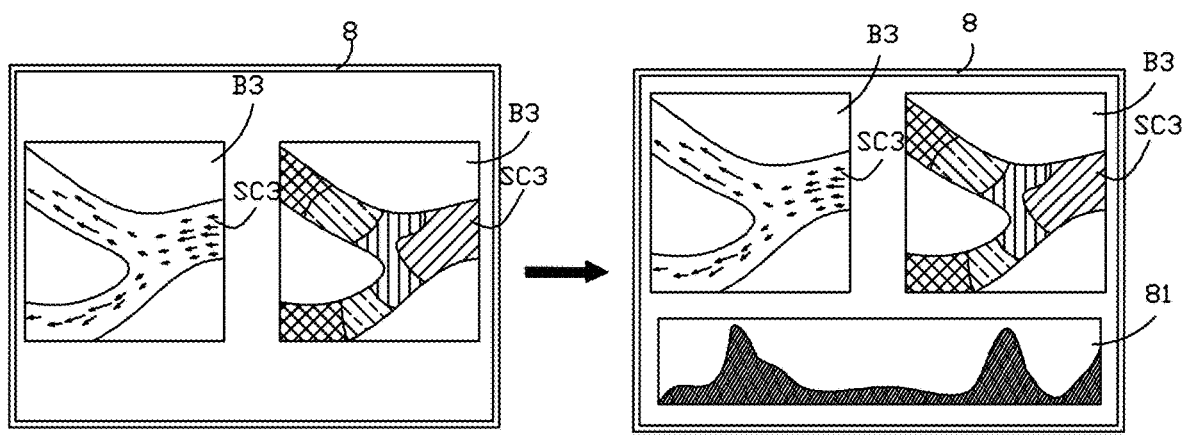
FIG. 37A and FIG. 37B schematically show the display of the spectrum obtained by pulse-wave Doppler imaging in two embodiments.

In one embodiment, other flow information may also be displayed. In the display mode shown in FIG. 11 where the Doppler color flow image and the vector flow image are displayed simultaneously, the display mode shown in FIG. 12 where the vector flow image is displayed within the vector flow display region (the box in the figure) formed in the display region of the Doppler color flow image or the display modes where the vector flow image is individually displayed, the Doppler spectrum image at the position of the cursor or at one or more pre-set positions may further be displayed on the display interface. For example, as shown in FIG. 37A, a Doppler spectrum display region 81 may be provided on the display interface. The position of the cursor on the vector flow image or the pre-set position may be obtained, and the Doppler spectrum at said position may be acquired, and then displayed on the display region 81. In the present embodiment, the Doppler spectrum image at the position of the cursor may be displayed on the display interface.

Figure 37B:
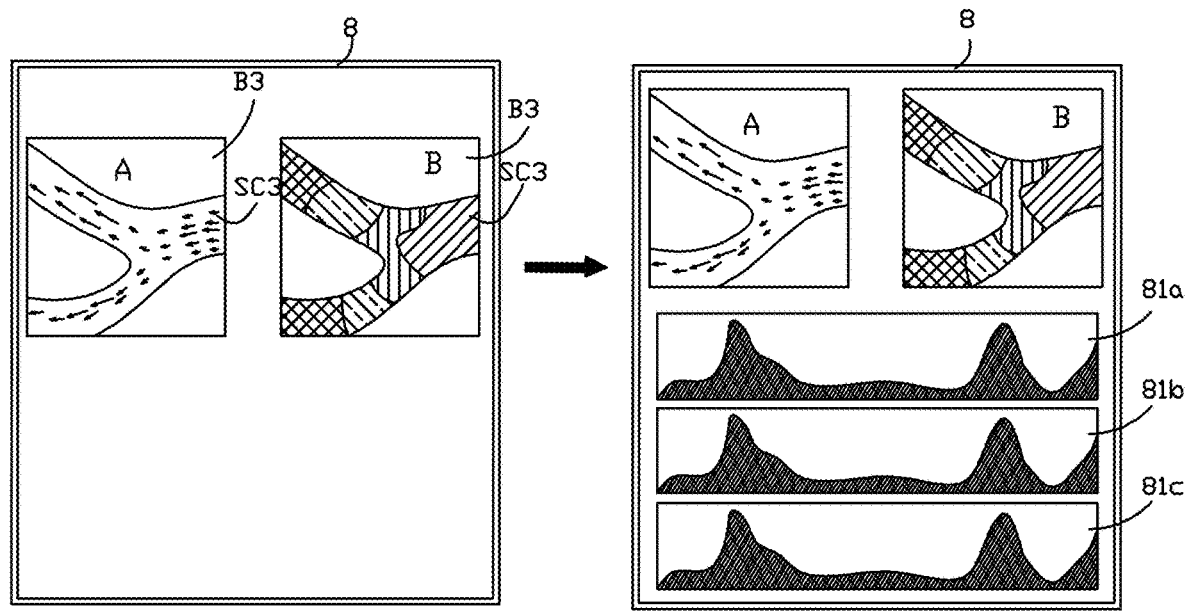

In one embodiment, the pre-set position mentioned above may be set on the display interface by the user through the machine-human interaction device. When the pre-set position is determined, the Doppler spectrum image at said pre-set position may be displayed. For example, as shown in FIG. 37B, multiple Doppler spectrum display regions (81*a*, 81*b*, 81*c*) may be provided on the display interface according to the number of the pre-set positions.

Figure 31:
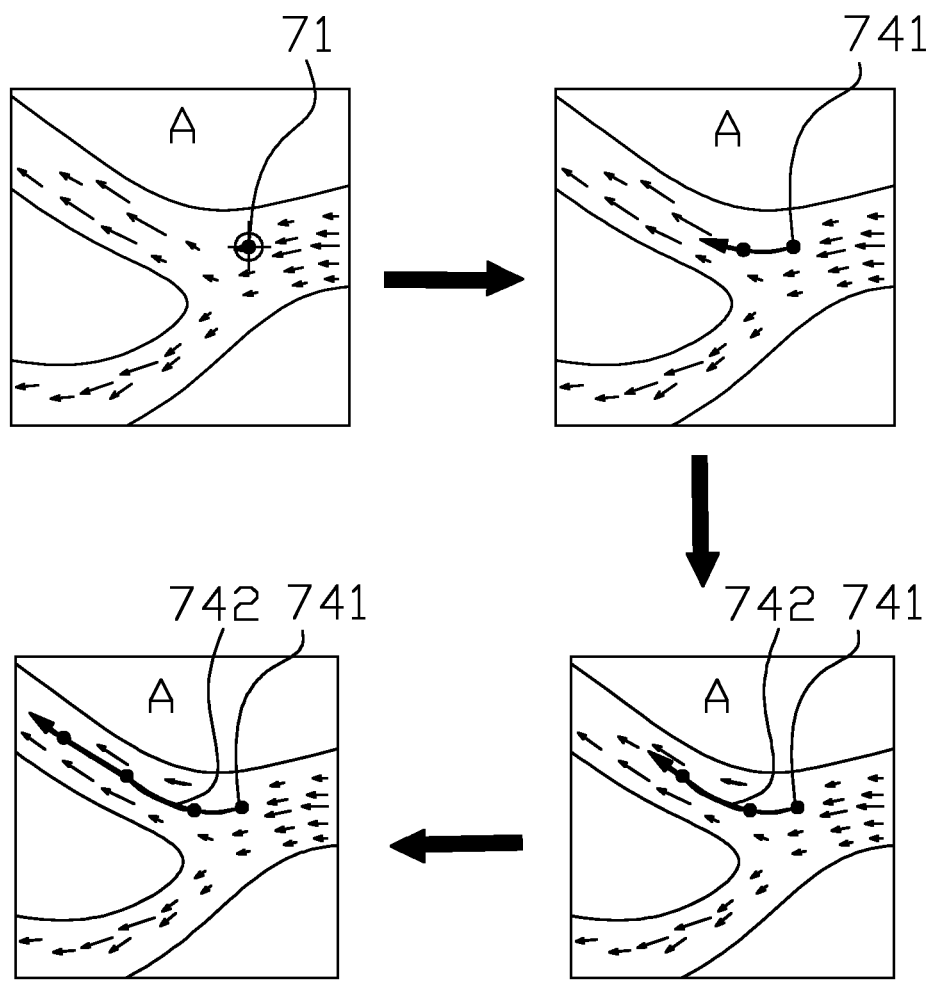
FIG. 31 schematically shows the formation of the trajectory of the selected target point in an embodiment.
Figure 38:
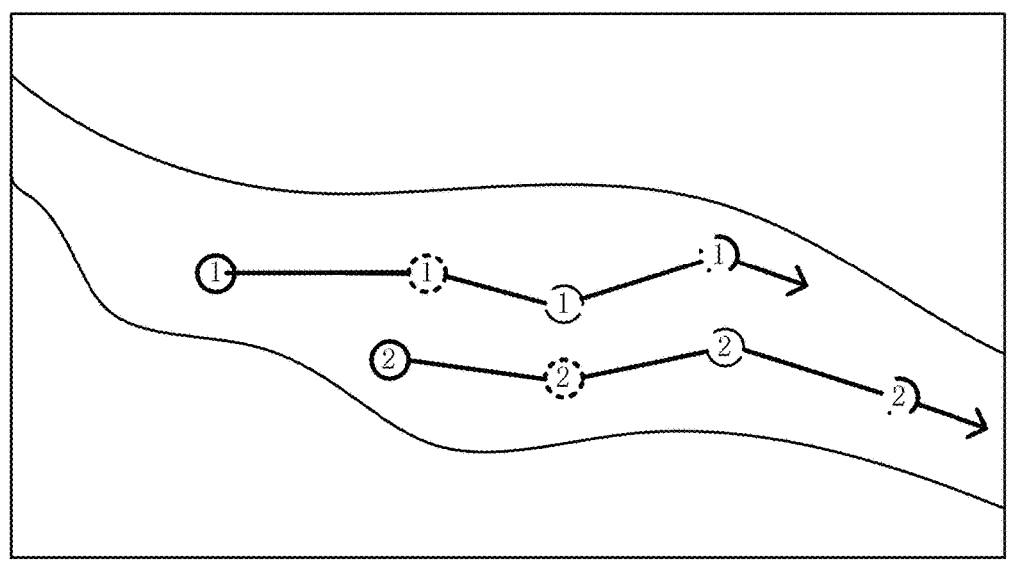
FIG. 38 schematically shows the formation of the trajectories in an embodiment.

In one embodiment, in the second mode of the flow velocity vector information described above, the multiple positions of a target point to which the target point is successively moved in the ultrasound images may be successively connected with connection lines to form the trajectory of said target point, and the trajectory may be displayed, thereby facilitating the observe of the user. As shown in FIG. 38, the line segments connecting the positions of the target points 1 and 2 may respectively form the trajectories of the target points 1 and 2. The trajectory of one or more target points may be displayed. For example, as shown in FIG. 31, when the target point 741 to be tracked is selected in the vector flow image A (or other image on which the flow velocity vector information is displayed) through the cursor 71, the trajectory 742 of the target point 741 marked with black thick line may be displayed on the corresponding images. The black arrows between the views may indicate the change of the image over time.

In one embodiment, in order to highlight the trajectory in the images, the methods described above may further include the following steps.

Figure 39:
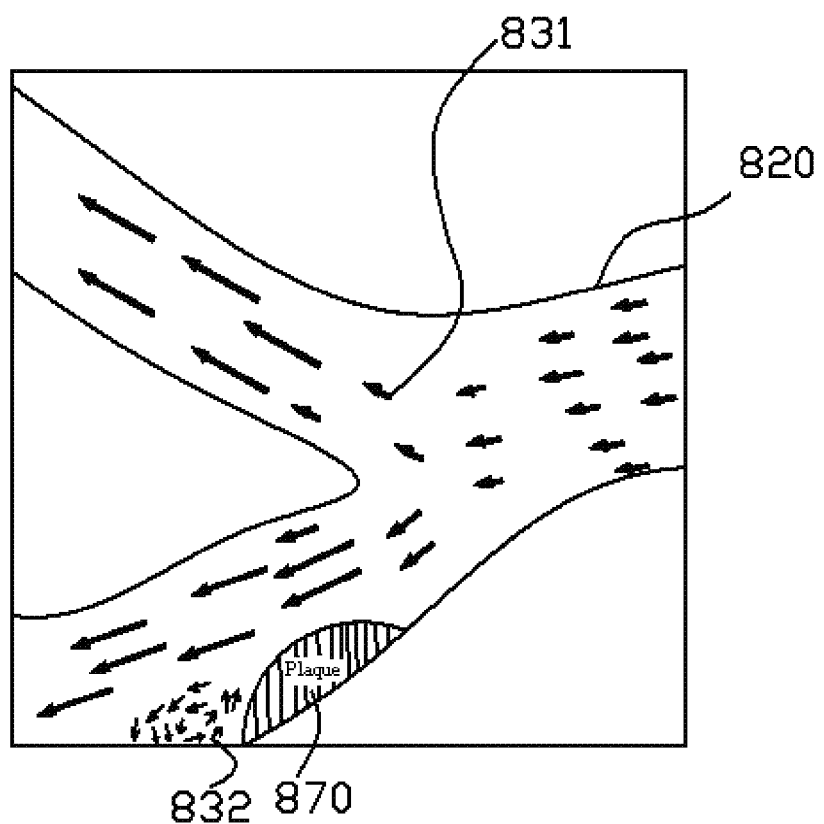
FIG. 39 schematically shows the flow swirl in the case of a plaque existing in an embodiment.

Firstly, the indication information of the connection line mentioned above inputted by the user may be obtained to generate a selection instruction. The indication information may include the shape, color or other information of the connection line. Thereafter, the parameters of the trajectory to be displayed on the display interface may be configured according to the indication information indicated by the selection instruction. The color herein may include any color obtained by adjusting the hue, the saturation or the contrast, etc. The connection line may be various forms. For example, the connection line may be the line formed by dots, solid line, dashed line, solid line with arrow, or any other mark which can represent the direction. When the indication information of the connection line is selected, the corresponding trajectory may be obtained. For example, the marks used for marking the flow velocity vector information in the image where the flow velocity vector information and the Doppler color flow image are comparatively displayed may include particles, arrows, flowing lines, squares, dots or any combination thereof, and the connection line may be solid line, dashed line, solid line with arrow or any other line. Thereafter, the trajectories displayed on the display interface may have corresponding color and shape. In the present embodiment, the target point to be tracked may be marked as necessary, and the trajectories of different target points may be represented to facilitate understanding the actual flow in the lesion in the scanning target and the reason by which the flow is generated. With this way, the flowing of the flow at the lesion in the scanning target may be shown more clearly. As shown in FIG. 39, the plaque 870 in the blood vessel may lead to flow swirl generated nearby. In the blood vessel region 820, two kinds of arrows are used to show the flow. The black thick arrows 831 may represent the ordinary flow velocity vector information, while the thin arrows 832 may represent the flow velocity vector information at the swirl. Different parameters may be used by the marks of the flow velocity vector information to indicate the rate level of the displayed flow velocity vector information. For example, the flow velocity vector information with low rate and high rate may be represented with different marks. By distinguishing the rate level of the flow, the flow velocity vector information at the swirl may be highlighted. The parameters herein may include the color, the transparency, the contrast, the shape or any combination thereof.

FIG. 7 is a flow chart of the ultrasound imaging method in one embodiment. It should be understood that, although the steps in the flow chart in FIG. 7 are successively displayed according to the arrows, these steps will not be limited to be performed necessarily in the order indicated by the arrows. Unless expressly stated in the present disclosure, the order for performing these steps will not be limited, and they may be performed in other order. Furthermore, at least a portion of the steps in FIG. 7 may include multiple sub-steps or multiple stages. These sub-steps or stages may not be performed necessarily at the same time, but can be performed at different times. These sub-steps or stages may not be performed necessarily sequentially, but may be performed in parallel or alternately with other steps or at least a portion of the sub-steps or stages of other steps.

Various embodiments have been described with reference to the corresponding steps. In the case where the logic does not contradict, the embodiments described above may be combined with each other to form new technical solutions, which are still in the scope of the present disclosure.

According to the embodiments described above, a person skilled in the art will understand that the methods in the embodiments described above may be implemented by software and necessary hardware platform. Alternatively, the methods may also be implemented by hardware. The methods of the present disclosure may be implemented as software products. The software products may be stored on a non-transitory computer-readable storage medium (such as ROM, disk, CD, server cloud space, etc.) and may include multiple instructions which, when executed, may enable a terminal (such as cell phone, computer, sever or network device, etc.) to perform the methods of the embodiments of the present disclosure.

In one embodiment, an ultrasound imaging system may be provided. The ultrasound imaging system may include:
 the probe 1;
 the transmitting circuit 2 which may excite the probe to transmitting the ultrasound beams to the scanning target;
 the receiving circuit 4 and the beam-forming unit 5 which may receive the echoes of the ultrasound beams to obtain the ultrasound echo signals;
 the data processing unit 9 which may obtain the flow velocity vector information of the target points in the scanning target, the Doppler flow velocity information and the ultrasound images of at least a portion of the scanning target based on the ultrasound echo signals, and superimpose the Doppler flow velocity information on the ultrasound images to form the Doppler color flow images; and
 the display 8 which may comparatively display the flow velocity vector information and the Doppler color flow images.

The step S100 may be performed by the transmitting circuit 2. The step S200 may be performed by the receiving circuit 4 and the beam-forming unit 5. The data processing unit 9 may include the signal processing unit 6 and/or the image processing unit 7. The calculation of the component of the flow velocity vector and the flow velocity vector information (i.e., the step S400) may be performed in the signal processing unit 6, and the image processing unit 7 may be used to perform the image processing mentioned above, such as obtaining the ultrasound images of at least a portion of the scanning target according to the ultrasound echo signals obtained in the pre-set time period in the step S300. The image processing unit 7 may further be used to perform the step S500 and output the data to the display for displaying. The steps performed by the circuits and units may be similar to those of the methods described with respect to the embodiments above and will not be described in detail again.

In one embodiment, the echoes of the plane ultrasound beams may be used to calculate the component of the flow velocity vector and the flow velocity vector information, and the echoes of the focused ultrasound beams may be used to calculate the ultrasound image. In this embodiment, the transmitting circuit may excite the probe to transmit the focused ultrasound beams to the scanning target. The receiving circuit and the beam-forming unit may receive the echoes of the focused ultrasound beams through the probe to obtain the focused ultrasound echo signals. The data processing unit may obtain the ultrasound image of at least a portion of the scanning target according to the focused ultrasound echo signals. In addition, the transmitting circuit may excite the probe to transmit the plane ultrasound beams to the scanning target, where the transmitting of the focused ultrasound beams may be inserted between the transmitting of the plane ultrasound beams. The receiving circuit and the beam-forming unit may receive the echoes of the plane ultrasound beams through the probe to obtain the plane ultrasound echo signals. The data processing unit may obtain the flow velocity vector information of the target points in the scanning target according to the plane ultrasound echo signals. The alternate transmitting methods of the two kinds of beams may be similar to those described above and will not be described in detail again.

In one embodiment, the display 8 may display the Doppler color flow images and the flow velocity vector information. As described above, many display modes may be provided. In one embodiment, the data processing unit 9 may further obtain the mode switching instruction for selecting the display mode inputted by the user through a button, a prompt box, an input box or a gesture instruction, etc., and switch the current display mode into any display mode described above according to the mode switching instruction.

In one embodiment, the data processing unit 9 may have two image data outputs which are outputted to the display 8, one of which may be the Doppler color flow image formed by superimposing the ultrasound image and the Doppler flow velocity information and the other may be the vector flow image formed by superimposing the ultrasound image and the flow velocity vector information.

The data processing unit 9 may be used to perform the steps in the step 300 and step 600 above, and, with respect to the details, the description of the methods above may be referenced.

In one embodiment, as shown in FIG. 1, the system may further include the human-machine interaction device 10 which may be used to obtain the instructions inputted by the user. The data processing unit 9 may further be used to perform at least one of the following steps:

switching the current display mode into any display mode obtained by comparatively displaying the flow velocity vector information and the Doppler color flow image according to the mode switching instruction inputted by the user;

displaying the spectrum obtained by pulse-wave Doppler imaging according to the mode switching instruction inputted by the user;

adjusting the playback speed of the flow velocity vector information of the target points in the step of comparatively displaying the flow velocity vector information and the Doppler color flow image according to the playback rate inputted by the user;

obtaining the distribution density inputted by the user and randomly selecting the target points in the scanning target according to the distribution density;

obtaining the indicated location inputted by the user and obtaining the target points according to the indicated location;

configuring one or more of the parameters of the color, the transparency, the contrast, the shape of the marks used for marking the flow velocity vector information in the background image according to the instruction inputted by the user to distinguish the flow velocity vector information or the flow velocity vector information at the swirls from the background image; and configuring the parameters of the trajectory to be displayed on the display interface according to the indication information with regard to the connection lines inputted by the user, where the trajectory of the target point may be formed by successively connecting the multiple positions in the ultrasound images to which the target point is successively moved with the connection lines.

The steps performed by the data processing unit 9 according to the instructions inputted by the user may be similar to those described above, and will not be described in detail again.

Therefore, the present disclosure provides the ultrasound flow imaging methods and the ultrasound imaging systems thereof which may overcome the drawbacks of the existing ultrasound imaging systems in flow imaging. The methods and systems may comparatively display the ordinary flow images and the vector flow to provide better observation for the user. Not only may the position being scanned be observed in real-time, but also the flow may be displayed more realistically. The various information of the flow velocity may be comparatively displayed, such that the user can understand the flow more comprehensively. More comprehensive, more accurate image data may be provided for the medical staffs, and new flow imaging display methods in the ultrasound imaging system may be created. In addition, the present disclosure may also provide new methods for calculating and displaying the flow velocity vector information of the target points, by which more real data with respect to the actual flow state of the flow may be provided, and the trajectories of the target points along the direction of the flow and based on the velocity of the flow may be presented intuitively. Furthermore, more personalized customization may also be provided by the present disclosure, such that more accurate, more intuitive data may be provided for the user to facilitate the observation to the flow state. In the embodiments, the vector flow images and the ordinary flow images may be displayed simultaneously, and may be calculated based on the same data. The ordinary flow images may be displayed in real time, while the vector flow images may be displayed in a slow manner. For example, firstly, the ordinary flow images are displayed in real time. After the freeze key is pushed, the data in several seconds before the push may be displayed in another window, as show in FIG. 11, where the ordinary flow images are displayed in real time on the left view while the vector flow images are displayed on the right view in slow rate. Since the images on the left view are displayed faster and the duration of the display is shorter, the images displayed on the left view may be displayed repeatedly. Therefore, when the vector flow images have been displayed for one cycle, the ordinary flow images have been displayed for N cycles. The images displayed on the right view may also be displayed repeatedly, or may also be displayed on a separate display.

In the present disclosure, the data with respect to the flow moving fast may be processed in order to achieve the slow play function. Therefore, the images may be slowly played in a certain times such that the human eye can better obtain the information with respect to the flow. In the embodiments above, a pseudo-real time display method may be provided, by which not only may the position being scanned be observed in real time, but also the flowing of the flow may be presented in a rate suitable for the human eye and comparatively with the Doppler flow information. It is a breakthrough improvement in the display technology in ultrasound imaging system.

The present disclosure may further provide a display method in which different colors may be used to represent the images of the grayscale changes of the region of interest in the enhanced B mode image and the images may be comparatively displayed with the flow velocity vectors.

With this method, the various information representing the flow velocities at the position of interest may be presented more clearly, and more reference information may be provided for the user. Therefore, the representation of the flow velocity at the corresponding positions may be overall understood, and the accuracy of the obtaining of the flow information may be improved.

Some embodiments of the present disclosure have been described above specifically and in detail. However, the description above shall not be interpreted as limitations to the present disclosure. Many modifications and improvements may be made by the person ordinarily skilled in the art without departing from the concepts of the present disclosure, which all belong to the scope of the present disclosure. Therefore, the protection scope of the present disclosure should be defined by the claims below.

What is claimed is:

1. A method for ultrasound flow imaging display, comprising:
   transmitting focused ultrasound beams to a scanning target selected by a user;
   receiving echoes of the focused ultrasound beams to obtain focused ultrasound echo signals;
   obtaining ultrasound images of at least a portion of the scanning target according to the focused ultrasound echo signals;
   displaying the ultrasound images on a display device;
   receiving, from the user, location information for a plurality of individual, user-selected target points within the user-selected scanning target, the user-selected target points comprising discrete, user-selected locations of moving particles of a blood flow within the user-selected scanning target;
   transmitting plane ultrasound beams to the user-selected scanning target;
   receiving echoes of the plane ultrasound beams to obtain plane ultrasound echo signals;
   obtaining flow velocity vector information for the user-selected target points in the user-selected scanning target according to the plane ultrasound echo signals;
   superimposing the ultrasound images and the flow velocity vector information to form vector flow images comprising a flow velocity vector for at least two moving particles selected by at least two user-selected target points, each of the at least two moving particles being graphically represented by a different fixed shape for uniquely distinguishing the at least two moving particles from each other over a time interval within the blood flow, wherein each flow velocity vector comprises an arrow, a length of the arrow representing a magnitude of the flow velocity vector of the respective moving particle and a direction of the arrow representing the direction of the flow velocity vector of the respective moving particle; and
   displaying the vector flow images on the display device.

2. The method of claim 1, further comprising:
   obtaining Doppler flow velocity information according to the plane ultrasound echo signals; and
   generating Doppler color flow images according to the Doppler flow velocity information; and
   comparatively displaying the Doppler color flow images and the vector flow images.

3. The method of claim 2, wherein the flow velocity vector information and the Doppler flow velocity information are derived from the plane ultrasound echo signals obtained in a same sampling period.

4. The method of claim 2, wherein the Doppler color flow images and the vector flow images are derived from the plane ultrasound echo signals obtained in two adjacent sampling periods, and wherein obtaining the flow velocity vector information of user-selected target points in the user-selected scanning target and the Doppler flow velocity information according to the plane ultrasound echo signals comprises:
   obtaining the flow velocity vector information according to the focused ultrasound echo signals obtained in one of the two adjacent sampling periods for forming the vector flow images; and
   obtaining the Doppler flow velocity information according to the plane ultrasound echo signals obtained in the other of the two adjacent sampling periods for forming the Doppler color flow images.

5. The method of claim 1, wherein, the flow velocity vector information of the user-selected target points comprises flow velocity vectors at positions in the ultrasound images to which a particular user-selected target point is successively moved, and wherein the method further comprises:
   marking the flow velocity vectors at the positions to which the particular user-selected target point is successively moved to form flowing marks which flow over time.

6. The method of claim 2, wherein comparatively displaying the vector flow images and the Doppler color flow images comprises performing one of:
   switching between displaying the vector flow images individually on a display and displaying the Doppler color flow images individually on the display; and
   simultaneously displaying the vector flow images and the Doppler color flow images.

7. The method of claim 6, wherein simultaneously displaying the vector flow images and the Doppler color flow images comprises:
   displaying the vector flow images and the Doppler color flow images in different windows.

8. The method of claim 2, wherein comparatively displaying the flow velocity vector information and the Doppler color flow images comprises at least one of:
   displaying at least a portion of the vector flow images in a first vector flow display region formed in a display region of the Doppler color flow images; and
   displaying the flow velocity vector information in a second vector flow display region formed in the display region of the Doppler color flow images.

9. The method of claim 8, wherein comparatively displaying the flow velocity vector information and the Doppler color flow images further comprises at least one of:
   when the first vector flow display region is moved, displaying at least a portion of the vector flow images which correspond to the first vector flow display region in the first vector flow display region; and
   when the second vector flow display region is moved, displaying, in the second vector flow display region, the flow velocity vector information of the user-selected target points contained in the second vector flow display region.

10. The method of claim 2, wherein comparatively displaying the flow velocity vector information and the Doppler color flow images comprises configuring one or more of color, transparency, contrast and shape of the marks which are used to mark the flow velocity vector information in a background image to distinguish the marks from the background image or indicate rate level of the displayed flow velocity vector information.

11. The method of claim 10, wherein a transparency of the background image is adjustable or changes gradually.

12. The method of claim 2, wherein comparatively displaying the flow velocity vector information and the Doppler color flow images further comprises:
    switching current display mode into any display mode obtained by comparatively displaying the flow velocity vector information and the Doppler color flow images according to a mode switching instruction.

13. The method of claim 1, further comprising:
    displaying Doppler spectrum images obtained by pulse-wave Doppler imaging according to a mode switching instruction inputted.

14. The method of claim 1, further comprising at least one of:
    displaying Doppler spectrum image at a position of a cursor; and
    displaying Doppler spectrum images at one or more pre-set positions.

15. The method of claim 2, wherein comparatively displaying the flow velocity vector information and the Doppler color flow images further comprises at least one of:
    displaying the flow velocity vector information of the user-selected target points in a slow manner; and
    freezing the Doppler color flow images.

16. The method of claim 2, wherein freezing the Doppler color flow images comprises one of:
    displaying the Doppler color flow images repeatedly; and
    displaying the Doppler color flow images in a slow manner.

17. The method of claim 16, wherein displaying the flow velocity vector information of the user-selected target points in a slow manner comprises:
    obtaining a ratio selection instruction representing a play ratio selected by the user; and
    adjusting a play speed of the flow velocity vector information of the user-selected target points when the flow velocity vector information and the Doppler color flow images are comparatively displayed according to the play ratio selected by the ratio selection instruction.

18. The method of claim 1, wherein the user-selected target points are obtained by obtaining a location indicating instruction inputted by a user and obtaining the user-selected target points according to the location indicating instruction.

19. The method of claim 1, further comprising:
    displaying one or more of an absolute value of flow velocity, a direction of velocity, and an acceleration at a position of a cursor on a display interface.

20. The method of claim 19, wherein displaying one or more of the absolute value of flow velocity and the direction of velocity of the flow velocity vector information at the position of the cursor on the display interface comprises at least one of:
    displaying a graph whose area is related to the absolute value of velocity on the display interface which is used for representing the absolute value of velocity of the flow velocity vector information;
    displaying a direction indication line pointing to a direction of velocity on the display interface which is used for representing the direction of velocity of the flow velocity vector information;
    displaying a direction indication line pointing to a direction of velocity in the graph which is used for representing the direction of velocity of the flow velocity vector information;
    displaying text information representing the flow velocity vector information on the display interface; and
    displaying text information representing the flow velocity vector information in a region near the graph.

21. The method of claim 19, wherein displaying one or more of the absolute value of flow velocity and the direction of velocity of the flow velocity vector information at the position of the cursor on the display interface comprises at least one of:
    displaying a circle whose radius is equal to the absolute value of velocity on the display interface for displaying the absolute value of velocity of the flow velocity vector information at the position of the cursor on the display interface;
    displaying an indication line which intersects with the circle and points to the direction of velocity for displaying the direction of velocity of the flow velocity vector information at the position of the cursor on the display interface; and
    displaying text information representing the flow velocity vector information near the circle on the display interface.

22. The method of claim 1, further comprising:
    successively connecting multiple positions of a user-selected target point to which said user-selected target point is successively moved in the ultrasound images with connection lines to form a trajectory of said user-selected target point.

23. The method of claim 22, further comprising:
    obtaining indication information with regard to the connection lines inputted by a user to generate a selection instruction; and
    configuring parameters of the trajectory displayed on a display interface according to the selection instruction.

24. The method of claim 2, further comprising:
    transmitting the plane ultrasound beams to the user-selected scanning target along an ultrasound propagation direction;
    receiving the echoes of the plane ultrasound beams to obtain a group of plane ultrasound echo signals;
        obtaining at least two frames of image data according to the group of plane ultrasound echo signals, selecting a tracking region in a first frame of image data and searching a tracking result region in a second frame of image data which corresponds to the tracking region, and obtaining the flow velocity vector information of the user-selected target points according to locations of the tracking region and the tracking result region and a time interval between the first frame and the second frame of image data; and
    obtaining the Doppler flow velocity information according to the group of plane ultrasound echo signals.

25. An ultrasound imaging system, comprising:
    a probe;
    a display device;
    a transmitting circuit which excites the probe to alternately transmit focused ultrasound beams and plane ultrasound beams to a scanning target selected by a user;
    a receiving circuit and a beam-forming unit which receive echoes of the focused ultrasound beams and plane ultrasound beams to respectively obtain focused ultrasound echo signals and plane ultrasound echo signals; and a data processing unit which:
- obtains ultrasound images of at least a portion of the scanning target according to the focused ultrasound echo signals;
- displays the ultrasound images on the display device;
- receives a user-specified target point distribution density for target points within the user-selected scanning target;
- randomly selects a specific number of target points representing locations of moving particles of a blood flow within the user-selected scanning target according to the user-specified target point distribution density within the user-selected scanning target;
- transmits plane ultrasound beams to the user-selected scanning target;
- obtains flow velocity vector information for the randomly selected target points in the user-selected scanning target according to the plane ultrasound echo signals;
- obtains Doppler flow velocity information according to the plane ultrasound echo signals;
- superimposes the ultrasound images and the flow velocity vector information to form vector flow images comprising a flow velocity vector for at least two moving particles selected by at least two of the randomly-selected target points, each of the at least two moving particles being graphically represented by a different fixed shape for uniquely distinguishing the at least two moving particles from each other over a time interval within the blood flow, wherein the flow velocity vector comprises an arrow, a length of the arrow representing a magnitude of the flow velocity vector at the respective moving particle and a direction of the arrow representing the direction of the flow velocity vector at the respective moving particle;
- superimposes the ultrasound images and the Doppler flow velocity information to form Doppler color flow images; and
- comparatively displays the vector flow images and the Doppler color flow images on the display device.

26. The ultrasound imaging system of claim 25, wherein:
the transmitting circuit excites the probe to transmit the plane ultrasound beams to the user-selected scanning target along an ultrasound propagation direction;
the receiving circuit and the beam-forming unit receive the echoes of the plane ultrasound beams to obtain a group of plane ultrasound echo signals; and
the data processing unit further calculates a displacement and direction of movement of the user-selected target points in the user-selected scanning target in a pre-set time interval according to the group of plane ultrasound echo signals to generate the flow velocity vector information of the user-selected target points, and obtains the Doppler flow velocity information according to the group of plane ultrasound echo signals.

27. The ultrasound imaging system of claim 25, wherein:
the transmitting circuit excites the probe to transmit the plane ultrasound beams along an ultrasound propagation direction;
the receiving circuit and the beam-forming unit receive the echoes of the plane ultrasound beams to obtain a group of plane ultrasound echo signals; and
the data processing unit obtains at least two frames of image data according to the group of plane ultrasound echo signals, selects a tracking region in a first frame of image data and searches a tracking result region in a second frame of image data which corresponds to the tracking region, obtains the flow velocity vector information of the randomly-selected target points according to locations of the tracking region and the tracking result region and a time interval between the first frame and the second frame of image data, and obtains the Doppler flow velocity information according to the group of plane ultrasound echo signals.

28. The ultrasound imaging system of claim 25, further comprising:
a human-machine interaction device which is used to obtain instructions inputted by a user;
wherein the data processing unit further obtains a distribution density instruction selected by the user and randomly chooses an initial set of target points in the randomly-selected scanning target according to the distribution density instruction from which the user selects the user-selected target points.

29. The method of claim 2, further comprising alternately transmitting the focused ultrasound beams and the plane ultrasound beams, wherein the Doppler flow velocity information is derived from the plane ultrasound beams.

30. The method of claim 1, further comprising alternately transmitting the focused ultrasound beams and the focused ultrasound beams, wherein the vector flow images are derived from echoes of the plane beams.

31. The method of claim 1, wherein one plane ultrasound beam is transmitted after a plurality of focused ultrasound beams.

32. The method of claim 1, wherein a first plane ultrasound beam is transmitted in a first ultrasound propagation direction and wherein a second plane ultrasound beam is transmitted in a second ultrasound propagation direction.

33. The method of claim 32, wherein each flow velocity vector includes at least two arrows, a length and direction of a first arrow respectively corresponding to a magnitude and direction of the flow velocity vector according to the first plane ultrasound beam in the first ultrasound propagation direction, and a length and direction of a second arrow respectively corresponding to a magnitude and direction of the flow velocity vector according to the second plane ultrasound beam in the first ultrasound propagation direction.

34. The method of claim 1, wherein the fixed shape used to represent each moving particle is selected by a user.

* * * * *